(12) United States Patent
John et al.

(10) Patent No.: US 10,561,565 B2
(45) Date of Patent: Feb. 18, 2020

(54) ASSIST GARMENT, METHOD FOR CONTROLLING CONTROLLER OF ASSIST GARMENT, AND RECORDING MEDIUM

(71) Applicant: Panasonic Intellectual Property Management Co., Ltd., Osaka (JP)

(72) Inventors: Stephen William John, Kyoto (JP); Katsuhiko Asai, Nara (JP); Takayuki Nagata, Osaka (JP); Masaki Yamamoto, Nara (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 751 days.

(21) Appl. No.: 14/988,871

(22) Filed: Jan. 6, 2016

(65) Prior Publication Data
US 2016/0213548 A1    Jul. 28, 2016

(30) Foreign Application Priority Data

Jan. 28, 2015  (JP) ................................. 2015-014663

(51) Int. Cl.
*A61H 3/00* (2006.01)
*A61H 1/02* (2006.01)
(Continued)

(52) U.S. Cl.
CPC .............. *A61H 3/00* (2013.01); *A41D 1/002* (2013.01); *A41D 13/0015* (2013.01);
(Continued)

(58) Field of Classification Search
CPC . A61H 1/00; A61H 1/02; A61H 1/002; A61H 1/0237; A61H 1/0262;
(Continued)

(56) References Cited

U.S. PATENT DOCUMENTS

| 7,874,997 B2* | 1/2011 | Jaccard ................. A61F 5/0118 128/846 |
| 7,976,924 B2* | 7/2011 | Stanford, Jr. ........ A62B 17/005 428/92 |
| 9,266,233 B2* | 2/2016 | Kornbluh ............... B25J 9/0006 |
| 2003/0030397 A1* | 2/2003 | Simmons ............... B25J 9/0006 318/568.11 |

(Continued)

FOREIGN PATENT DOCUMENTS

| CN | 1431084 | 7/2003 |
| JP | 2003-250842 | 9/2003 |

(Continued)

OTHER PUBLICATIONS

Chinese Search Report dated Apr. 30, 2019 in Chinese Patent Application No. 201510992696.5, with English Translation.

*Primary Examiner* — Tu A Vo
(74) *Attorney, Agent, or Firm* — Wenderoth, Lind & Ponack, L.L.P.

(57) ABSTRACT

An assist garment worn on a part of a human body includes a plurality of garment-fitting actuators that are placed linearly along at least one end portion of a garment body and driven to extend and contract, a plurality of assisting actuators that are placed linearly on the garment body to cross the fitting actuators and driven to extend and contract, and a controller that individually controls the drive of the assisting actuators and the drive of the fitting actuators.

6 Claims, 47 Drawing Sheets

(51) Int. Cl.
*A61B 5/04* (2006.01)
*A61B 5/11* (2006.01)
*A41D 1/00* (2018.01)
*A61F 2/50* (2006.01)
*A41D 13/00* (2006.01)
*A61B 5/0488* (2006.01)
*A61B 5/00* (2006.01)

(52) U.S. Cl.
CPC ........ *A61B 5/04888* (2013.01); *A61B 5/1107* (2013.01); *A61B 5/6804* (2013.01); *A61F 2/50* (2013.01); *A61H 1/02* (2013.01); *A61H 1/0244* (2013.01); *A61H 1/0277* (2013.01); *A61H 1/0285* (2013.01); *A61H 1/0288* (2013.01); *A61H 2003/007* (2013.01); *A61H 2201/0184* (2013.01); *A61H 2201/0207* (2013.01); *A61H 2201/0214* (2013.01); *A61H 2201/0228* (2013.01); *A61H 2201/1207* (2013.01); *A61H 2201/1238* (2013.01); *A61H 2201/165* (2013.01); *A61H 2201/501* (2013.01); *A61H 2201/5002* (2013.01); *A61H 2201/5061* (2013.01); *A61H 2201/5084* (2013.01); *A61H 2230/085* (2013.01); *A61H 2230/605* (2013.01)

(58) Field of Classification Search
CPC ................ A61H 1/0277; A61H 1/0274; A61H 2201/5051; A61H 2201/5053; A61H 2201/5056; A61H 2201/5058; B25J 9/00; B25J 9/0006; B25J 9/16; B25J 9/123; A61F 5/00; A61F 5/01; A61F 5/0102; A61F 5/0104; A61F 5/0106; A61F 5/0109; A61F 5/0111; A61F 5/0181; A61F 5/0125; A61B 2562/0219; A61B 2562/0271; A61B 5/68; A61B 5/6801; A61B 5/6802
See application file for complete search history.

(56) References Cited

U.S. PATENT DOCUMENTS

| | | | |
|---|---|---|---|
| 2003/0125781 A1* | 7/2003 | Dohno | A63B 21/00181 607/75 |
| 2004/0267331 A1* | 12/2004 | Koeneman | A61H 1/02 607/49 |
| 2006/0122544 A1* | 6/2006 | Ciluffo | A41D 13/0015 601/15 |
| 2006/0287621 A1* | 12/2006 | Atkinson | A61H 9/0078 601/151 |
| 2009/0234265 A1* | 9/2009 | Reid, Jr. | A61H 9/0078 602/61 |
| 2011/0166491 A1* | 7/2011 | Sankai | A41D 13/1281 601/84 |
| 2011/0190675 A1* | 8/2011 | Vess | A61H 9/0092 601/152 |
| 2012/0029399 A1* | 2/2012 | Sankai | A61B 5/04888 601/40 |
| 2015/0088043 A1* | 3/2015 | Goldfield | A61F 5/01 602/6 |
| 2015/0173993 A1* | 6/2015 | Walsh | B25J 9/0006 414/4 |
| 2015/0366504 A1* | 12/2015 | Connor | A61B 5/6804 600/301 |
| 2016/0058644 A1* | 3/2016 | Cheatham, III | A61H 1/008 601/84 |
| 2016/0107309 A1* | 4/2016 | Walsh | A61H 3/00 248/550 |
| 2016/0120734 A1* | 5/2016 | Ishikawa | A45F 3/04 601/151 |

FOREIGN PATENT DOCUMENTS

| | | |
|---|---|---|
| JP | 2004-150283 | 5/2004 |
| JP | 2007-068794 | 3/2007 |
| JP | 2008-035682 | 2/2008 |
| JP | 2011-036558 | 2/2011 |
| JP | 2014-050490 | 3/2014 |
| JP | 2014-087636 | 5/2014 |
| JP | 2014-133121 | 7/2014 |

* cited by examiner

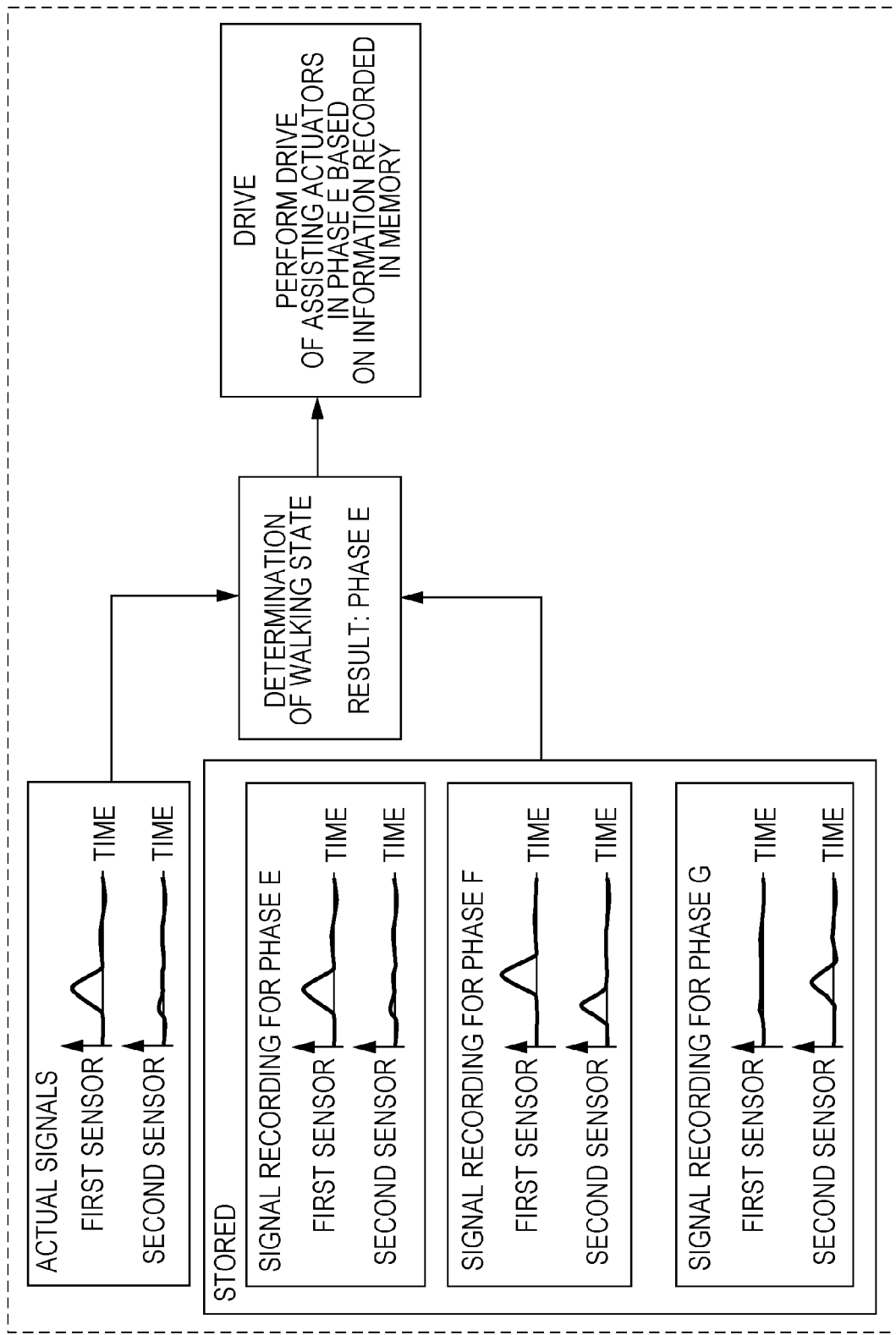

FIG. 3C

| PHASE | TIME | FIRST SENSOR | SECOND SENSOR |
|---|---|---|---|
| E | t1 | 1 | 0 |
|  | t2 | 2 | 0 |
|  | t3 | 3 | 0 |
|  | t4 | 2 | 0 |
|  | --- |  |  |

FIG. 3D

| PHASE | TIME | ACTUATOR | | | | |
|---|---|---|---|---|---|---|
|  |  | A | B | C | D | E |
| E | t1 | 0 | 0 | 1 | 0 | 0 |
|  | t2 | 0 | 1 | 2 | 1 | 0 |
|  | t3 | 0 | 2 | 3 | 2 | 0 |
|  | t4 | 0 | 1 | 1 | 1 | 0 |
|  | --- |  |  |  |  |  |

ASSIST GARMENT, METHOD FOR CONTROLLING CONTROLLER OF ASSIST GARMENT, AND RECORDING MEDIUM

BACKGROUND

1. Technical Field

The present disclosure relates to an assist garment that is worn on a living body to supplement the force generated by the living body to assist the motion of the living body, a method for controlling a controller of an assist garment, and a recording medium.

2. Description of the Related Art

In related art, human body motion assist devices exist in which a body-mounted part in the form of a mesh of fabric, for example, is mounted on a joint part of the human body such as the knee, and an actuator provided in the body-mounted part is driven to supplement the force generated by the human body to assist the wearer in performing daily activities (see, for example, Japanese Unexamined Patent Application Publication No. 2003-250842).

Such related art devices leave room for improvement in, for example, allowing the assist force from the actuator to be properly exerted on the living body.

SUMMARY

One non-limiting and exemplary embodiment provides an assist garment that allows an assist force to be properly exerted on a living body.

In one general aspect, the technique disclosed here feature an assist garment worn on a part of a living body, including a plurality of assisting actuators that, when worn on the part, are placed linearly in a direction of extension and contraction of a muscle of the part, the assisting actuators being driven to extend and contract, a plurality of fitting actuators placed linearly to cross the assisting actuators, the fitting actuators being driven to extend and contract, and a controller that individually controls driving of the assisting actuators and driving of the fitting actuators.

Exemplary embodiments of the present disclosure allow the assist force from the assisting actuators to be properly exerted on, for example, a muscle of a living body.

It should be noted that general or specific embodiments may be implemented as a system, a method, an integrated circuit, a computer program, a computer readable recording medium, or any selective combination thereof. Examples of a computer readable recording medium include a non-volatile recording medium such as a compact disc-read only memory (CD-ROM).

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

BRIEF DESCRIPTION OF THE DRAWINGS

FIG. 3B illustrates a determination made by comparison;

FIG. 3C illustrates a signal of Phase E of a time response pattern used in the determination illustrated in FIG. 3B;

FIG. 3D illustrates an example of driving of assisting actuators (Actuators A to E as a representative example) in Phase E, based on the determination illustrated in FIG. 3B;

DETAILED DESCRIPTION

Figure 1:
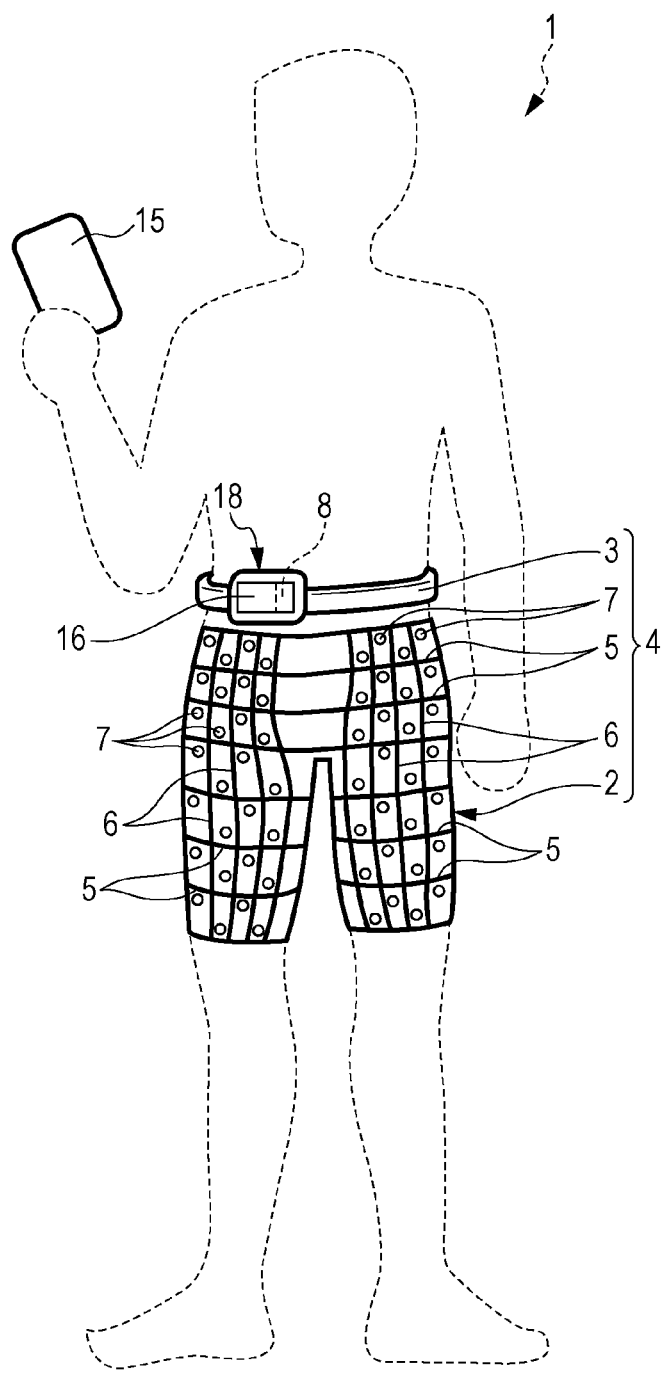
FIG. 1 illustrates an assist garment according to a first embodiment of the present disclosure when worn on a user.

Hereinafter, embodiments of the present disclosure will be described in detail with reference to the drawings.

Before describing embodiments of the present disclosure in detail with reference to the drawings, various aspects of the present disclosure will be described.

According to a first aspect of the present disclosure, there is provided an assist garment including:

a plurality of assisting actuators that, when worn on the part, are placed linearly in a direction of extension and contraction of a muscle of the part, the assisting actuators being driven to extend and contract;

a plurality of fitting actuators placed linearly to cross the assisting actuators, the fitting actuators being driven to extend and contract; and a controller that individually controls driving of the assisting actuators and driving of the fitting actuators.

Using only assisting actuators as in assist garments in related art may lead to formation of localized wrinkles on the assist garment during extension and contraction of the assisting actuators. The assist garment with such wrinkles may not properly fit to the human body. This limits, for example, the adaptability of the assist garment to various human body shapes, resulting in improper fit or improper placement of the assist garment on the human body. As a result, the assist force from the actuators is not sufficiently exerted on the muscles in the human body.

In this aspect of the present disclosure, the fitting actuators are provided in addition to the assisting actuator so as to cross the assisting actuators. This configuration not only allows the assist garment to be extended and contracted in the direction of extension and contraction of the muscle by using the assisting actuators, but also allows the assist garment to be contracted in a direction crossing the assisting actuators by using the fitting actuators. Use of such fitting actuators minimizes formation of localized wrinkles on the assist garment during extension and contraction of the assisting actuators, while allowing for a more proper fit of the assist garment on the living body. This allows the assist force from the assisting actuators to be properly exerted on the muscle in the living body.

An exemplary implementation of the above aspect of the present disclosure includes the following features:

the assist garment further includes an assist garment body having a first end portion and a second end portion;

the assisting actuators are placed linearly in a direction oriented from the first end portion of the assist garment body toward the second end portion; and the fitting actuators are placed linearly in a circumferential direction of at least one of the first end portion and the second end portion of the assist garment body.

According to this aspect of the present disclosure, the assisting actuators exert an assist force in a direction oriented from the first end portion of the assist garment body toward the second end portion. Further, with the fitting actuators placed in the circumferential direction of at least one of the first end portion and the second end portion, the fitting actuators may be contracted to provide for a more proper fit of the end portion of the assist garment on the living body.

In an exemplary implementation of the above aspect of the present disclosure, when worn on the part, the fitting actuators are placed linearly in a circumferential direction of the part.

According to this aspect of the present disclosure, with the fitting actuators placed in the circumferential direction of the part, the fitting actuators may be contracted to achieve a more proper fit of the entire assist garment on the part.

An exemplary implementation of the above aspect of the present disclosure includes the following features:

the assist garment further includes a plurality of sensors placed at or around placement positions of the assisting actuators and at or around placement positions of the fitting actuators to detect whether the assist garment is in contact with the living body; and the controller controls driving of the fitting actuators based on a detection result obtained from the sensors.

According to this aspect of the present disclosure, the drive of the fitting actuators is controlled based on detections from the sensors, thus allowing for more reliable tightening of the assist garment. This provides for a more proper fit on the living body, thus allowing the assist force from the assisting actuators to be exerted on the muscle.

An exemplary implementation of the above aspect of the present disclosure includes the following features:

each of the sensors is an electromyogram sensor that detects a voltage generated when the muscle is about to be activated; and the controller controls driving of the assisting actuators based on a detection result obtained from the electromyogram sensor.

An EMG sensor detects a voltage generated when a muscle is about to be activated, that is, an EMG sensor detects not a voltage generated after actual muscle activation but a voltage generated immediately before muscle activation. Consequently, according to this aspect of the present disclosure, the drive of the assisting actuators may be controlled based on a detection of a voltage generated immediately before muscle activation. This results in improved following capability of the assist provided by the assisting actuators.

In an exemplary implementation of the above aspect of the present disclosure, the sensors are placed in a region of the part corresponding to the muscle at a density higher than a density at which the sensors are placed in a region other than the region corresponding to the muscle.

A region corresponding to a muscle represents an area where a relatively large movement occurs when the muscle is moved, within a part of the living body on which the assist garment is worn. Consequently, if the sensors used are, for example, EMG sensors, according to this aspect of the present disclosure, placing comparatively more EMG sensors focusing on the region corresponding to the muscle enables more reliable detection of muscle activation, allowing for a more proper assist.

In an exemplary implementation of the above aspect of the present disclosure, the controller controls driving of one or more of the assisting actuators which are placed in proximity to one or more of the sensors which are placed in a region corresponding to the muscle, based on a detection result from the sensors.

According to this aspect of the present disclosure, the drive of the assisting actuators near the region corresponding to the muscle is controlled. This allows the assist force from the assisting actuators to be exerted on the muscle with increased reliability.

In an exemplary implementation of the above aspect of the present disclosure, the assisting actuators are placed in a region of the part corresponding to the muscle at a density higher than a density at which the assisting actuators are placed in a region other than the region corresponding to the muscle.

According to this aspect of the present disclosure, a large number of assisting actuators are placed focusing on the region corresponding to the muscle. This allows comparatively more assisting actuators to exert an assist force on the muscle, and also enables selection of more appropriate assisting actuators from the assisting actuators.

An exemplary implementation of the above aspect of the present disclosure includes the following features:

the assist garment further includes an assist garment body having an end portion; and the fitting actuators are placed in a region corresponding to the end portion of the assist garment body at a density higher than a density at which the fitting actuators are placed in a region other than the region corresponding to the end portion.

According to this aspect of the present disclosure, comparatively more fitting actuators are placed focusing on the region corresponding to an axial end portion of the living body on which the assist garment is worn. This makes it possible to prevent the assist garment body from sliding down or sliding up.

An exemplary implementation of the above aspect of the present disclosure includes the following features:

the fitting actuators include one or more first actuators and one or more second actuators;

upon contracting the first actuators, the controller determines, based on a detection result obtained from one or more of the sensors which are located at placement positions of the first actuators or in areas around the placement positions of the first actuators, whether all of the placement positions of the first actuators or all of the areas around the placement positions of the first actuators are in contact with the living body; and the controller contracts the second actuators when the controller determines that all of the placement positions of the first actuators or all of the areas around the placement positions of the first actuators are in contact with the living body.

According to this aspect of the present disclosure, the fitting actuators are not contracted all at once but one by one in a stepwise manner. This configuration minimizes formation of localized wrinkles on the assist garment due to contraction of the fitting actuators. This ensures that once the contraction of all the fitting actuators is complete, the areas around individual fitting actuators are all in contact with the living body.

In an exemplary implementation of the above aspect of the present disclosure, the second actuators are placed adjacent to the first actuators.

According to this aspect of the present disclosure, the fitting actuators are contracted in a stepwise manner in a predetermined direction. This configuration minimizes formation of wrinkles on the assist garment, while allowing for a more proper fit of the assist garment on the living body.

An exemplary implementation of the above aspect of the present disclosure includes the following features:

the assist garment further includes an assist garment body having a first axial end portion and a second axial end portion; and the controller contracts the fitting actuators sequentially from the first axial end portion of the assist garment body toward the second axial end portion.

According to this aspect of the present disclosure, the fitting actuators are contracted sequentially beginning at the first axial end portion of the garment body and proceeding toward the second axial end portion. This configuration minimizes formation of wrinkles on the assist garment, while allowing for a more proper fit of the assist garment on the living body.

An exemplary implementation of the above aspect of the present disclosure includes the following features:

the assist garment further includes a notifier;

the fitting actuators include one or more first actuators and one or more second actuators; and when the controller determines, based on a detection result obtained from one or more of the sensors which are located at placement positions of the first actuators or in areas around the placement positions of the first actuators, that not all of the placement positions of the first actuators or not all of the areas around the placement positions of the first actuators are in contact with the living body, the controller uses the notifier to provide notification indicating that the assist garment is not in contact with the living body.

This aspect of the present disclosure makes it possible to notify the user that the assist garment is not in contact with the living body, that is, wrinkles have formed on the assist garment. This configuration makes it possible to urge the living body wearing the assist garment to adjust the garment and remove the wrinkles, allowing for a more proper fit of the assist garment on the living body.

In an exemplary implementation of the above aspect of the present disclosure, the controller drives the first actuators to extend and contract to generate a vibration, together with the notification provided using the notifier.

This aspect of the present disclosure allows the user as an example of a living body to recognize where the assist garment is not in contact with the living body, that is, where wrinkles have formed on the assist garment, thus more reliably urging the user to remove the wrinkles.

In an exemplary implementation of the above aspect of the present disclosure, each of the fitting actuators is a linearly shaped actuator that is caused to contract by application of heat.

In an exemplary implementation of the above aspect of the present disclosure, each of the fitting actuators is a linearly shaped pneumatic actuator that is caused to extend and contract by adjustment of air pressure.

In an exemplary implementation of the above aspect of the present disclosure, the controller first drives the fitting actuators to contract, and after contraction of the fitting actuators is completed, the controller drives the assisting actuators to extend and contract.

According to this aspect of the present disclosure, first, the fitting actuators are used to change the assist garment from a loosely worn state to a tightened state, that is, a state in which the assist garment fits securely on the living body. The assisting actuators are then extended and contracted in that state. Consequently, compared to using only the assisting actuators, this configuration minimizes formation of localized wrinkles during extension and contraction of the assisting actuators. This ensures a secure fit of the assist garment on the living body, allowing the assist force from the assisting actuators to be more properly and more reliably exerted on the muscle in the living body.

According to this aspect of the present disclosure, the fitting actuators are provided in addition to the assisting actuator so as to cross the assisting actuators. This configuration not only allows the assist garment to be extended and contracted in the direction of extension and contraction of the muscle by using the assisting actuators, but also allows the assist garment to be contracted in a direction crossing the assisting actuators by using the fitting actuators. Use of such fitting actuators minimizes formation of localized wrinkles on the assist garment during extension and contraction of the assisting actuators, while allowing for a more proper fit of the assist garment on the living body. This allows the assist force from the assisting actuators to be more properly exerted on the muscle in the living body.

According to another aspect of the present disclosure, there is provided a method for controlling a controller of an assist garment, the assist garment including a plurality of assisting actuators that, when worn on a living body, are placed linearly in a direction of extension and contraction of a muscle of the living body, the assisting actuators being driven to extend and contract, a plurality of fitting actuators placed linearly to cross the assisting actuators, the fitting actuators being driven to extend and contract, a plurality of sensors placed around the assisting actuators and the fitting actuators, and a controller that individually controls driving of the assisting actuators and driving of the fitting actuators, based on a detection result from the sensors, the method including:

contracting one or more first actuators of the fitting actuators;

detecting whether the assist garment is in contact with the living body, by using one or more of the sensors which are placed in areas around the first actuators;

determining, based on a detection result from the sensors, whether all of the areas around the first actuators are in contact with the living body; and contracting one or more second actuators of the fitting actuators when the controller determines that all of the areas around the first actuator are in contact with the living body.

According to this aspect of the present disclosure, the fitting actuators are provided in addition to the assisting actuator so as to cross the assisting actuators. This configuration not only allows the assist garment to be extended and contracted in the direction of extension and contraction of the muscle by using the assisting actuators, but also allows the assist garment to be contracted in a direction crossing the assisting actuators by using the fitting actuators. Use of such fitting actuators minimizes formation of localized wrinkles on the assist garment during extension and contraction of the assisting actuators, while allowing for a more proper fit of the assist garment on the living body. This allows the assist force from the assisting actuators to be more properly exerted on the muscle in the living body.

According to another aspect of the present disclosure, there is provided a recording medium storing a control program for causing an apparatus including a processor to execute an assist process in an assist garment, the recording medium being non-transitory and computer readable, the assist garment including a plurality of assisting actuators that, when worn on a living body, are placed linearly in a direction of extension and contraction of a muscle of the living body, the assisting actuators being driven to extend and contract, a plurality of fitting actuators placed linearly to cross the assisting actuators, the fitting actuators being driven to extend and contract, a plurality of sensors placed around the assisting actuators and the fitting actuators, and a controller that individually controls driving of the assisting actuators and driving of the fitting actuators, based on a detection result from the sensors, the assist process including causing a computer of the controller to execute functions including:

contracting one or more first actuators of the fitting actuators;

detecting whether the assist garment is in contact with the living body, by using one or more of the sensors which are placed in areas around the first actuators;

determining, based on a detection result from the sensors, whether all of the areas around the first actuators are in contact with the living body; and contracting one or more second actuators of the fitting actuators when the controller determines that all of the areas around the first actuators are in contact with the living body.

According to this aspect of the present disclosure, the fitting actuators are not contracted all at once but one by one in a stepwise manner. This configuration minimizes formation of localized wrinkles on the assist garment due to contraction of the fitting actuators. This ensures that once the contraction of all the fitting actuators is complete, the areas around individual fitting actuators are all in contact with the living body.

According to another aspect of the present disclosure, there is provided an assist garment including:

a plurality of first actuators that do not cross each other;

a plurality of second actuators that do not cross each other;

a plurality of sensors including a plurality of first sensors that measure muscle activities; and a controller, in which the controller controls the first actuators to contract, and after finishing contraction of the first actuators, the controller controls one or more of the second actuators to contract and/or extend based on information obtained from the first sensors.

An exemplary implementation of the above aspect of the present disclosure includes the following features:

the first actuators include a (i−1)-th actuator group including one or more actuators, and an i-th actuator group including one or more actuators;

immediately after the controller controls the one or more actuators included in the (i−1)-th actuator group to contract, the controller controls the one or more actuators included in the i-th actuator group to contract;

the (i−1)-th actuator group is adjacent to the i-th actuator group; and i is a natural number greater than or equal to two, and is less than or equal to a total number of the first actuators.

In an exemplary implementation of the above aspect of the present disclosure, each of the first actuators crosses each of the second actuators.

First Embodiment

Hereinafter, a first embodiment of the present disclosure will be described with reference to the drawings.

Configuration

Figure 2:
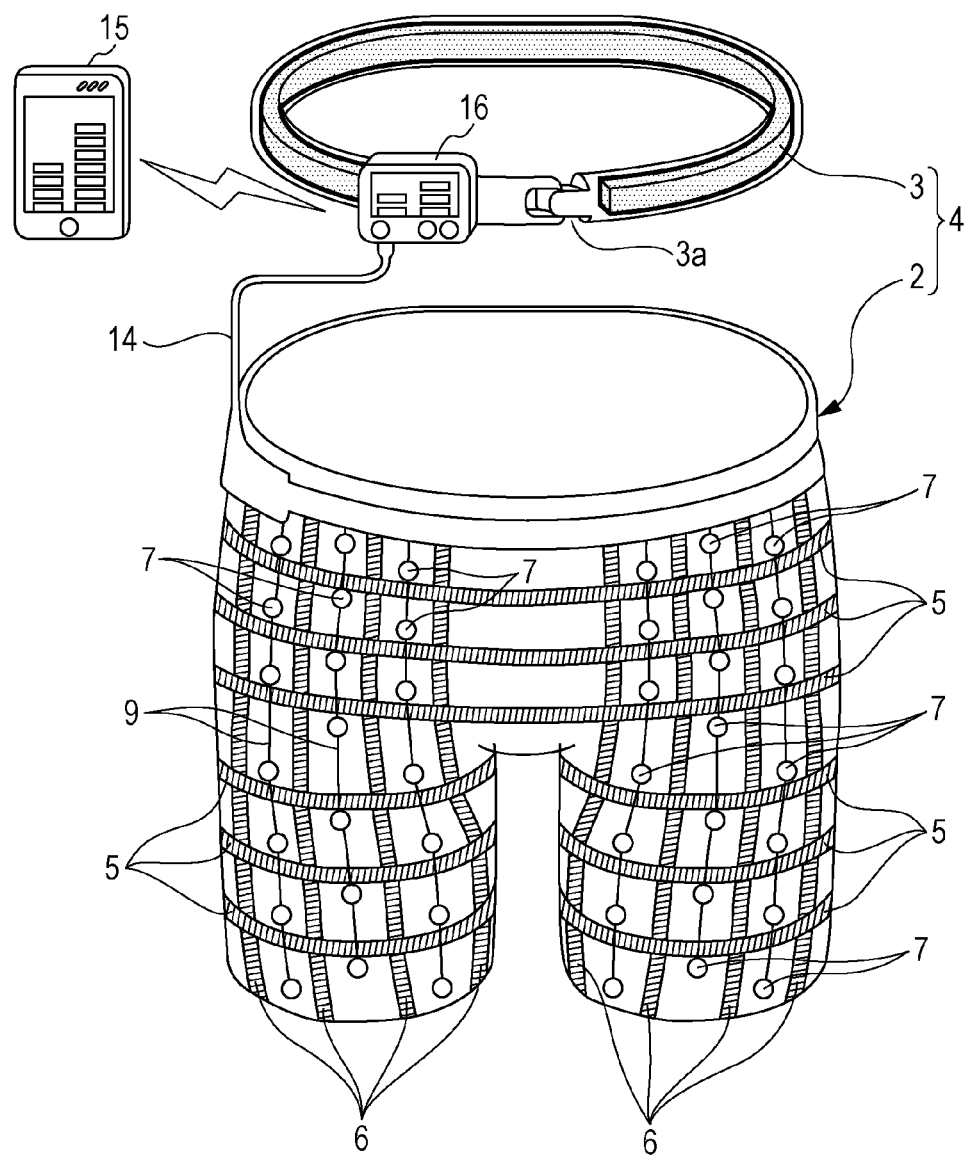
FIG. 2 is a perspective view of the assist garment illustrated in FIG. 1.
Figure 3A:
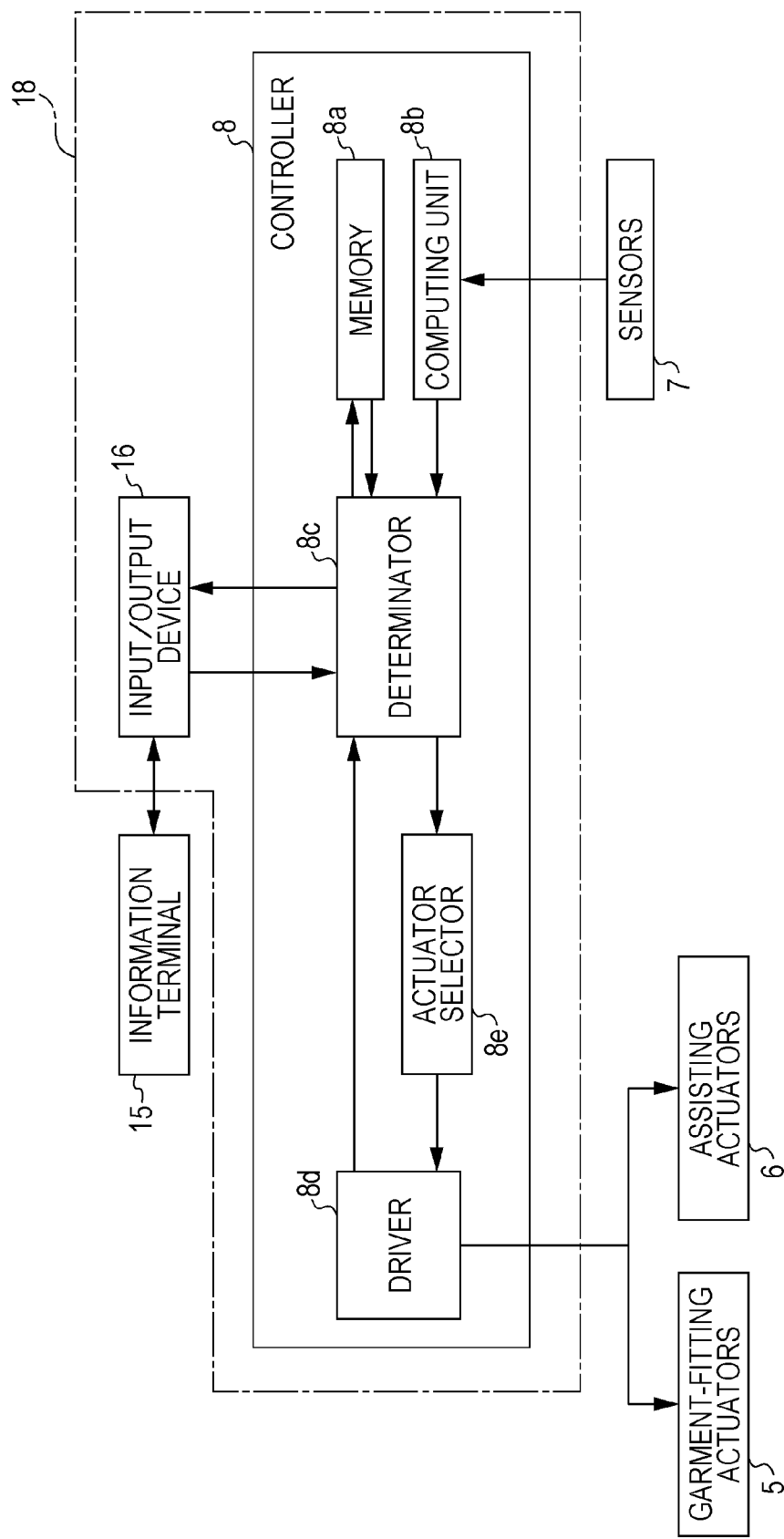
FIG. 3A is a block diagram related to an assist garment.
Figure 4:
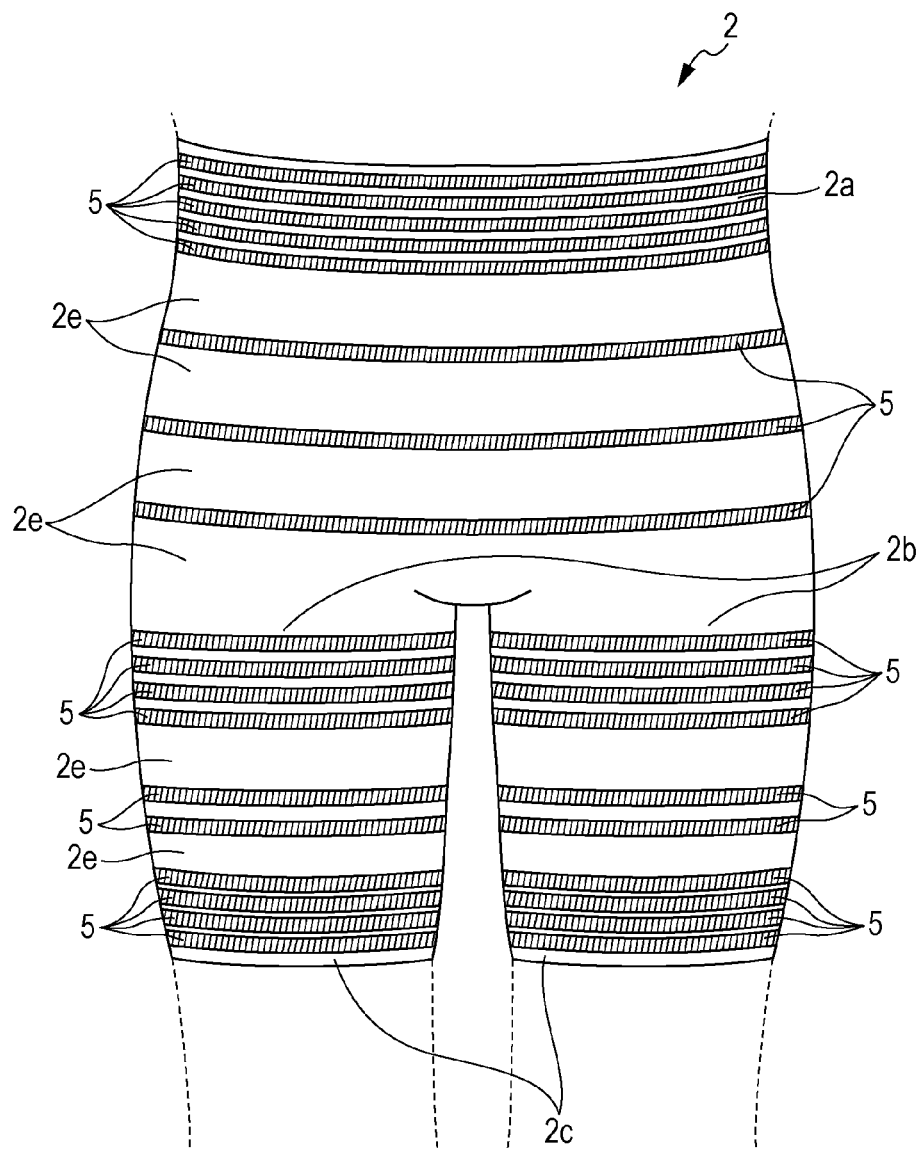
FIG. 4 illustrates garment-fitting actuators when placed on the front surface of an assist garment body.
Figure 5:
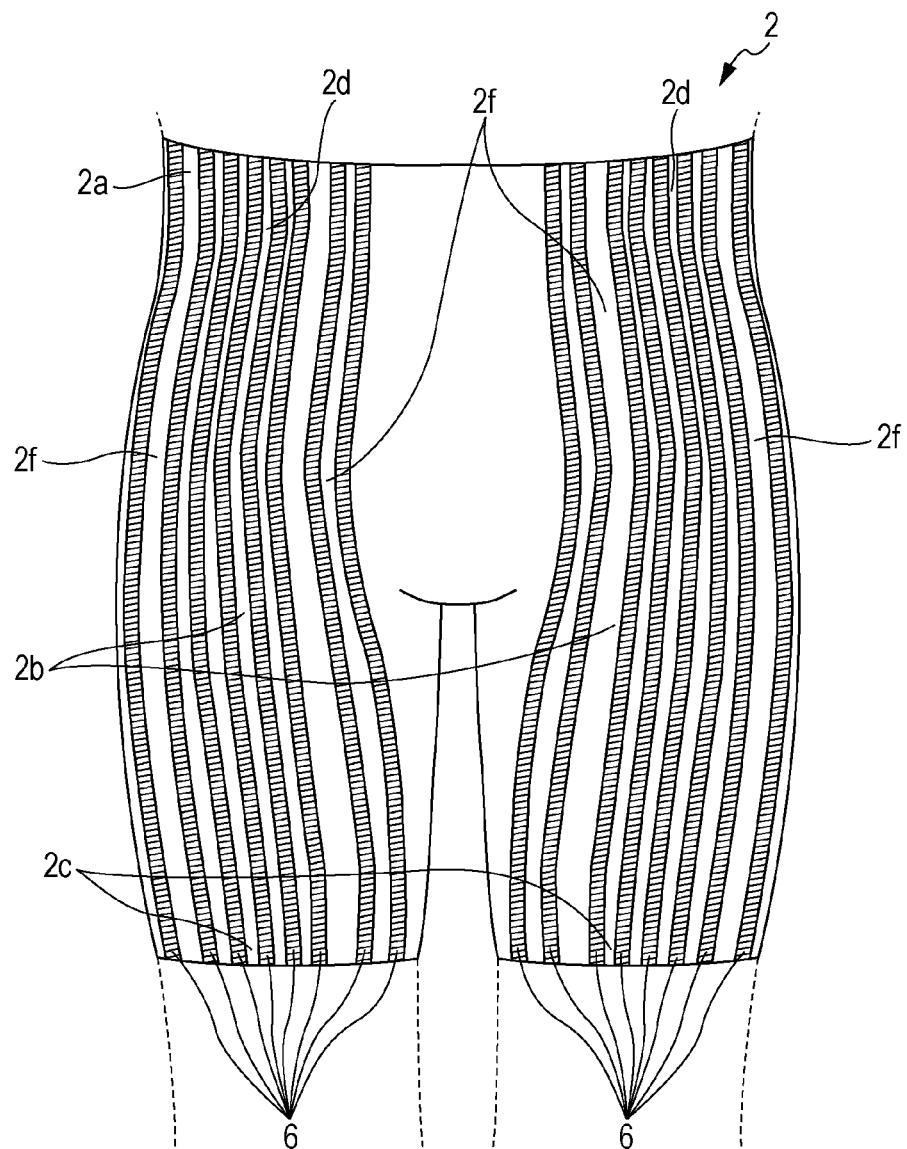
FIG. 5 illustrates assisting actuators when placed on the front surface of a garment body.

FIG. 1 illustrates an assist garment 4 according to a first embodiment of the present disclosure when worn on a user 1. FIG. 2 is a perspective view of the assist garment 4 illustrated in FIG. 1. FIG. 3A is a block diagram related to the assist garment 4. FIG. 3B illustrates comparisons made between actual signals, and signals of various phases (signals of Phases E, F, and G are illustrated as a representative example) stored in a memory 8a to determine that the current state of walking is Phase E within the process (Phases A to G) of walking assist provided by the assist garment 4 described later in FIG. 34. FIG. 3C illustrates signals of Phase E of a time response pattern used for the determination illustrated in FIG. 3B. FIG. 3D illustrates an example of driving of a plurality of assisting actuators 6 (Actuators A to E as a representative example) in Phase E, based on the determination illustrated in FIG. 3B. FIG. 4 illustrates a plurality of garment-fitting actuators 5 when placed on the front surface of a garment body 2. FIG. 5 illustrates the assisting actuators 6 when placed on the front surface of the garment body 2.

As illustrated in FIG. 1, the assist garment 4 according to the first embodiment of the present disclosure at least has the following components placed on the garment body 2: the garment-fitting actuators 5 having a linear shape, the assisting actuators 6 having a linear shape, and a controller 8. The assist garment 4 is worn on a human body which is an example of a living body, for example, on a part of the lower body of the user 1 to be assisted, such as the waist, to assist muscular movement.

The garment-fitting actuators 5 are placed on the garment body 2 linearly along at least one end portion of the garment body 2 such that the garment-fitting actuators 5 cross the assisting actuators 6.

The garment-fitting actuators 5 are driven to contract to allow the fit of the garment body 2 on a part of the user 1 to change from loose to tight. The garment-fitting actuators 5 are driven to extend to allow the fit of the garment body 2 on a part of the user 1 to change from tight to loose.

In one example, when the assist garment 4 is worn on a given part of the user 1, the garment-fitting actuators 5 are placed linearly in the circumferential direction of the part. For example, as illustrated in FIG. 1, the garment-fitting actuators 5 are placed in the circumferential direction of the right thigh, the garment-fitting actuators 5 are placed in the circumferential direction of the left thigh, and the garment-fitting actuators 5 are placed in the circumferential direction of the waist.

The assisting actuators 6, which are placed linearly on the garment body 2, cross the garment-fitting actuators 5. The assisting actuators 6 are placed such that when the garment body 2 is worn on the user 1, the assisting actuators 6 are aligned parallel to the direction of muscular extension and contraction of the user 1. The assisting actuators 6 are driven to extend and contract to assist muscular movement in a part of the body around which the assisting actuators 6 are tightened by the garment-fitting actuators 5. For the garment body 2, for example, the direction of muscular extension and contraction refers to the direction oriented from one end portion of the garment body 2 toward the other end portion.

In this case, in one example, the garment-fitting actuators 5 are placed linearly in the circumferential direction of at least one of one end portion and the other end portion of the garment body 2. In FIG. 4, the garment-fitting actuators 5 are placed in the circumferential direction of both end portions (an upper end portion 2a and a lower end portion 2c) of the garment body 2, and also in the circumferential direction of an area halfway between these end portions (a base portion 2b of the thigh area).

In one example, as illustrated in FIG. 5, the assisting actuators 6 are placed in a direction oriented from the upper end portion 2a corresponding to one end portion of the garment body 2, toward the lower end portion 2c corresponding to the other end portion of the garment body 2.

An end portion of the garment body 2 where the garment-fitting actuators 5 are placed is a linear or band-shaped area to be tightened (target tightening area). If the assist garment 4 is implemented as underpants, this end portion refers to the waist area (upper end portion) or lower end portion. If the assist garment 4 is implemented as a tubular member worn on the arm, this end portion refers to an end portion near the wrist area or the base portion of the arm. If the assist garment 4 is implemented as a tubular member worn on the torso, this end portion refers to the upper or lower end portion. If the assist garment 4 is implemented as a tubular member worn on the hand, this end portion refers to an end portion at the fingertip or the heel of the hand. In short, if the assist garment 4 is implemented as a tubular member worn on a part of the human body, this end portion refers to one end portion along its central axis. In the case of leg assist underpants or torso assist garment, for example, this end portion is the upper end portion of the garment body 2 to ensure that the garment body 2 does not slip from the user 1 before the garment body 2 is tightened by the garment-fitting actuators 5. The garment-fitting actuators 5 may not necessarily be placed in an end portion of the garment body 2. For instance, if the assist garment is an arm up/down motion assist garment that is worn on an area of the body extending across the armpit from the torso to one arm, the garment-fitting actuators 5 may be placed in the base portion of the arm and in a part of the torso across the armpit to allow tightening in the vicinity of the armpit.

The controller 8 independently controls the drive of the garment-fitting actuators 5 and the drive of the assisting actuators 6.

In one more specific example, the assist garment 4 includes a plurality of sensors 7. The sensors 7 may be EMG sensors. Each of the sensors 7 is positioned in direct or indirect contact with the skin of a part of the user 1 to detect a signal of the user 1, and outputs the detected signal to the controller 8. In one example, the sensors 7 are placed at or around the placement positions of the assisting actuators 6 and at or around the placement positions of the garment-fitting actuators 5 to detect whether the assist garment 4 is in contact with the user 1. The sensors 7 may be placed in a region 2g of the part of the user 1 corresponding to a muscle at a density higher than the density at which the sensors 7 are placed in a region other than the region 2g of the part of the user 1 corresponding to a muscle.

The controller 8 controls the drive of the garment-fitting actuators 5 based on an output from each of the sensors 7. That is, when the controller 8 determines that the sensors 7 have not successfully detected a signal from the user 1, the controller 8 determines that the garment body 2 is not fit on the user 1. In this case, the controller 8 controls, for example, a speaker, a display, or a vibrator included in an input/output device 16 to generate an alarm. If the controller 8 determines that the sensors 7 have successfully detected a signal from the user 1, the controller 8 determines that the garment body 2 is fit on the user 1, and waits for a drive start signal for the assisting actuators 6.

That is, the speaker, display, or vibrator of the input/output device 16 functions as an example of a notifier. If the controller 8 determines, based on detections from those of the sensors 7 located at placement positions of the garment-fitting actuators 5 or in areas around the placement positions of the garment-fitting actuators 5, that not all of the placement positions of the garment-fitting actuators 5 or the areas around the placement positions of the garment-fitting actuators 5 are in contact with the user 1, the controller 8 uses the notifier to notify the user 1 wearing the assist garment 4 that the assist garment 4 is not in contact with the user 1.

FIG. 1 and FIGS. 2 to 5 illustrate an example in which the garment body 2 of the assist garment 4 is implemented as underpants. FIG. 1 illustrates the user 1 wearing the garment body 2, with a controller belt 3 incorporating the controller 8 worn around the waist of the user 1. In one example, as illustrated in FIG. 2, a plurality of EMG sensors as an example of the sensors 7, and the assisting actuators 6 are secured to the garment body 2 at predetermined intervals in the vertical direction of the underpants, in other words, in the axial direction of the body of the user 1 (the top-bottom direction in FIG. 2) (see FIG. 5). That is, sensor wiring 9 connected with the sensors 7, and the assisting actuators 6 are placed alternately. The garment-fitting actuators 5 are secured to the garment body 2 at predetermined intervals in the lateral direction of the underpants, in other words, in a direction orthogonal to the axial direction of the human body (the top-bottom direction in FIG. 2) (see FIG. 4). Although the sensors 7 and the sensor wiring 9 for the sensors 7 are indicated by solid lines in FIG. 2, a detailed description of an exemplary structure of the garment body will be given later with reference to, for example, FIGS. 23 to 26.

In one specific example, as illustrated in FIG. 4, the density at which the garment-fitting actuators 5 are placed in end portions along the axis of the garment body 2, for example, the upper end portion 2a of the garment body 2 corresponding to the waist area, the base portion 2b of the thigh area, and the lower end portion 2c of the garment body 2, is higher than the density at which the garment-fitting actuators 5 are placed in a portion 2e other than the end portions 2a to 2c (the upper end portion 2a, the base portion 2b of the thigh area, and the lower end portion 2c). This is to ensure a tight, secure fit of the garment body 2 onto the user 1 in the upper end portion 2a, the base portion 2b of the thigh area, and the lower end portion 2c. That is, activating or deactivating the garment-fitting actuators 5 to contract or extend in the upper end portion 2a of the garment body 2, the base portion 2b of the thigh area, and the lower end portion 2c of the garment body 2 causes the garment body 2 to change between a tightened state in which the garment body 2 is tightly secured to the user 1, and a loosened state in which this tight securing is released. This configuration allows the garment-fitting actuators 5 to securely tighten the end portions 2a, 2b, and 2c, which are relatively important areas in causing the force generated by the assisting actuators 6 to act on the user 1, onto the user 1. This secure tightening allows the assist force from the assisting actuators 6 to be more properly exerted on, for example, the muscles of the user 1. The garment-fitting actuators 5 also tighten the portion 2e of the garment body 2 other than the end portions 2a to 2c onto the user 1 to minimize slack in the garment body 2. This allows for more reliable contact of the sensors 7 with the user 1 also in the portion 2e of the garment body 2 other than the end portions 2a to 2c.

In one specific example, as illustrated in FIG. 5, the density of the assisting actuators 6 placed in a portion 2d on the front of the garment body 2 running from the middle of the front of the thigh area to the waist area, and in a portion on the back of the garment body 2 running from the middle of the back of the thigh area to the waist area and corresponding to the portion 2d running from the middle of the front of the thigh area to the waist area, is higher than the density of the assisting actuators 6 placed in a portion 2f of the garment body 2 other than the portion 2d and the portion corresponding to the portion 2d. This is to facilitate exertion of the assist force from the assisting actuators 6 on the muscles (muscles 1b in FIG. 6) in the thigh area. In this way, the garment-fitting actuators 5 and the assisting actuators 6 are placed at different positions at varying densities depending on their intended functions, in other words, in a manner that allows the garment-fitting actuators 5 and the assisting actuators 6 to effectively exert their intended functions.

Actuators

Although the actuator used for each of the garment-fitting actuators 5 having a linear shape and the actuator used for each of the assisting actuators 6 having a linear shape are the same, different actuators may be used for the garment-fitting actuator 5 and the assisting actuator 6.

In the first embodiment, actuators of the same structure are used as the garment-fitting actuator 5 having a linear shape and the assisting actuator 6 having a linear shape.

Figure 8:
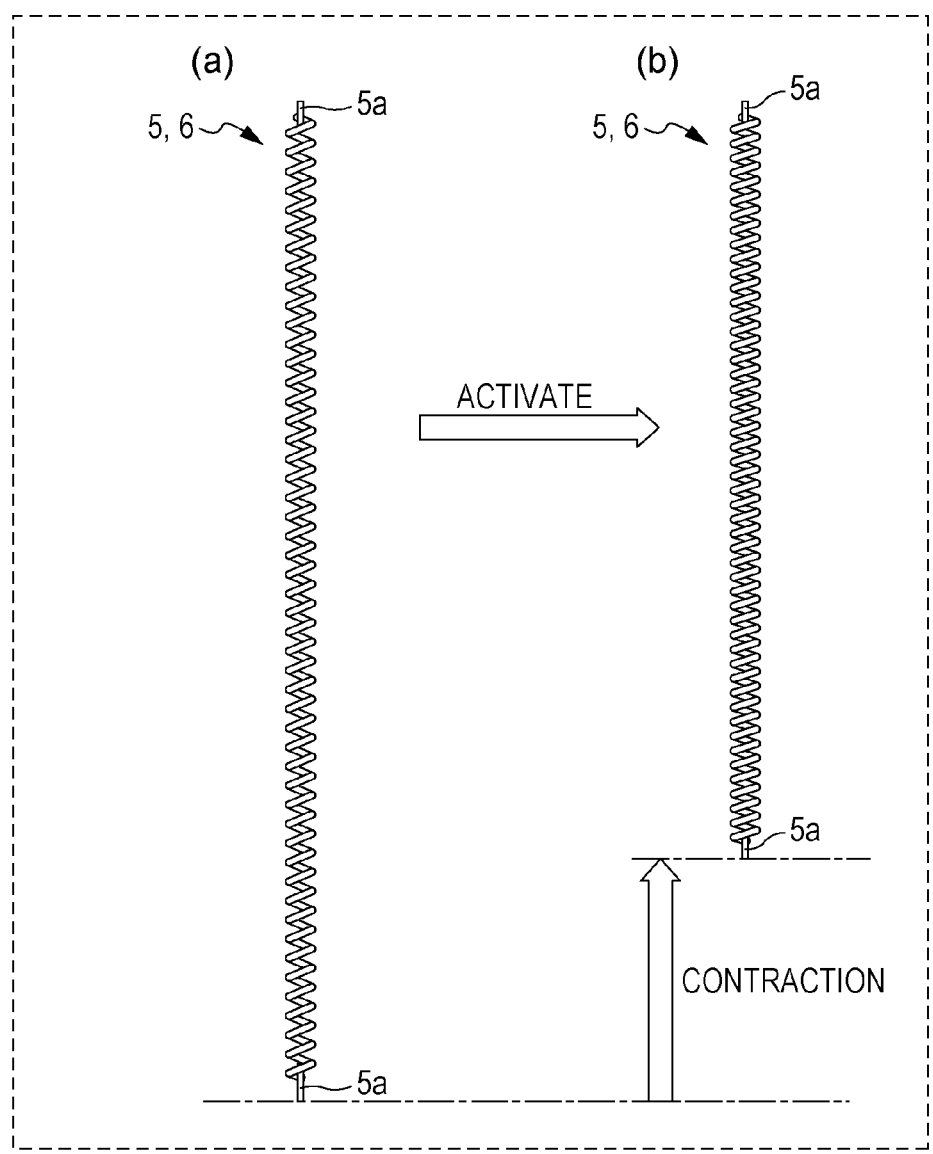
FIG. 8 illustrates an actuator.
Figure 9:
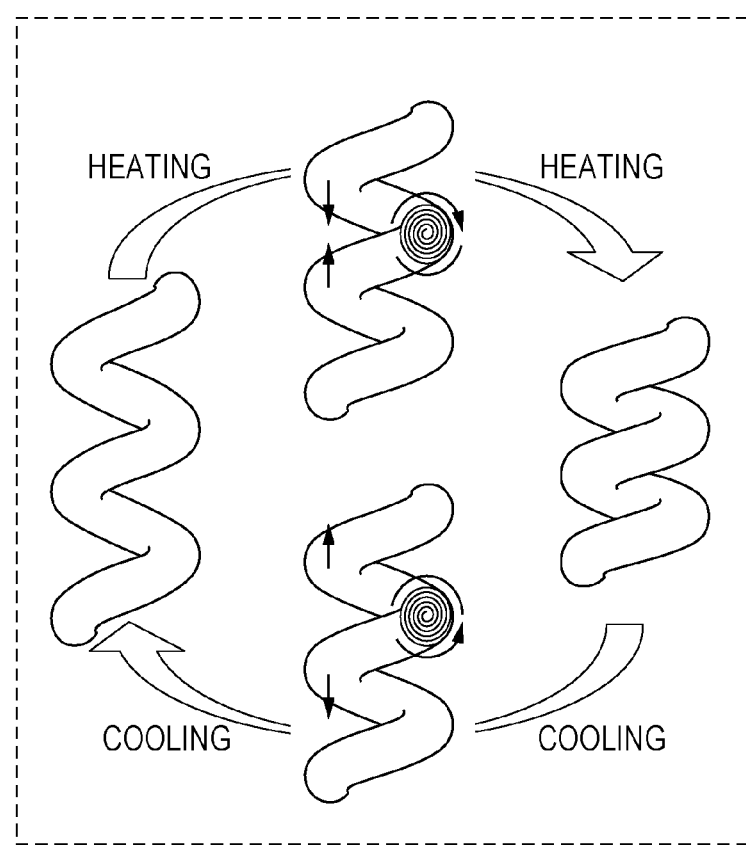
FIG. 9 illustrates an actuator illustrated in FIG. 8 in enlarged view.
Figure 10:
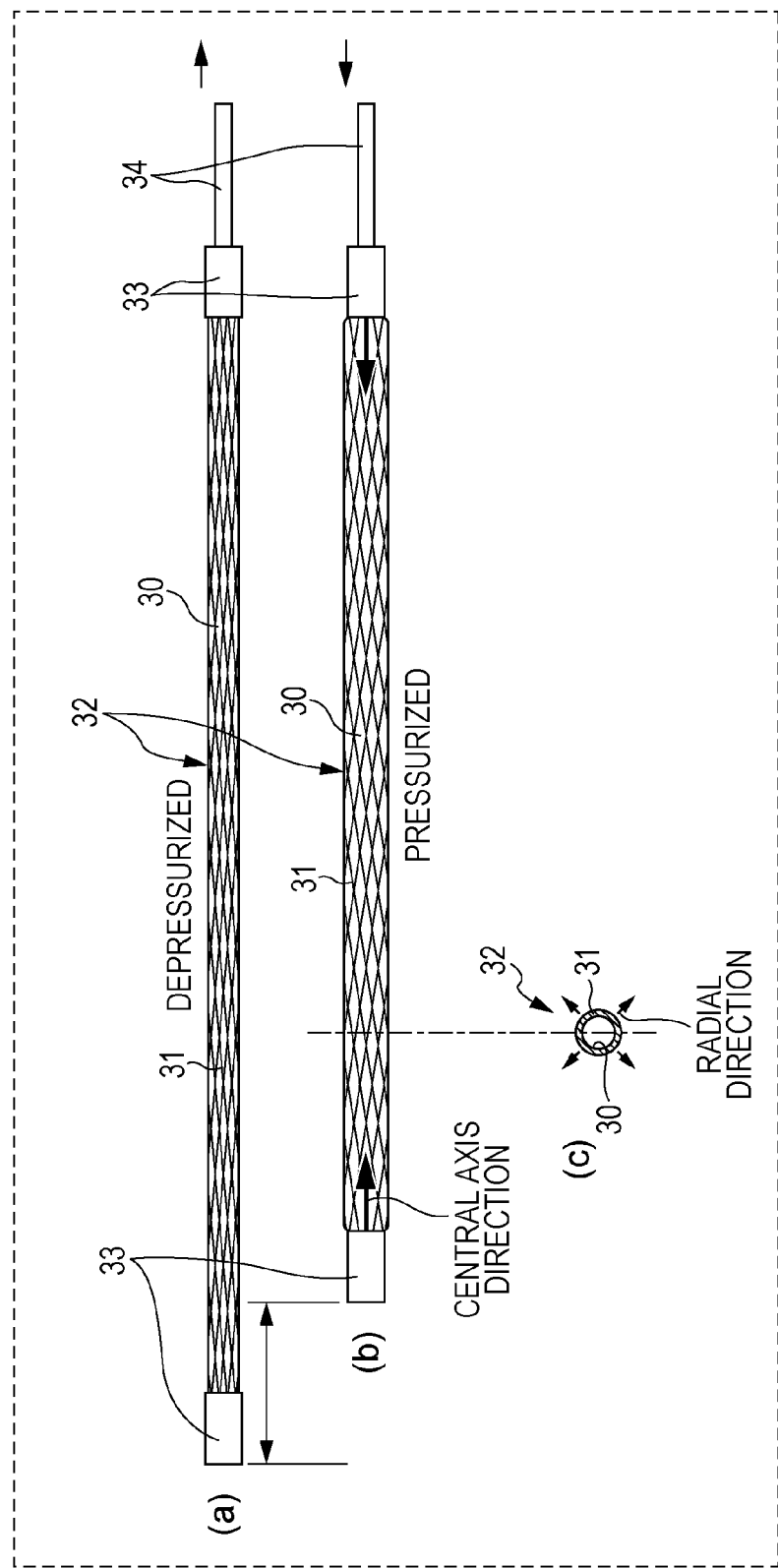
FIG. 10 illustrates another actuator.
Figure 11:
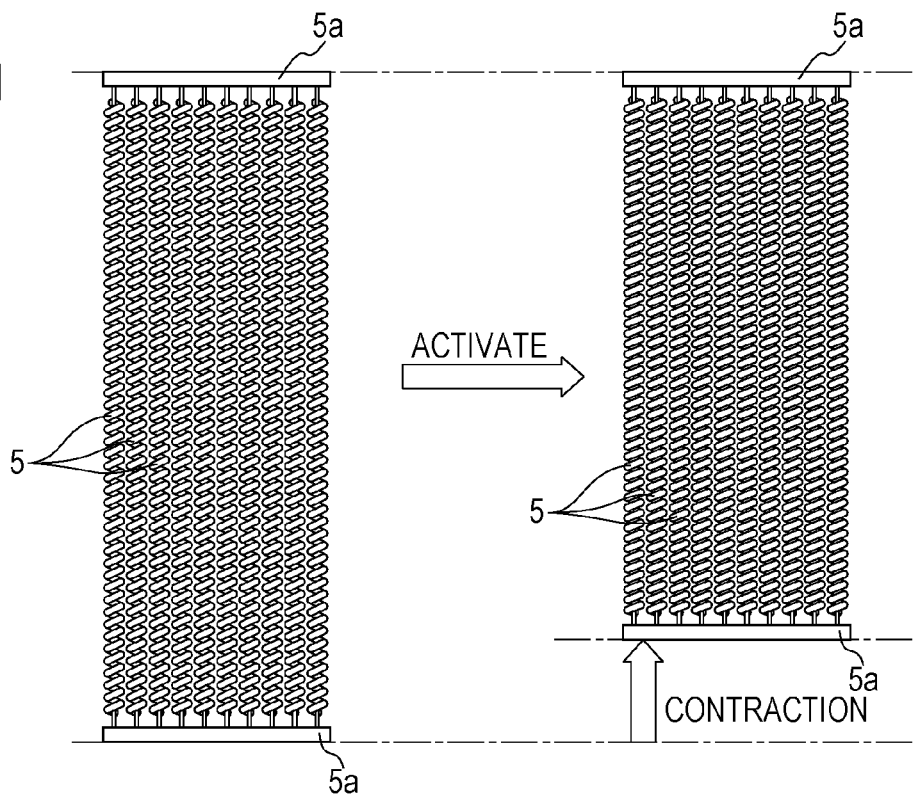
FIG. 11 illustrates actuators according to a modification.
Figure 12:
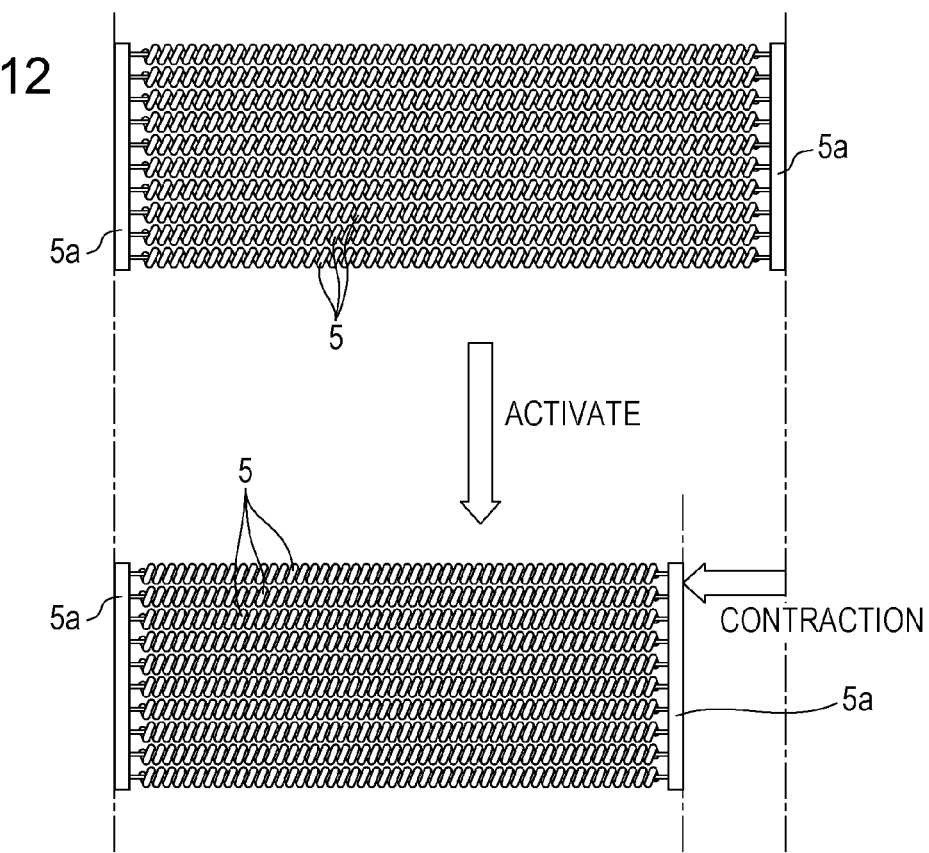
FIG. 12 illustrates actuators according to a modification.
Figure 13:
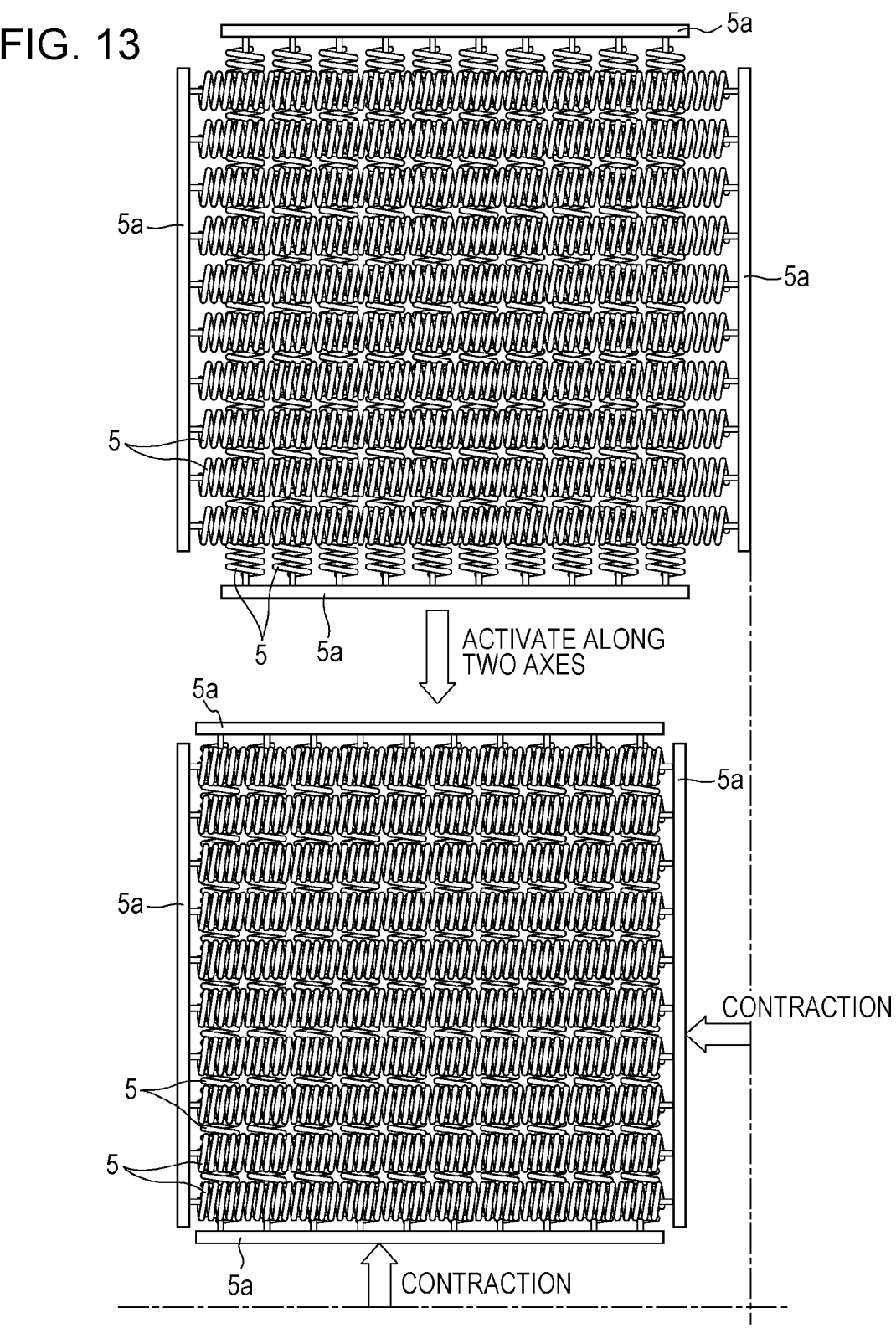
FIG. 13 illustrates actuators according to a modification.

FIG. 8 illustrates an actuator used as each of the garment-fitting actuator 5 and the assisting actuator 6. FIG. 9 illustrates an actuator used as each of the garment-fitting actuator 5 and the assisting actuator 6. FIG. 10 illustrates another actuator. FIGS. 11 to 13 illustrate actuators according to various modifications. As illustrated in FIG. 8(*a*), in one example, each actuator is formed by a linear member of synthetic resin of 0.233 mm in diameter wound in a helical form. When energized and heated upon application of voltage to an electrode 5a at each end, the actuator contracts along its entire length as illustrated in FIG. 8(b). When de-energized and cooled by natural heat radiation, the actuator extends back to its original length. This is because heating causes the helically twisted linear member made of resin to twist circumferentially as illustrated in FIG. 9, causing contraction along its entire length. As the actuator is cooled by, for example, natural heat radiation, the twist is released circumferentially, causing the actuator to extend along its entire length. Each actuator may be actuated singly. Alternatively, depending on the magnitude of the force to be exerted, a large number of actuators may be arranged in parallel so as to be extended and contracted concurrently as illustrated in FIGS. 11 and 12. In another alternative, a large number of actuators may be arranged in parallel in two mutually orthogonal directions so as to be extended and contracted concurrently in the two mutually orthogonal directions as illustrated in FIG. 13.

Examples of such an actuator may include a linearly-shaped actuator that is caused to contract by application of heat, specifically, a polymer actuator that is linearly shaped and capable of axial extension and contraction. More specifically, such an actuator may be in the form of a coil made by twisting nylon fibers with a silver surface coating. When this actuator in the form of a coil is energized and heated by application of current to the silver coating, a torque is produced, causing the actuator to contract, and when the applied current is released, this actuator extends back to its original shape. Such an actuator is easy to drive, and allows for increased output per unit weight.

Another example of such an actuator may be a linearly-shaped pneumatic actuator illustrated in FIG. 10 that is caused to extend and contract by adjustment of air pressure. An example of this pneumatic actuator may be a McKibben actuator 32 that has a flange 33 secured at each end of a rubber tube 30, with a fiber mesh 31 wound around the outer circumference of the rubber tube 30. The McKibben actuator 32 operates as follows. That is, when a fluid (for example, air) is introduced from tubing 34 into the rubber tube 30 through the flange 33 at one end, the rubber tube 30 is pressurized to expand. At this time, the fiber mesh 31 constrains the rubber tube 30 to expand radially (see FIG. 10(c)) but contract greatly along the central axis of the rubber tube 30 (see FIG. 10(b)). When a fluid (for example, air) is discharged from the inside of the rubber tube 30 from the tubing 34 through the flange 33 at one end, the rubber tube 30 is depressurized, causing the rubber tube 30 to contract radially (see FIG. 10(c)) together with the fiber mesh 31 but extend greatly along the central axis of the rubber tube 30. As a specific example of the McKibben actuator 32, a McKibben actuator with an outside diameter of 1.2 mm has already been developed. Such an actuator may be easily allowed to retain its position by blocking entry and exit of fluid into and from the rubber tube 30.

The garment-fitting actuators 5 are placed in a direction crossing (for example, orthogonal to) the axial direction of a part of the user 1 to exert a force that brings the assisting actuators 6 into contact with the user 1. The garment-fitting actuators 5 are placed at least in both axial end portions of the garment body 2 to tightly secure the garment body 2 onto the user 1 in both axial end portions. In one example, if the garment body 2 is implemented as underpants, the garment-fitting actuators 5 are also placed in areas such as the groin to tightly secure the garment body 2 onto the user 1. For example, when the garment body 2 is to be donned on the user 1 across a joint, the garment-fitting actuators 5 are also placed in areas on both sides of the joint to tightly secure the garment body 2 onto the user 1. The garment-fitting actuators 5 are activated to remove looseness in the garment body 2 to provide a tight fit. Removing looseness in the garment body 2 to provide a tight fit may be interpreted as adjusting the size of the garment body 2 for the user 1. That is, activating the garment-fitting actuators 5 to tighten the garment body 2 onto the user 1 makes it possible to remove differences in how tightly the garment body 2 fits to the user 1 depending on the size of the garment body 2 or the body shape of the user 1. Prior to donning of the garment body 2, the garment-fitting actuators 5 are in a non-activated state to keep a loose fit for easy wearing. Once the garment body 2 is donned, the garment-fitting actuators 5 are activated to tighten up the garment body 2 so that the garment body 2 is tightly secured onto the user 1 together with the assisting actuators 6. This allows for reliable and more proper transmission of the assist force from the assisting actuators 6 to the muscles 1b. For doffing of the garment body 2, the garment-fitting actuators 5 are deactivated to loosen up the garment body 2 again for easy removal.

Although the assisting actuators 6 are placed in the axial direction of a part of the user 1 (in other words, in the axial direction of muscles in the part) in the above-mentioned example, this is not to be construed restrictively. Alternatively, the assisting actuators 6 may be placed in a direction crossing (for example, in any crossing direction such as a direction orthogonal or oblique to) the axial direction of the part. In one example, the assisting actuators 6 may be extended and contracted along with movement of the muscles 1b illustrated in FIG. 6 to assist the movement of the muscles 1b.

Sensors

Each of the sensors 7 is, for example, an electromyogram (EMG) sensor that measures an EMG, which represents a voltage generated when a muscle is moved, as an example of a biosignal. EMG sensors are able to detect commands sent to the muscles from the brain, and thus use of EMG sensors improves the capability of the assist to follow muscle movement. The sensor 7 used is, however, not limited to an EMG sensor but may be, for example, a strain sensor, an acceleration sensor, or a Gyro sensor. Although described later in detail, using an EMG sensor as the sensor 7 has an additional advantage of enabling detection of wrinkles 39 during fitting operation.

Figure 6:
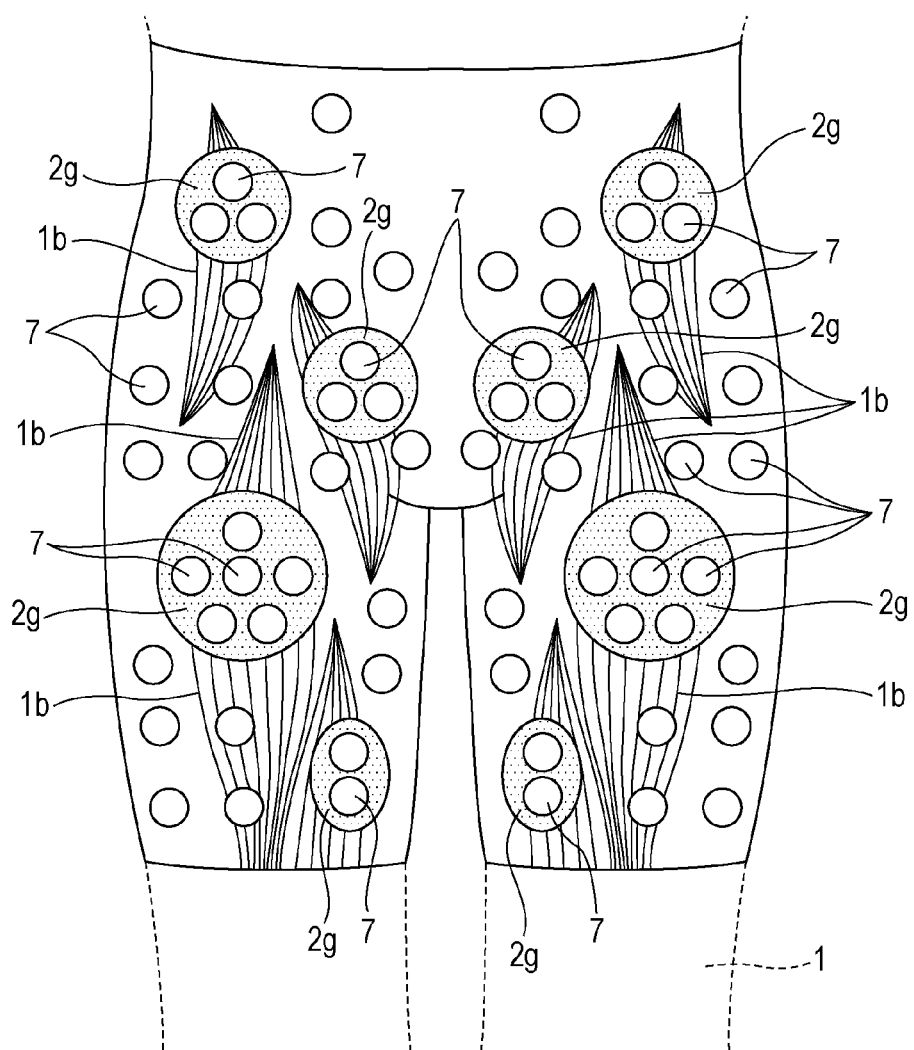
FIG. 6 illustrates placement of sensors on the front surface of a garment body in relation to muscles.
Figure 7:
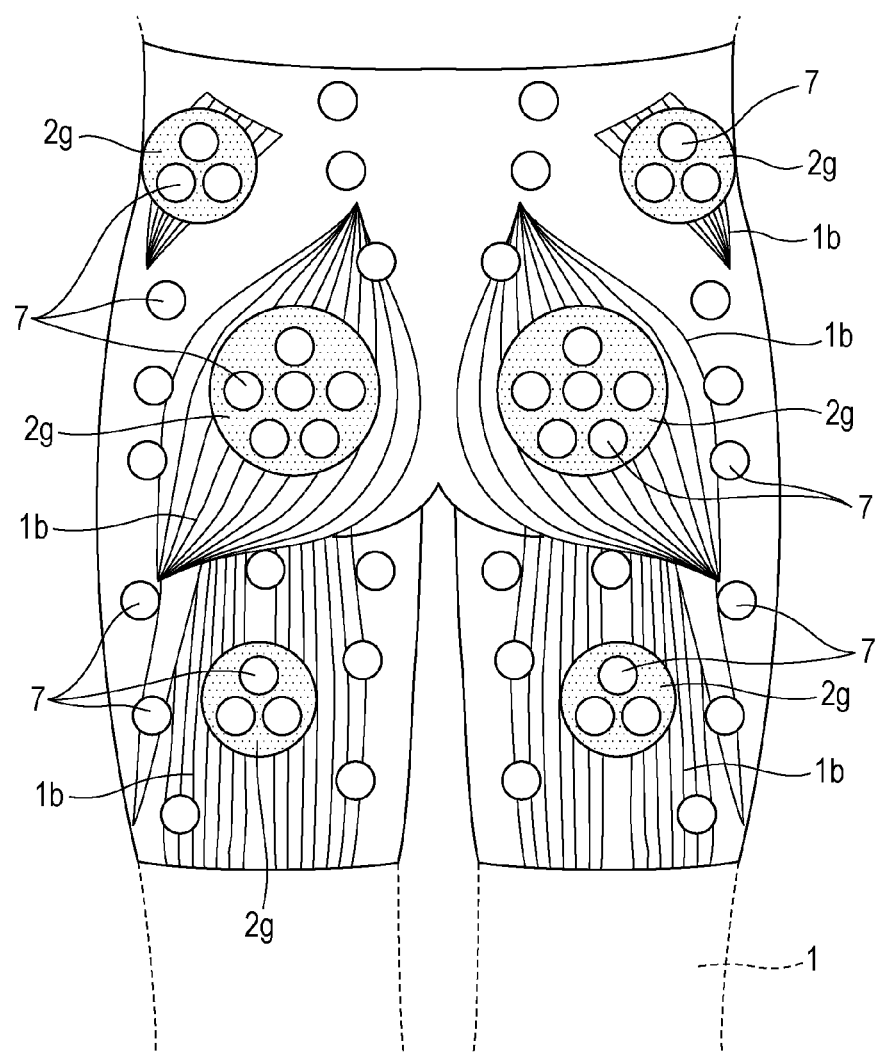
FIG. 7 illustrates placement of sensors on the back surface of a garment body in relation to muscles.
Figure 14:
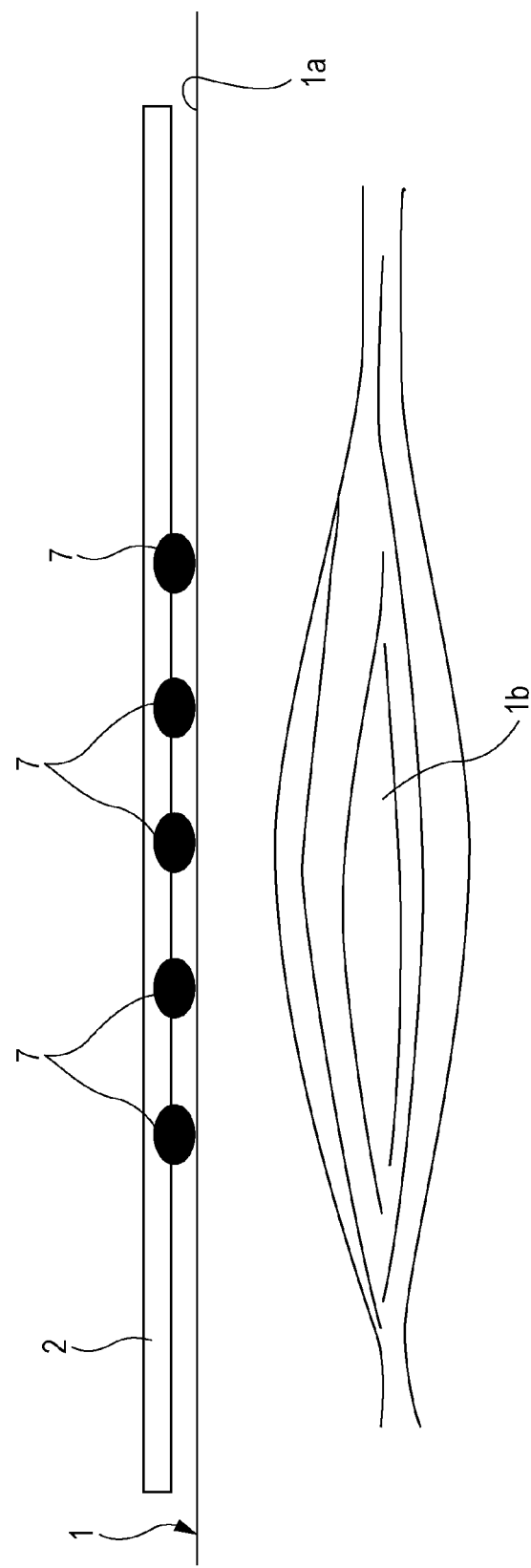
FIG. 14 illustrates the relationship between sensor placement and a muscle.

FIG. 14 illustrates the relationship between placement of the sensors 7 and the muscle 1b. Each of the sensors 7 may be placed at a position that allows measurement of the movement of the corresponding muscle 1b. For example, in an area corresponding to the muscle 1b, the sensor 7 may be placed at a position corresponding to the position of greatest muscle movement to facilitate detection of movement of the muscle 1b by the sensor 7. In one specific example, as illustrated in FIGS. 6 and 7, one or more sensors 7 are placed in the region 2g on both the front and back surfaces of the garment body 2 corresponding to the muscle 1b to facilitate measurement of the movement of the muscle 1b by the sensors 7. In a more specific example, on the front surface of the garment body 2, each of the sensors 7 is placed at a position corresponding to a femoral muscle such as a rectus femoris muscle or in the region 2g. On the back surface of the garment body 2, each of the sensors 7 is placed at a position corresponding to a muscle in the buttock, such as the gluteus maximus muscle, and the hamstring, such as the biceps femoris, or in the region 2g.

Figure 15:
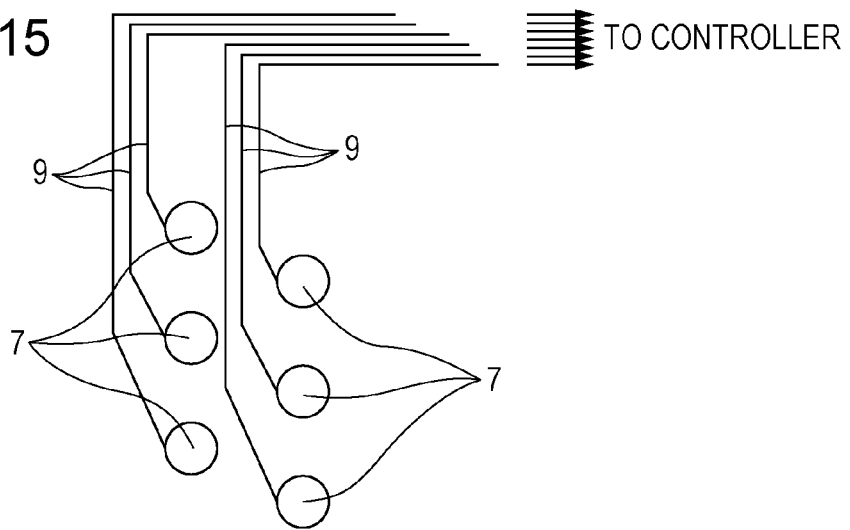
FIG. 15 illustrates the wiring from each sensor for analog wiring.
Figure 16:
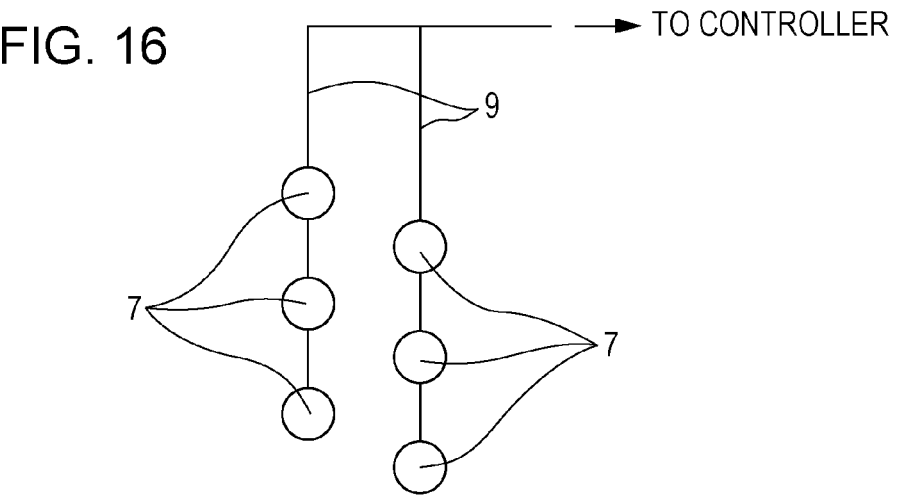
FIG. 16 illustrates the wiring from each sensor for digital wiring.

For analog wiring, the sensor wiring 9 from each of the sensors 7 is routed as illustrated in FIG. 15. This configuration allows a signal to be detected from each of the sensors 7 independently. For digital wiring, the sensor wiring 9 from each of the sensors 7 is configured as common wiring using a digital communication bus as illustrated in FIG. 16. This configuration allows for reduced number of wires.

Another example of the sensor 7 includes an axial-force sensor 7A and a perpendicular-force sensor 7B that are used to detect a fit.

Figure 17:
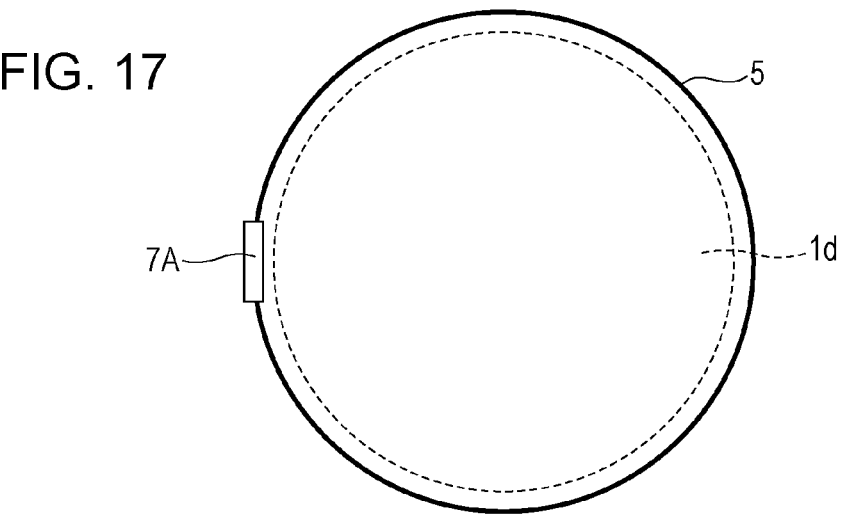
FIG. 17 illustrates, in sectional view, attachment of an axial-force sensor to a user.
Figure 18:
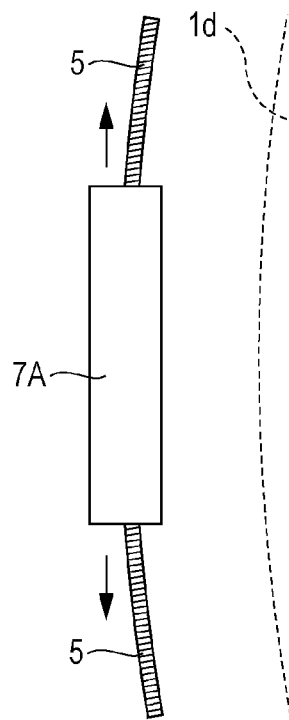
FIG. 18 is an enlargement of the sensor of FIG. 17, illustrating, in sectional view, attachment of an axial-force sensor to a user.
Figure 19:
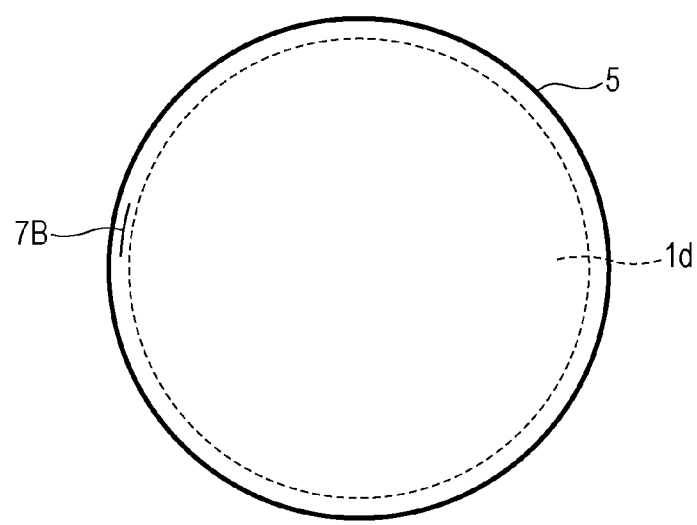
FIG. 19 illustrates, in sectional view, attachment of a perpendicular-force sensor to a user.

FIG. 17, and expanded in FIG. 18, illustrate in sectional view, the attachment of the axial-force sensor 7A to the user 1. FIG. 19, and expanded in FIG. 20, illustrate in sectional view, the attachment of the perpendicular-force sensor 7B to the user 1.

As illustrated in FIGS. 17 and 18, when the axial-force sensor 7A is to be mounted on a leg 1d of the user 1, the axial-force sensor 7A is secured to the midsection of the garment-fitting actuator 5 to allow the axial-force sensor 7A to directly measure (detect) the force generated by extension or contraction of the garment-fitting actuator 5. The plane indicated at 1d in FIG. 17 represents the cross-section of the leg.

Figure 20:
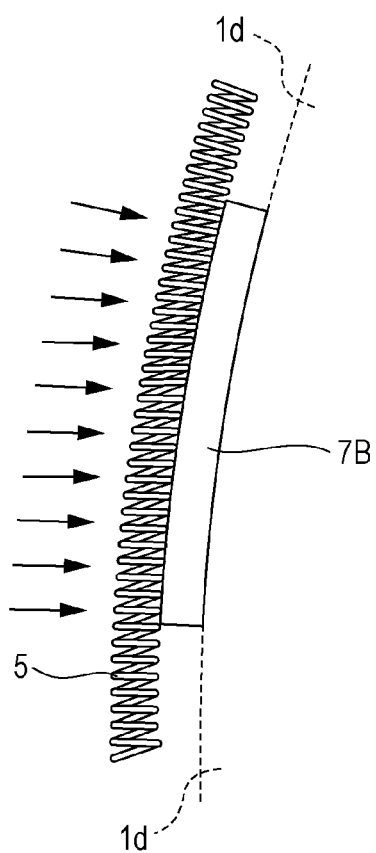
FIG. 20 is an enlargement of the sensor of FIG. 18, illustrating, in sectional view, attachment of a perpendicular-force sensor to a user.

As illustrated in FIGS. 19 and 20, when the perpendicular-force sensor 7B is to be mounted on the leg 1d of the user 1, the perpendicular-force sensor 7B is placed on the user-side surface of the garment-fitting actuator 5 such that the perpendicular-force sensor 7B is in contact with the user 1. This configuration allows the perpendicular-force sensor 7B to measure (detect) the perpendicular force that acts on the user 1 as the garment-fitting actuator 5 extends or contracts. The plane indicated at 1d in FIG. 19 represents the cross-section of the leg.

The force detected by the sensor 7, for example, the axial-force sensor 7A or the perpendicular-force sensor 7B, are output to the controller 8 and used to control the extension and contraction of the garment-fitting actuator 5.

Figure 21:
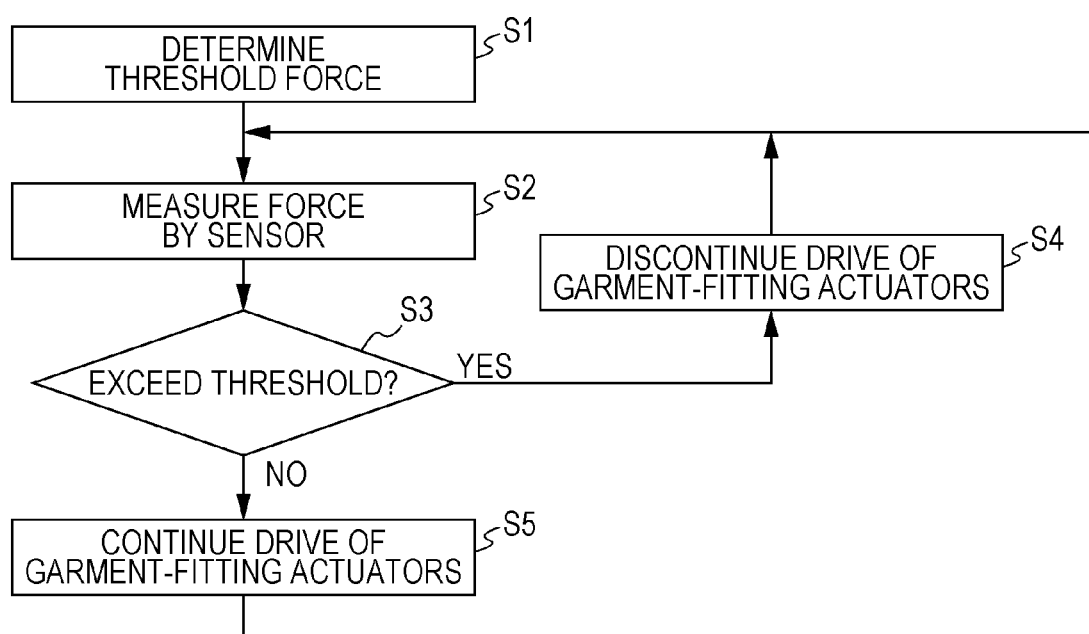
FIG. 21 is a flowchart illustrating how a controller controls the force exerted by garment-fitting actuators based on sensor output.

FIG. 21 is a flowchart illustrating how the controller 8 controls the force exerted by the garment-fitting actuator 5 based on sensor output, for example.

As illustrated in FIG. 21, first, in step S1, the controller 8 determines a threshold force. This threshold force is set by taking into account factors such as sufficient pressing force for enabling signal detection by the sensor 7 and sufficient pressure for reducing unwanted lifting of the assisting actuator 6 or slippage of end portions.

Next, in step S2, a force is detected by the sensor 7, and the detected force is output to the controller 8. If no force is detected by the sensor 7, the processing waits until the sensor 7 detects a force.

Next, in step S3, the controller 8 determines whether the force detected in step S2 exceeds the threshold determined in step S1. If the controller 8 determines that the force detected in step S2 exceeds the threshold determined in step S1, the processing proceeds to step S4. In step S4, the controller 8 discontinues the drive of the garment-fitting actuator 5, and then the processing returns to step S2. If the controller 8 determines that the force detected in step S2 does not exceed the threshold determined in step S1, the processing proceeds to S5, and the drive of the garment-fitting actuator 5 is continued. Then, the processing returns to step S2.

In this way, the drive of the garment-fitting actuator 5 is controlled by the controller 8 based on an output from the sensor 7. This configuration ensures that the garment-fitting actuator 5 does not exert an excessive tightening force on the user 1 during fitting of the garment body 2 onto the user 1, thus allowing safe use while ensuring for proper tightening and untightening.

Figure 22:
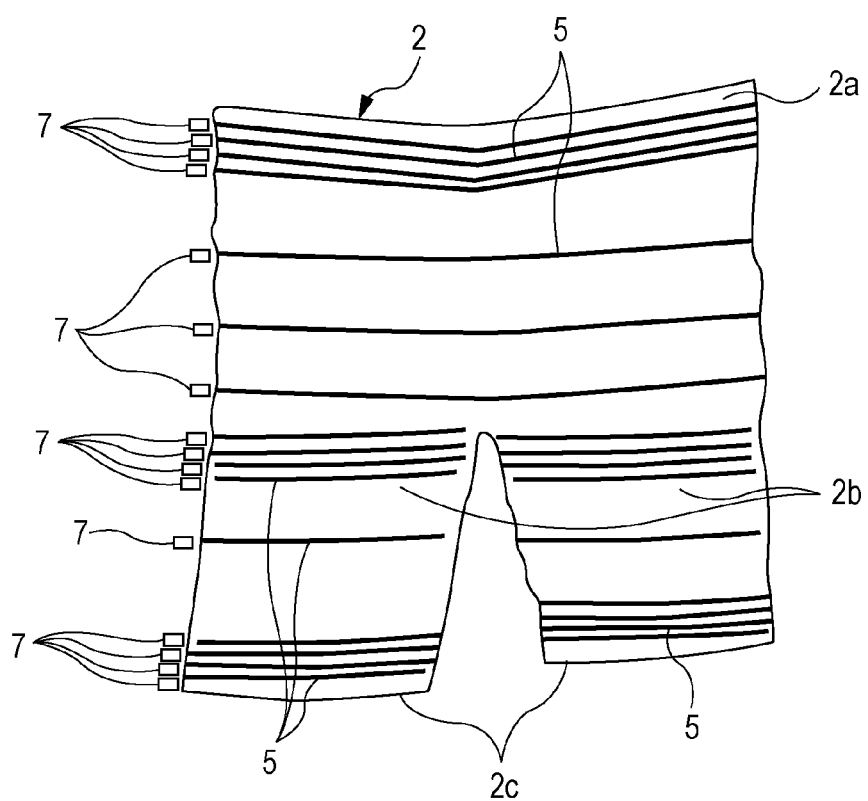
FIG. 22 illustrates specific sensor placement locations.

A specific example of the placement of the sensors 7 is illustrated in FIG. 22. As illustrated in FIG. 22, each of the sensors 7 (for example, the axial-force sensor 7A or the perpendicular-force sensor 7B) may be placed on the corresponding garment-fitting actuator 5 placed in each of areas including the upper end portion 2a of the garment body 2, the base portion 2b of the thigh area, the lower end portion 2c of the garment body 2, and the portion 2e, which is a portion of the garment body 2 excluding the upper end portion 2a, the base portion 2b of the thigh area, and the lower end portion 2c, so that the sensor 7 exerts the function mentioned above.

The sensor wiring 9 is concentrated in the waist area corresponding to the upper end portion of the underpants. The concentrated sensor wiring 9 is connected to the controller belt 3 that is ring-shaped.

If the assisting actuator 6 is an actuator as illustrated in FIG. 8, wires used for energizing and heating the assisting actuator 6 are concentrated in the waist area corresponding to the upper end portion of the underpants, and the concentrated wires are connected to the controller belt 3 that is ring-shaped.

If the garment-fitting actuator 5 is an actuator as illustrated in FIG. 8, wires used for energizing and heating the garment-fitting actuator 5 are concentrated in the waist area (not illustrated) corresponding to the upper end portion of the underpants, and the concentrated wires are connected to the controller belt 3 that is ring-shaped.

If the assisting actuator 6 is an actuator as illustrated in FIG. 10, the tubing running to the assisting actuator 6 is concentrated in the waist area corresponding to the upper end portion of the underpants, and the concentrated tubing is connected to the controller belt 3 that is ring-shaped.

If the garment-fitting actuator 5 is an actuator as illustrated in FIG. 10, the tubing running to the garment-fitting actuator 5 is concentrated in the waist area (not illustrated) corresponding to the upper end portion of the underpants, and the concentrated tubing is connected to the controller belt 3 that is ring-shaped.

The controller belt 3 has engagement sections 3a at both ends. This allows the controller belt 3 to be worn around the waist area of the user 1 by wrapping the controller belt 3 around the waist area and then bringing the engagement sections 3a into engagement with each other. The engagement sections 3a may each be provided with a switch such that upon engagement of the engagement sections 3a, a start signal for the garment-fitting actuator 5 is input to the controller 8. Alternatively, a start signal for the garment-fitting actuators 5 may be input to the controller 8 by the user from the input/output device 16 described later.

The controller belt 3 includes an operating device 18. As illustrated in FIG. 3A, the operating device 18 includes the input/output device 16, and the controller 8 connected to the input/output device 16. The input/output device 16 is capable of communicating with an information terminal 15 such as a smartphone, and has components such as an operating button, a speaker, an LED, a display, and a radio communication unit. The input/output device 16 may not include a radio communication unit for communicating with the information terminal 15 such as a smartphone but may directly accept an input made with the input/output device 16. For example, the user 1 either inputs an instruction to start the assist either directly to the input/output device 16, or inputs the instruction indirectly to the input/output device 16 via the information terminal 15, so that the drive of the garment-fitting actuator 5 and the drive of the assisting actuators 6 are individually controlled by the controller 8.

The input/output device 16 receives inputs of instructions in the form of signals such as fitting operation (activation of the garment-fitting actuators 5) start and end signals, assist operation (activation of the assisting actuators 6) start and end signals, and a wrinkle-countermeasure completion signal. These instructions are transmitted to the controller 8. The fitting operation (activation of the garment-fitting actuators 5) start and end signals may be automatically input respectively upon engagement and disengagement of the engagement sections 3a of the controller belt 3. Alternatively, in response to an instruction to generate an alarm received from the controller 8, the input/output device 16 may perform an alarm operation (for example, generation of an alarm sound from the speaker, display of an alarm on the display, or generation of alarm vibrations by the vibrator).

A smartphone as an example of the information terminal 15 receives, for example, the following instructions from the user 1 that is an example of the human body: a fitting operation (activation of the garment-fitting actuators 5) start instruction, a fitting operation (activation of the garment-fitting actuators 5) end instruction, an assist operation (activation of the assisting actuators 6) start instruction, and assist operation (activation of the assisting actuators 6) end instruction, and a wrinkle-countermeasure completion instruction. These instructions input to the information terminal 15 are transmitted from the information terminal 15 to the controller 8 via the input/output device 16.

The information terminal 15 may perform the above-mentioned alarm operation in response to an instruction to generate an alarm received from the controller 8.

The controller 8 includes a memory 8a, a computing unit 8b, a determinator 8c, an actuator selector 8e, and a driver 8d. The controller 8 controls the drive of the garment-fitting actuators 5 and the drive of the assisting actuators 6 based on signals obtained from the sensors 7, in accordance with instructions received from the input/output device 16.

The memory 8a stores thresholds (such as a first threshold, a second threshold, and an error detection threshold) used for making various determinations associated with the tightening of the garment. The memory 8a also stores, for example, a plurality of assist operation modes that differ in terms of, for example, the magnitude of the assist force provided or the timing when the assist is provided, or a single assist operation mode. Examples of such assist operation modes include a walking mode and a stair climbing/descending mode. The memory 8a stores, for each assist operation mode, a variation pattern corresponding to the time variation of the values of the sensors 7 computed by the computing unit 8b. The memory 8a also stores, for example, a program used by the determinator 8c to determine how to operate the assisting actuators 6. Further, the memory 8a also stores the following pieces of information in advance: positional information on the individual sensors 7, positional information on the garment-fitting actuators 5 corresponding to the individual sensors 7, and positional information on the assisting actuators 6 corresponding to the individual sensors 7.

The computing unit 8b performs computations for sensor calibration as required. Examples of such computations include extracting the strongest signal or a relatively strong signal from a plurality of output signals obtained from the sensors 7, and weighting a plurality of output signals from the sensors 7 and then averaging the weighted signals. Alternatively, the computing unit 8b may perform computations for, for example, gain control, filtering, averaging, rectification or noise cancellation for the output signals of the sensors 7. An example of a sequence of computations that may be performed by 8b is high pass and low pass filtering of the output signal of sensor 7, calculating the absolute value, and then applying an RMS filter. The results of computations in the computing unit 8b are transmitted from the computing unit 8b to the determinator 8c.

For tightening of the garment, the determinator 8c compares the value of the sensor 7 computed by the computing unit 8b with a threshold read from the memory 8a to determine which one is larger or smaller than the other. If the sensor 7 is the axial-force sensor 7A or the perpendicular-force sensor 7B, the determinator 8c determines how to operate the garment-fitting actuators 5 based on whether the tightening force exceeds the first threshold or the second threshold, and transmits an instruction to the actuator selector 8e as required. If the sensor 7 is an EMG sensor, the determinator 8c detects wrinkles based on whether a detected potential exceeds the error detection threshold, and based on the detection result, the determinator 8c determines how to operate the garment-fitting actuators 5. The determinator 8c then transmits, as required, an instruction to the actuator selector 8e, or transmits, as required, an instruction to generate an alarm to the operating device 18.

In assist phase (when the assisting actuators 6 are activated), the determinator 8c compares the time variation of the output value of the sensor 7 computed by the computing unit 8b, with variation patterns of the output of the sensor 7 corresponding to individual assist operation modes read from the memory 8a, to determine the motion or state of the user. The determinator 8c also determines, based on a program or the like stored in the memory 8a in advance, how to operate the assisting actuators 6, and transmits an instruction to the actuator selector 8e as required.

Figure 34:
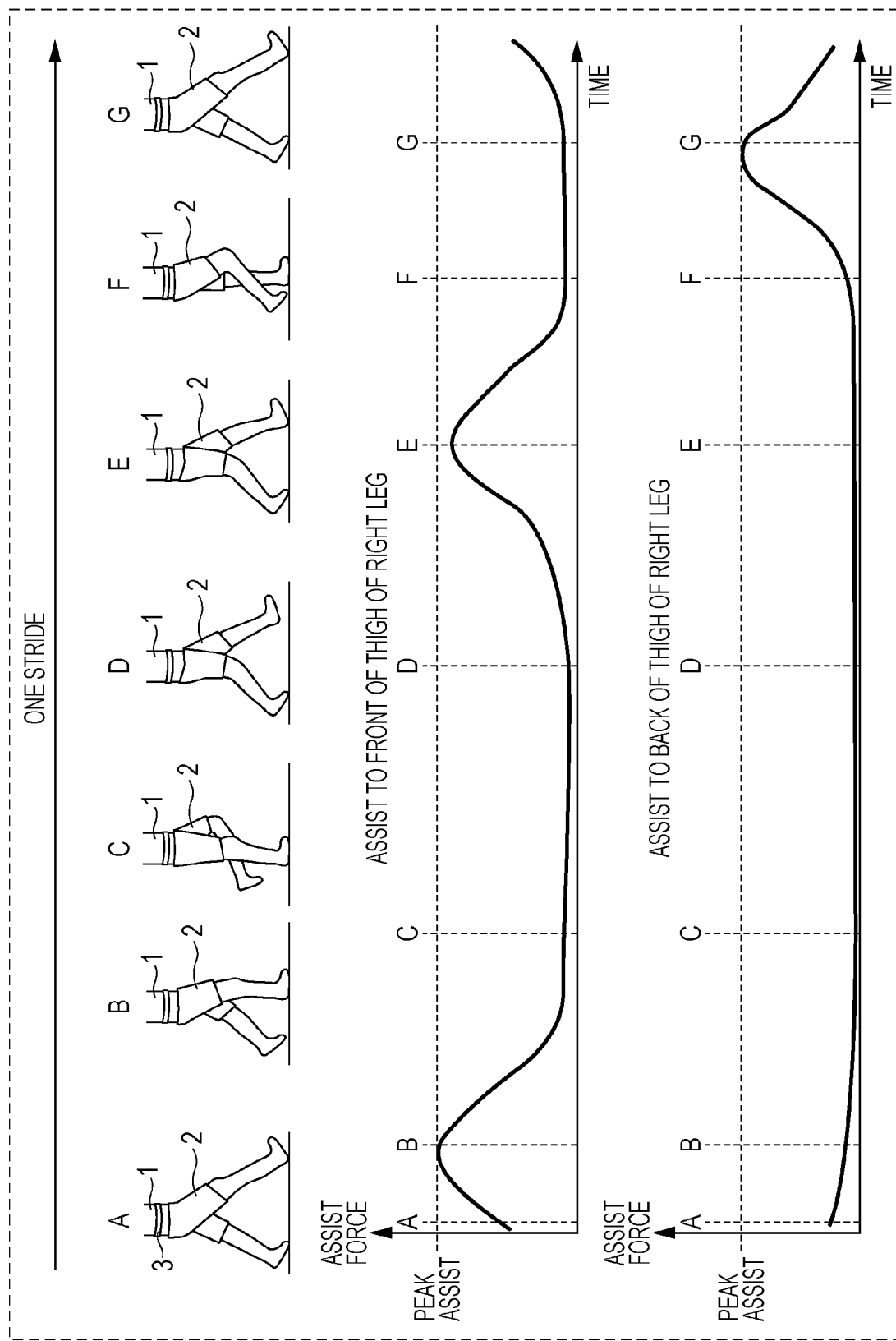
FIG. 34 illustrates actuation profiles for various phases in walk assist provided by an assist garment.

For example, FIG. 3B illustrates the actual signals of the sensors 7 (the current actual measurements of the signals of the sensors 7, that is, the signals of the sensors 7 subject to walking-state determination) used to determine that the current state of walking is Phase E within the process (Phases A to G) of walking assist provided by the assist garment 4 illustrated in FIG. 34, and the signals of the sensors 7 corresponding to individual phases (the signals of the sensors 7 in Phases E, F, and G are illustrated as a representative example) stored in the memory 8a.

As an example of "the signals of the sensors 7 corresponding to individual phases stored in the memory 8a" illustrated in FIG. 3B, FIG. 3C illustrates a first sensor signal value in Phase E and a second sensor signal value in Phase E. In FIG. 3C, signal values are represented by digital values 0, 1, 2, and 3. A greater digital value indicates a greater sensor signal value. FIG. 3D illustrates an example of driving of the assisting actuators 6 (only Actuators A to E are illustrated as a representative example) in Phase E. In FIG. 3D, different drive levels of each actuator are represented as 0, 1, 2, and 3. The greater the numerical value of the driving level, the greater the contraction of the corresponding actuator.

Referring to FIG. 34, to determine the motion or state of the user, the determinator 8c compares the actual signals of the sensors 7 with the signals of the sensors 7 corresponding to individual phases stored in the memory 8a. Then, this comparison reveals that the actual signals of the sensors 7 best match the signals of the sensors 7 corresponding to Phase E of the time response pattern as illustrated in FIG. 3C. This allows the determinator 8c to determine that the current walking state of the user is Phase E. Based on this determination made by the determinator 8c and a program (a program related to walking in this case) stored in the memory 8a in advance, the determinator 8c determines how to operate the assisting actuators 6, based on the example of driving of the assisting actuators 6 in Phase E (only Actuators A to E are illustrated as a representative example) illustrated in FIG. 3D, and transmits an instruction to the driver 8d via the actuator selector 8e. Based on the instruction from the determinator 8c, the driver 8d drives the corresponding assisting actuators 6 (Actuators A to E as a representative example).

Garment Body

Figure 23:
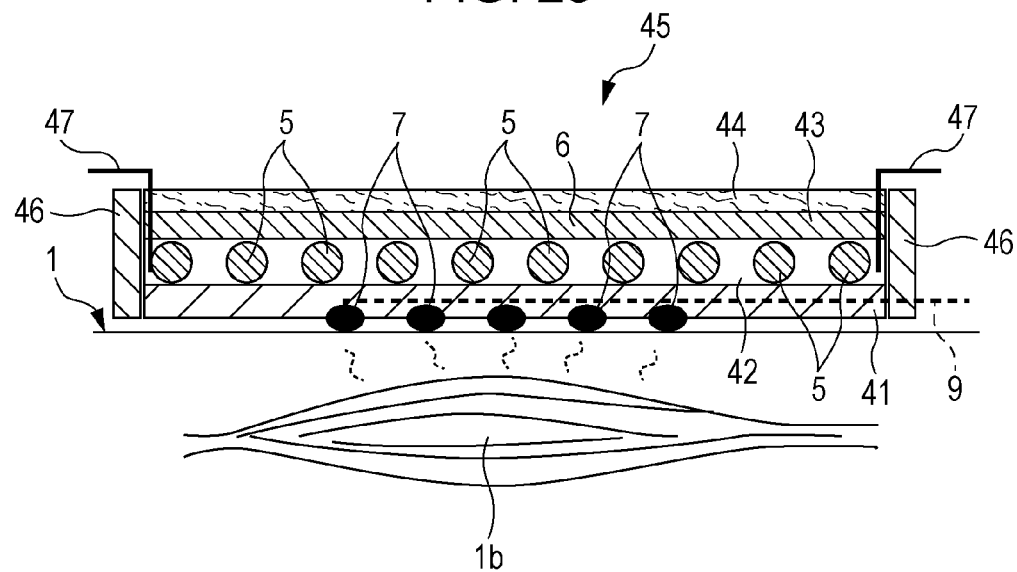
FIG. 23 is a cross-sectional view of a garment body according to a first structural example.

A first structural example 45 of the garment body 2 is illustrated in FIG. 23. According to the first structural example 45, first, the sensors 7 and the corresponding sensor wiring 9 are placed in a first layer 41 of the garment body 2 located closest to the user 1. The garment-fitting actuators 5 are placed in a second layer 42 located on top of the first layer 41. The assisting actuators 6, which have such an axis that crosses the axis of the garment-fitting actuators 5, are placed in a third layer 43 located on top of the second layer 42. A cover such as a piece of fabric for covering the entirety of the third layer 43 is placed in a fourth layer 44 that is the outermost layer. As a result, the first structural example 45 is of a four-layer structure as a whole. Reference numeral 46 in FIG. 23 denotes an assisting-actuator securing part for securing the assisting actuators 6 in place at each end, and reference numeral 47 denotes the wiring for the assisting actuators 6.

The first structural example 45 results in a simple structure. Further, all of the assisting actuators 6 are placed on the outside relative to the garment-fitting actuators 5. This configuration ensures that the assisting actuators 6 are not pressed by the garment-fitting actuators 5, thus reducing friction between the garment-fitting actuators 5 and the assisting actuators 6 during their extension and contraction.

Figure 24:
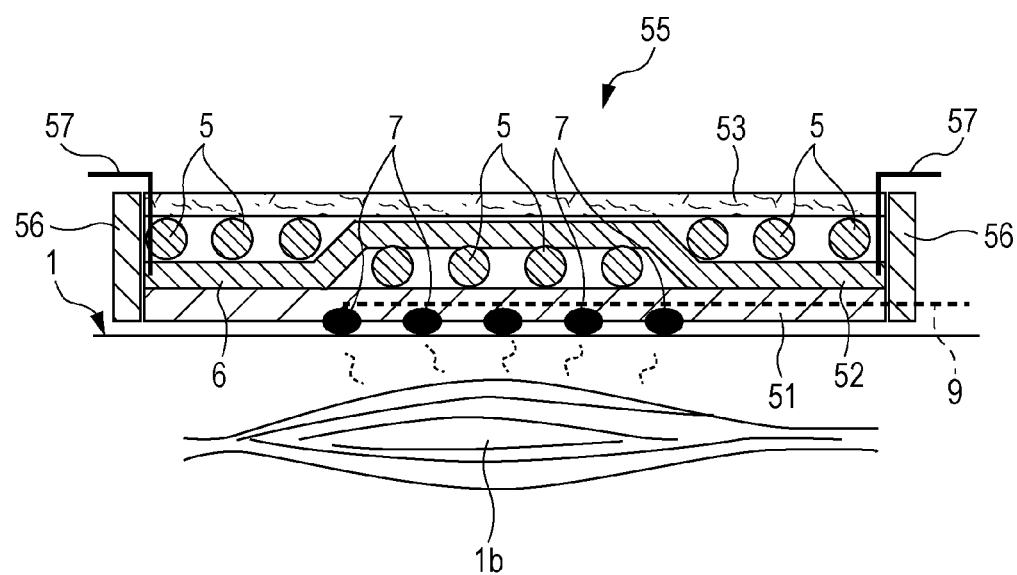
FIG. 24 is a cross-sectional view of a garment body according to a second structural example.

A second structural example 55 of the garment body 2 is illustrated in FIG. 24. According to the second structural example 55, first, the sensors 7 and the corresponding sensor wiring 9 are placed in a first layer 51 of the garment body 2 located closest to the user 1. The assisting actuators 6 are placed in a second layer 52 located on top of the first layer 51. The garment-fitting actuators 5, which have such an axis that crosses the axis of the assisting actuators 6, are also placed in the second layer 52. In areas of the second layer 52 near both end portions of the assisting actuators 6, the garment-fitting actuators 5 are placed at a position near a third layer described later, and in other areas of the second layer 52, the garment-fitting actuators 5 are placed at a position near the first layer. A cover such as a piece of fabric for covering the entirety of the second layer 52 is placed in a third layer 53 that is the outermost layer located on top of the second layer 52. As a result, the second structural example 55 is of a three-layer structure as a whole. Reference numeral 56 in FIG. 24 denotes an assisting-actuator securing part for securing the assisting actuators 6 in place at each end, and reference numeral 57 denotes the wiring for the assisting actuators 6.

In the second structural example 55, both ends of the assisting actuators 6 are securely pressed onto the user 1 by the garment-fitting actuators 5, allowing the assist force to be transmitted from the assisting actuators 6 to the muscle 1b with improved efficiency. In other areas, the garment-fitting actuators 5 are located closer to the user 1 than are the assisting actuators 6. This configuration ensures that the assisting actuators 6 are not pressed by the garment-fitting actuators 5, thus reducing friction between the garment-fitting actuators 5 and the assisting actuators 6 during their extension and contraction.

Figure 25:
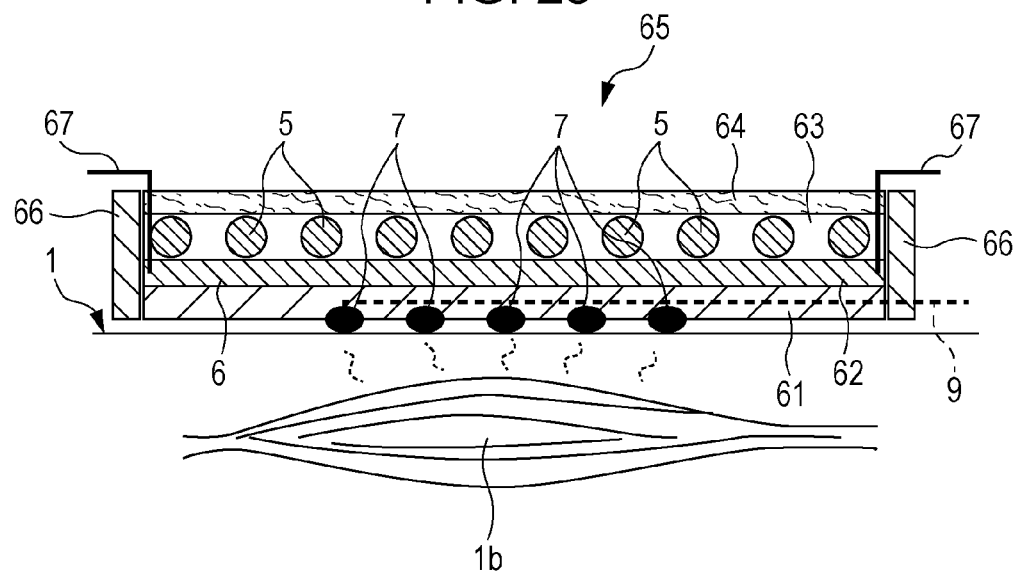
FIG. 25 is a cross-sectional view of a garment body according to a third structural example.

A third structural example 65 of the garment body 2 is illustrated in FIG. 25. According to the third structural example 65, first, the sensors 7 and the corresponding sensor wiring 9 are placed in a first layer 61 of the garment body 2 located closest to the user 1. The assisting actuators 6 are placed in a second layer 62 that is an intermediate layer. The garment-fitting actuators 5 are placed in a third layer 63 located on top of the second layer 62. A cover such as a piece of fabric for covering the entirety of the third layer 63 is placed in a fourth layer 64 that is the outermost layer located on top of the third layer 63. As a result, the third structural example 65 is of a four-layer structure as a whole. Reference numeral 66 in FIG. 25 denotes an assisting-actuator securing part for securing the assisting actuators 6 in place at each end, and reference numeral 67 denotes the wiring for the assisting actuators 6.

The third structural example 65 results in a simple structure. Further, the garment-fitting actuators 5 are located on the outside relative to the assisting actuators 6. This configuration allows the assisting actuators 6 to be securely pressed onto the user 1 by the garment-fitting actuators 5.

Figure 26:
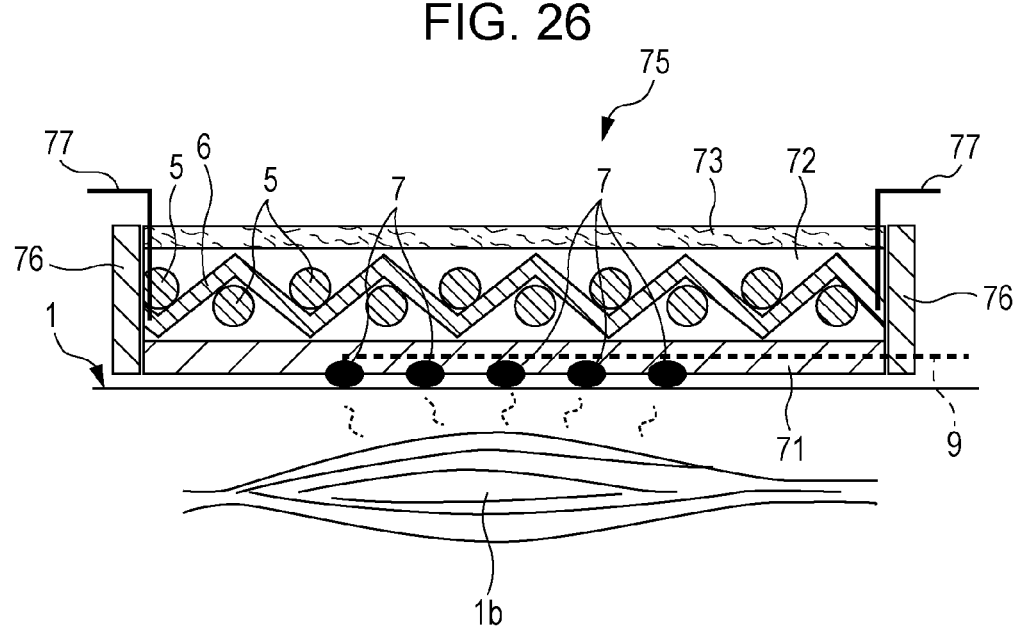
FIG. 26 is a cross-sectional view of a garment body according to a fourth structural example.

A fourth structural example 75 of the garment body 2 is illustrated in FIG. 26. According to the fourth structural example 75, first, the sensors 7 and the corresponding sensor wiring 9 are placed in a first layer 71 of the garment body 2 located closest to the user 1. In a second layer 72 located on top of the first layer 71, the assisting actuators 6 are placed in a zigzag configuration, and also the garment-fitting actuators 5, which have such an axis that crosses the axis of the assisting actuators 6, are placed alternately on the first layer side and on the third layer side described later with respect to the assisting actuators 6. A cover such as a piece of fabric for covering the entirety of the second layer 72 is placed in a third layer 73 that is the outermost layer located on top of the second layer 72. As a result, the fourth structural example 75 is of a three-layer structure as a whole. Reference numeral 76 in FIG. 26 denotes an assisting-actuator securing part for securing the assisting actuators 6 in place at each end, and reference numeral 77 denotes the wiring for the assisting actuators 6.

In the fourth structural example 75, each of the garment-fitting actuators 5 and the corresponding assisting actuator 6 are placed alternately. The garment-fitting actuator 5 and the assisting actuator 6 are thus firmly secured in place, reducing their displacement. In the fourth structural example 75, the garment-fitting actuator 5 and the corresponding assisting actuator 6 change their relative position alternately in two patterns, one in which the garment-fitting actuator 5 is located above the assisting actuator 6 and the other in which the garment-fitting actuator 5 is located below the assisting actuator 6. However, this is not to be construed restrictively. The relative position between the two actuators may change every any number of times the same pattern is repeated.

Sensor Calibration

Figure 27:
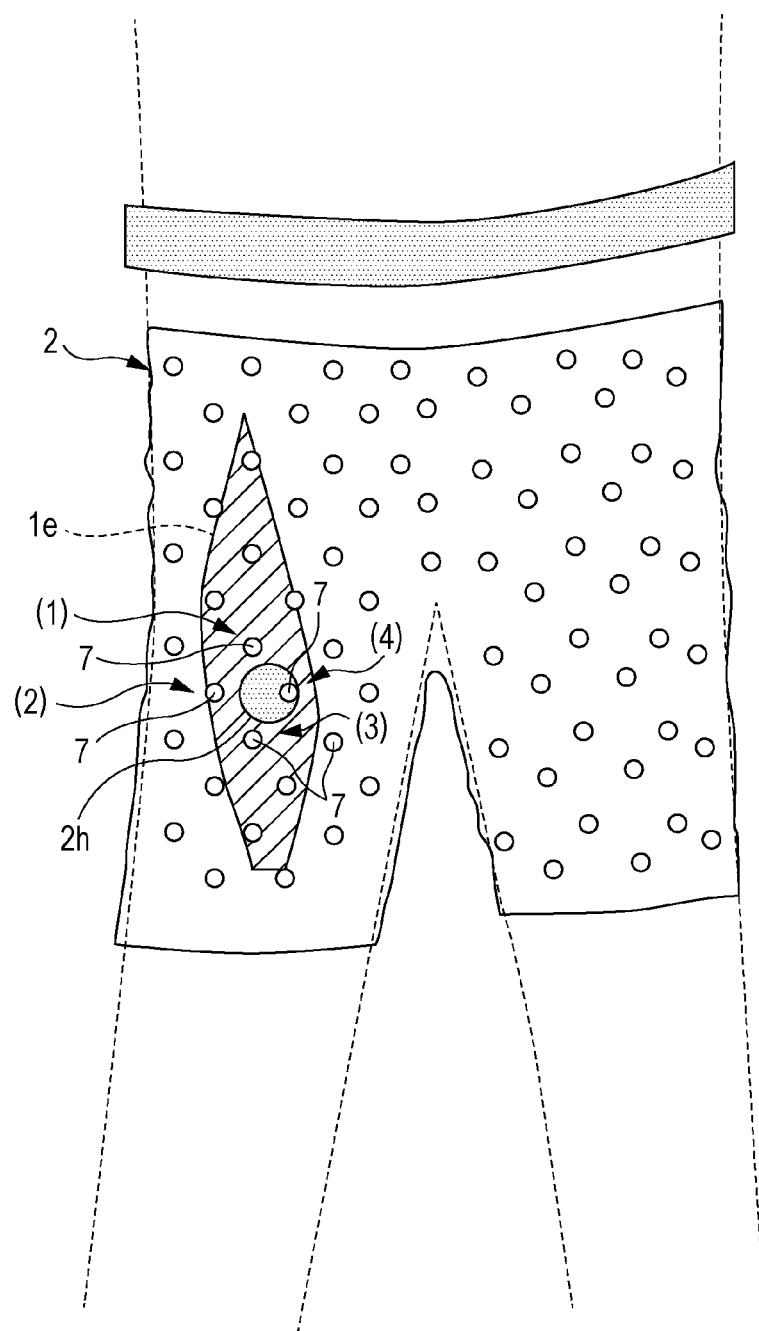
FIG. 27 illustrates sensor calibration.
Figure 28:
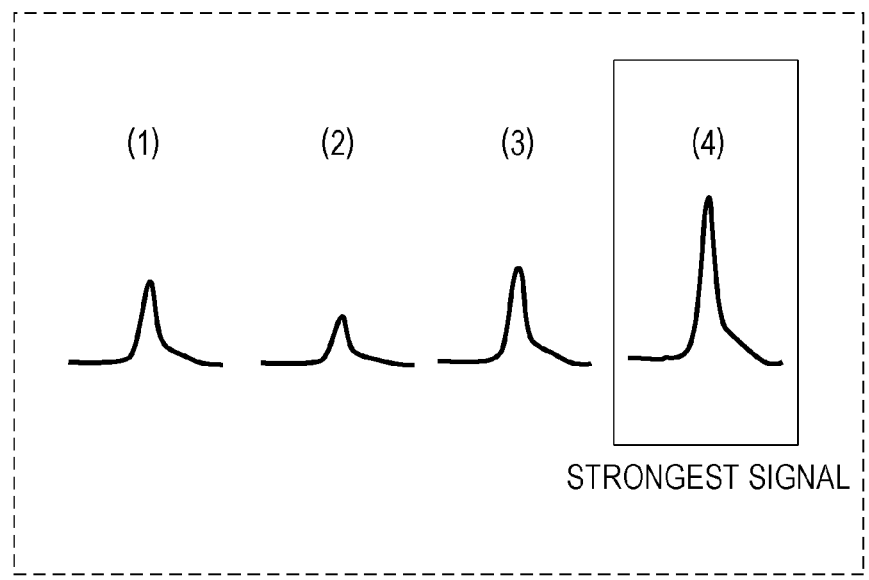
FIG. 28 illustrates a manner of processing sensor output.
Figure 29:
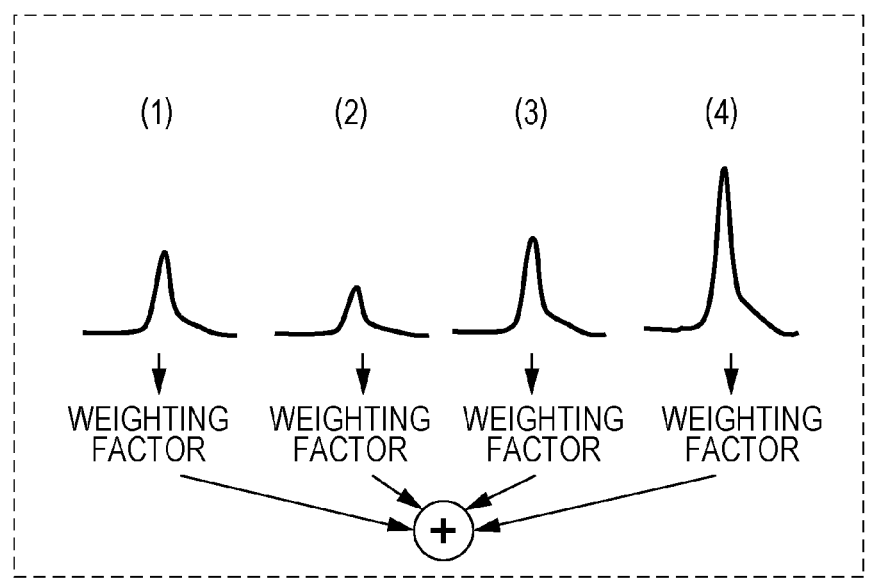
FIG. 29 illustrates another manner of processing sensor output.

FIG. 27 illustrates sensor calibration. FIG. 28 illustrates a manner of processing sensor output. FIG. 29 illustrates a manner of processing sensor output, which differs from the manner of processing sensor output illustrated in FIG. 28.

Depending on user's characteristics (such as body shape, sex, and age), or depending on how tightly the garment body 2 fits to the user 1, the actual placement positions of the sensors 7 differ for each individual user or every time the garment is donned. In such cases, sensor calibration may be performed automatically by the controller 8 to save the user 1 the trouble of adjusting the sensor positions by himself or herself every time such a necessity arises.

For example, as illustrated in FIG. 27, first, biosignals such as EMGs are acquired by the sensors 7 located in the vicinity of a sensor target region 2h corresponding to a target muscle 1e whose motion is to be assisted. The sensor target region may be a region in which the signal level of the target muscle 1e is high relative to the level of noise generated from a muscle located in close proximity to the target muscle 1e. For example, the sensor target region for the rectus femoris muscle may be a point on the rectus femoris muscle which is located near the halfway point between the pelvis (anterior inferior iliac spine) and the knee (tibial tuberosity), for example, an area within a radius of 1 cm from this halfway point as the center. In FIG. 27, the sensors 7 are placed uniformly across the entire garment body 2.

Next, the strongest signal is extracted by the computing unit 8b of the controller 8 from the biosignals acquired by the sensors 7. For example, suppose that Output Signals (1), (2), (3), and (4) are respectively output from four sensors 7, that is, sensors 7-1, 7-2, 7-3, and 7-4 as illustrated in FIG. 28. In this case, Output Signal (4) from the sensor 7-4 is the strongest signal.

Accordingly, the sensor 7 that has detected the strongest signal, Output Signal (4), is handled by the controller 8 as the sensor 7 to be used for the sensor target region 2h. Consequently, even in situations where use of the sensors 7 within the sensor target region 2h alone may fail to successfully detect the intended force and thus lead to malfunction, output signals from the sensors 7 located in the vicinity of the sensor target region 2h are taken into account and the strongest signal is extracted, and the sensor 7 corresponding to the strongest signal is selected by the controller 8 as the appropriate sensor 7 to be used, thus enabling correction, that is, sensor calibration.

This sensor calibration may be processed in another manner as described below. That is, instead of extracting only the strongest signal, as illustrated in FIG. 29, the computing unit 8b of the controller 8 multiples each of Output Signals (1), (2), (3), and (4) by a weighting factor, adds up all the resulting values, and then divides the sum by the number of output signals to calculate the mean of the output signals. The mean of the output signals calculated in this way may be acquired as a corrected output signal, and this corrected output signal may be used to perform sensor calibration.

Figure 30:
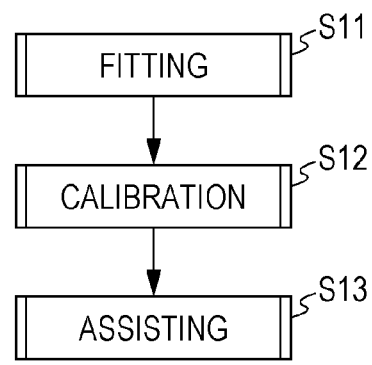
FIG. 30 is a flowchart illustrating the overall sequence of operation in the assist garment.

In one example, this calibration is performed at the following timing. FIG. 30 is a flowchart illustrating the overall sequence of operation in the assist garment.

As illustrated in FIG. 30, first, in step S11, the garment body 2 is put on the user 1, and then the garment-fitting actuators 5 are activated to fit the garment body 2 onto the user 1.

Then, sensor calibration is performed as described above in step S12.

Lastly, an assist operation using the assisting actuators 6 is performed in step S13. If, for example, a plurality of assist operation modes are selectable at this time, one of the assist operation modes may be selected by the input/output device 16. For example, if the assist operation modes include a walking mode and a stair climbing/descending mode, either of the two modes is selected before starting the assist.

Actuator Calibration

Figure 31:
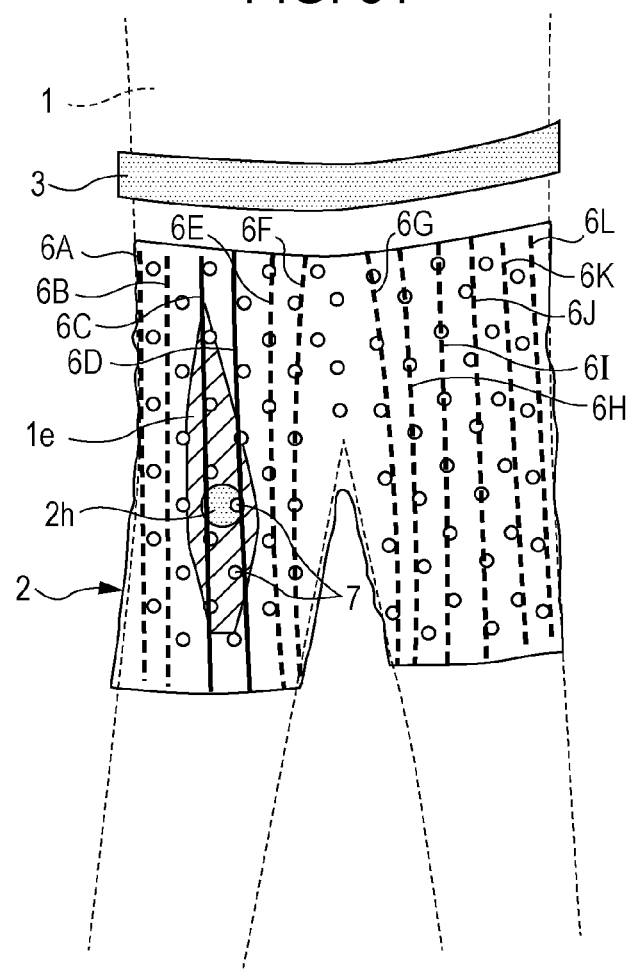
FIG. 31 illustrates selection of different assisting actuators due to differences in the location of a muscle among individual users.
Figure 32:
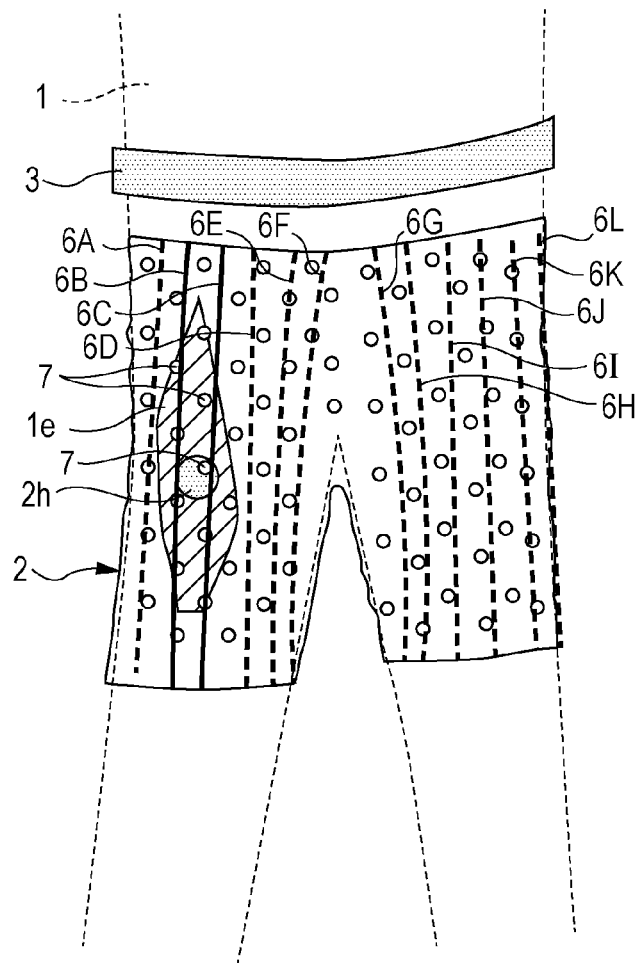
FIG. 32 illustrates selection of different assisting actuators due to differences in the location of a muscle among individual users.
Figure 33:
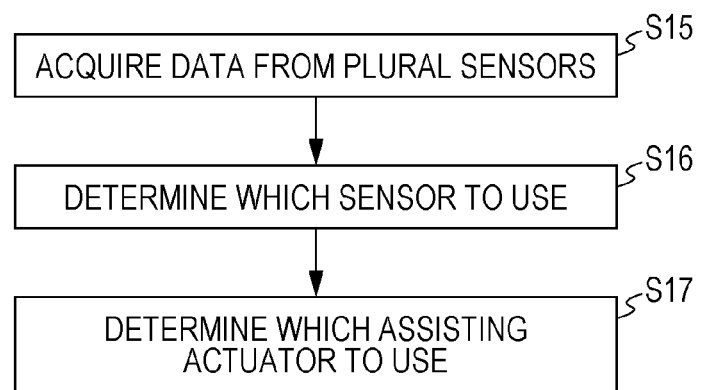
FIG. 33 is a flowchart illustrating the sequence of operation in actuator calibration.

FIGS. 31 and 32 illustrate selection of different assisting actuators due to differences in the location of a muscle among individual users 1. FIG. 33 is a flowchart illustrating the sequence of operation in actuator calibration.

If the sensor 7 corresponding to the strongest one of the signals output from the sensors 7 is identified as mentioned above, and then the assisting actuator 6 placed at a position corresponding to the sensor 7 (for example, placed near the sensor 7) is further selected by the controller 8, the assist force of the assisting actuator 6 may be properly transmitted from the assisting actuator 6 to the target muscle 1e. For example, for a given user 1, as illustrated in FIG. 31, of assisting actuators 6A to 6F corresponding to the thigh area or its vicinity among the assisting actuators 6 placed in the vertical direction of the garment body 2, the two assisting actuators 6C and 6D that provide signal strengths greater than the signal strengths provided by the other assisting actuators 6A, 6B, 6E, and 6F may be used. In contrast, as illustrated in FIG. 32, for another given user 1, the location of the corresponding muscle differs from the location in the above-mentioned user. Accordingly, of the assisting actuators 6A to 6F corresponding to the thigh area or its vicinity among the assisting actuators 6 placed in the vertical direction of the garment body 2, the two assisting actuators 6B and 6C that provide signal strengths greater than the signal strengths provided by the other assisting actuators 6A, 6D, 6E, and 6F may be used. In this way, based on data output from the sensors 7, the controller 8 is able to detect the position of the muscle 1b relative to the garment body 2, and correctly select the assisting actuator 6 located closest to the muscle 1b. Positional information on the individual sensors 7, and positional information on the assisting actuators 6 corresponding to the individual sensors 7 are stored in the memory 8a of the controller 8 in advance.

For example, the assisting actuator 6 to be used may be determined based on the distance from the sensor 7 that outputs the strongest signal.

For example, the assisting actuator 6 located at the shortest distance from the sensor 7 that outputs the strongest signal, and the assisting actuator 6 located at the second shortest distance from the sensor 7 that outputs the strongest signal may be selected for use.

The memory 8a may store information related to the distance between each of the sensors 7 and the assisting actuators 6. For example, information for identifying each of the sensors 7 may be stored in association with information for identifying the assisting actuator 6 located at the shortest distance from the sensor 7, and with information for identifying the assisting actuator 6 located at the second shortest distance from the sensor 7.

In one example, this actuator calibration is performed at the following timing.

As illustrated in FIG. 33, first, in step S15, the garment body 2 is put on the user 1, and then the garment-fitting actuators 5 are activated to fit the garment body 2 onto the user 1. Then, the controller 8 acquires data detected from the sensors 7 located near the sensor target region 2h.

Subsequently, in step S16, for example, the controller 8 identifies the sensor 7 corresponding to the strongest signal among the data detected from the sensors 7, and determines the identified sensor 7 as the sensor 7 to be used.

Lastly, in step S17, the controller 8 determines, as the assisting actuator 6 to be used, the assisting actuator 6 corresponding to the determined sensor. For example, the controller 8 references the following pieces of information retained in the memory 8a: information for identifying the assisting actuator 6 located at the shortest distance from each of the sensors 7, and information for identifying the assisting actuator 6 located at the second shortest distance from each of the sensors 7, and the controller 8 determines the assisting actuator 6 located at the shortest distance from the sensor 7 that outputs the strongest signal, and the assisting actuator 6 located at the second shortest distance from the sensor 7 that outputs the strongest signal.

Walking Assist

FIG. 34 illustrates various steps in walk assist provided by the assist garment 4.

As illustrated in FIG. 34, in one example, the assisting actuators 6 provide assist to the muscle 1b on the front and back of the right thigh in the following manner under the control of the controller 8. This assist is provided by generating an assist force in synchronization with the movement of the muscle 1b detected by the sensor 7. Although for brevity the following description is directed to the assisting actuators 6 that provide assist to the muscle 1b on the front and back of the right thigh, the same applies to the assisting actuators 6 that provide assist to the muscle 1b on the front and back of the left thigh.

First, during the transition from State G to State A, the user 1 swings the right foot forward, and starts to walk one step. At this time, the amount of assist provided by the assisting actuators 6 corresponding to the muscle 1b on the front of the right thigh is increased, whereas the amount of assist provided by the assisting actuators 6 corresponding to the muscle 1b on the back of the right thigh is gradually decreased. The expression "increase the amount of assist" may mean causing the assisting actuators 6 to contract when the corresponding muscle contracts, or causing the assisting actuators 6 to extend when the corresponding muscle extends.

In FIG. 34, when assist is provided to the front of the thigh area of the right leg, the assisting actuators 6 undergo a large contraction in State B, and the assisting actuators 6 undergo a large extension in State E. In FIG. 34, when assist is provided to the back of the thigh area of the right leg, the assisting actuators 6 undergo a large contraction in State G.

Next, during the transition from State A to State B, the user 1 rests his or her weight on the right foot for support while starting to lift the left foot off the ground. During this transition to State B, the amount of assist provided by the assisting actuators 6 corresponding to the muscle 1b on the front of the right thigh is increased to the maximum until the peak assist value is reached. At this time, only minimal assist is provided by the assisting actuators 6 corresponding to the muscle 1b on the back of the right thigh.

Next, during the transition from State B to State C, the user 1 rests his or her whole weight on the right foot for support, with the left foot completely off the ground. At this time, the amount of assist provided by the assisting actuators 6 corresponding to the muscle 1b on the front of the right thigh is gradually decreased, and only minimal assist is provided by the assisting actuators 6 corresponding to the muscle 1b on the back of the right thigh.

Next, during the transition from State C to State D, the user 1 swings the left foot forward, and starts to walk one more step. At this time, only minimal assist is provided by the assisting actuators 6 corresponding to the muscle 1b on each of the front and back of the right thigh.

Next, during the transition from State D to State E, the user 1 rests his or her weight on the left foot for support while starting to lift the right foot off the ground. During this transition from State D to State E, the amount of assist provided by the assisting actuators 6 corresponding to the muscle 1b on the front of the right thigh is increased. At this time, only minimal assist is provided by the assisting actuators 6 corresponding to the muscle 1b on the back of the right thigh.

Next, during the transition from State E to State F, the user 1 rests his or her whole weight on the left foot for support, with the right foot completely off the ground. At this time, the amount of assist provided by the assisting actuators 6 corresponding to the muscle 1b on the front of the right thigh is gradually decreased, and only minimal assist is provided by the assisting actuators 6 corresponding to the muscle 1b on the back of the right thigh.

Next, during the transition from State F to State G, the user 1 swings the right foot forward, and starts to walk one more step. During this transition from State F to State G, the amount of assist provided by the assisting actuators 6 corresponding to the muscle 1b on the back of the right thigh is increased to the maximum until the peak assist value is reached. At this time, only minimal assist is provided by the assisting actuators 6 corresponding to the muscle 1b on the front of the right thigh.

Although the above-mentioned example of assist involves gradually changing the assist force in synchronization with the movement of the muscle 1b, the manner of providing assist is not limited to this. Alternatively, for example, the assist force may be generated in a pulse-like manner at the timing when assist is required. In certain situations such as when only minimal assist is required, virtually no assist may be provided.

Assist Phase

Figure 35:
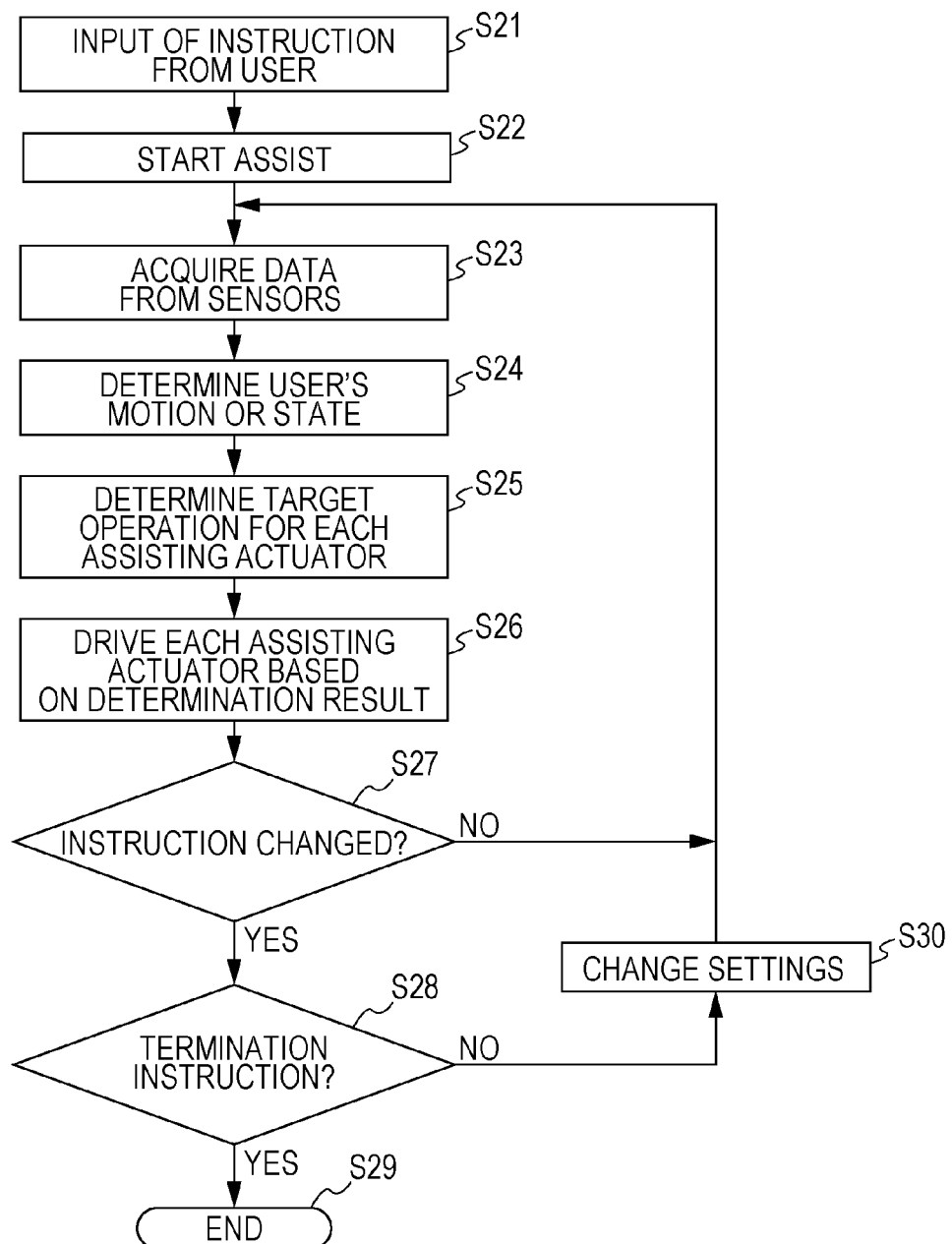
FIG. 35 is a flowchart illustrating how a controller controls the drive of assisting actuators.

FIG. 35 is a flowchart illustrating how the controller 8 controls the drive of the assisting actuators 6.

As illustrated in FIG. 35, the drive of assisting actuators 6 is controlled by the controller 8 as follows. In this example, the assisting actuators 6 that provide assist differ depending on the walking state of the user 1. Since each of the sensors 7 provides information about the movement of the corresponding muscle 1b, such information may be compared by the controller 8 against, for example, a human walk pattern to distinguish between different walking states of the user 1. This allows the controller 8 to select which assisting actuators 6 are to be activated in correspondence with the muscle 1b, and provide assist in synchronization with movement of the muscle 1b.

First, in step S21, one mode (for example, walking mode) is selected and input by the user 1 using the input/output device 16.

Next, the assist is started in step S22. That is, the controller 8 starts to control the drive of the assisting actuators 6 based on a program previously stored in the memory 8a.

Next, in step S23, the controller 8 acquires data from all of the sensors 7 prior to actually starting control of the drive of the assisting actuators 6.

Next, in step S24, the controller 8 determines the motion or state of the user 1 based on the data acquired from all of the sensors 7 by the controller 8. For example, the controller 8 determines whether the user 1 is currently walking, and if so, what the current state of walking is.

Next, in step S25, the controller 8 determines a target operation for each of the assisting actuators 6 based on the determined motion or state of the user 1. Determining a target operation for each assisting actuator may involve determining "the timing and extent of contraction" of each of the assisting actuators 6, or determining "the timing and extent of extension" of each of the assisting actuators 6.

Next, in step S26, the controller 8 controls the drive of each assisting actuator based on the target operation determined in step S25.

Next, in step S27, the controller 8 determines whether an instruction has been changed using, for example, the input/ output device 16. If the controller 8 determines that an instruction has been changed, the processing proceeds to step S28. If the controller 8 determines that an instruction has not been changed, the processing returns to step S23.

Next, in step S28, the controller 8 determines whether the changed instruction is a termination instruction. If the controller 8 determines that the changed instruction is not a termination instruction, the processing proceeds to step S30. If the controller 8 determines that the changed instruction is a termination instruction, the processing proceeds to step S29.

Next, in step S29, the series of operations is ended.

In step S30, after the setting changes based on the changed instruction are made by the controller 8, the processing returns to step S23.

Tightening of Garment Body

Figure 36:
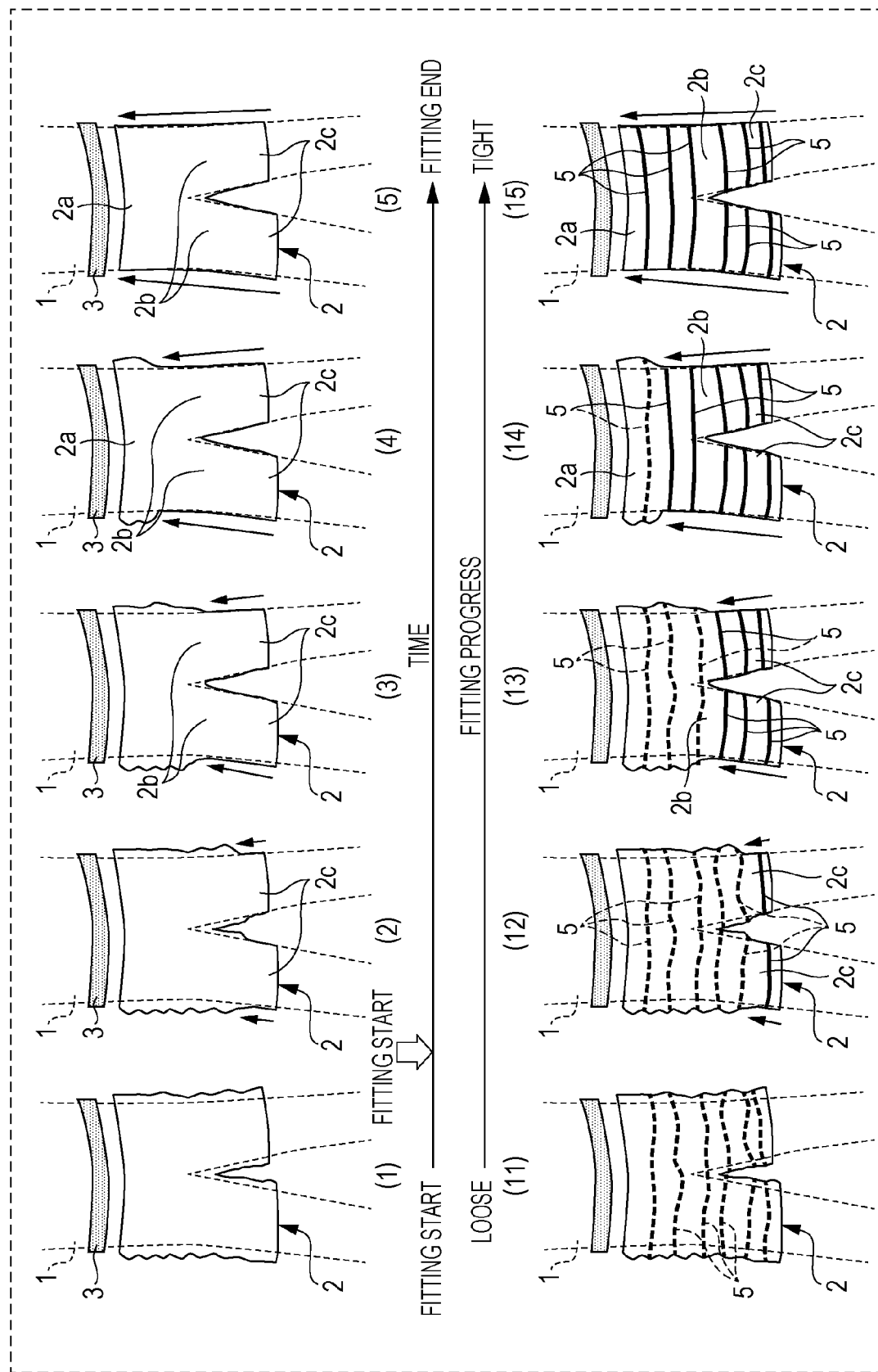
FIG. 36 illustrates a series of operations performed to tighten a garment body onto a user.
Figure 37:
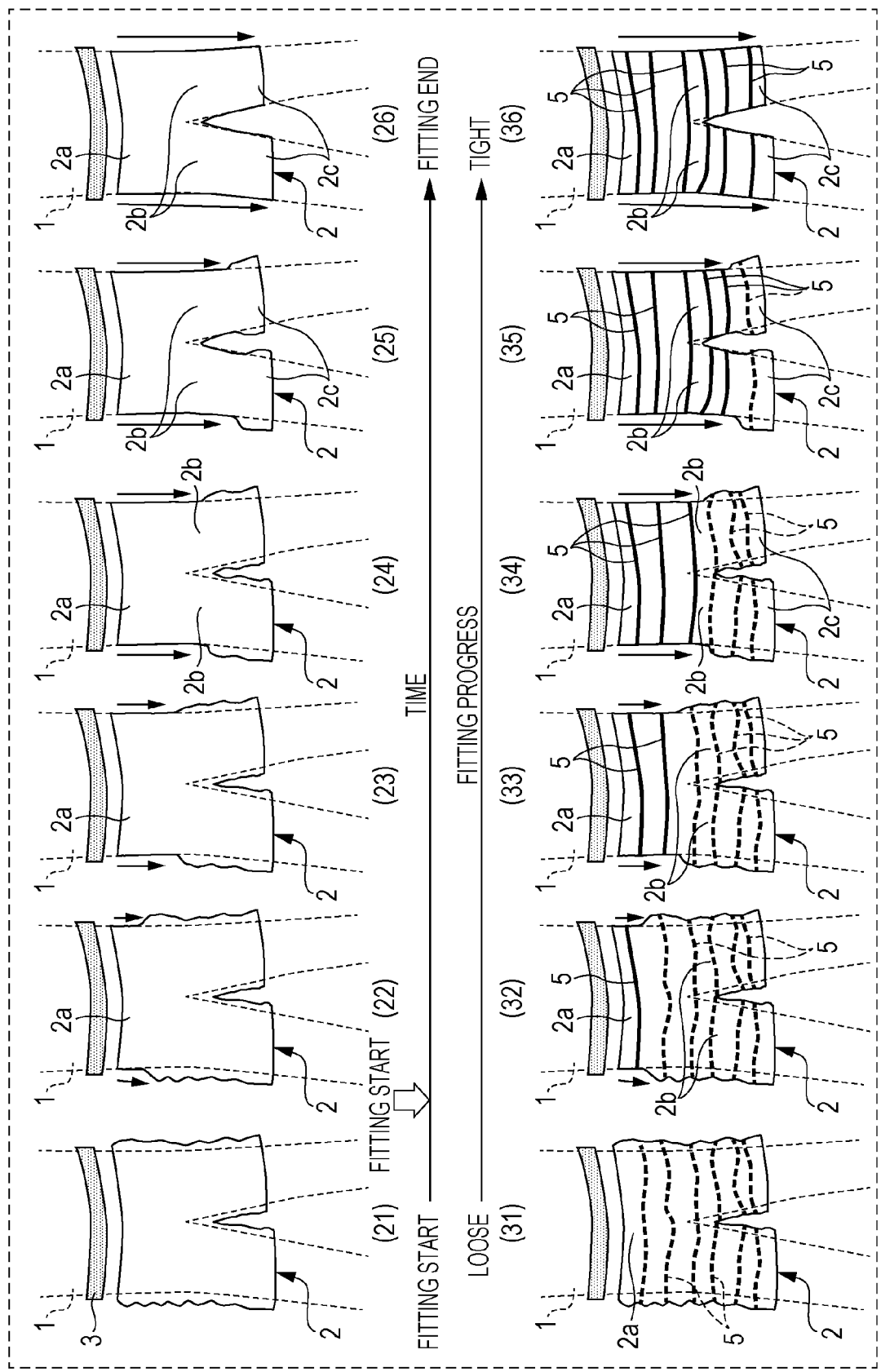
FIG. 37 illustrates a series of operations performed to tighten a garment body onto a user by another method.

FIG. 36 illustrates a series of operations performed to tighten the garment body 2 onto the user 1. FIG. 37 illustrates a series of operations performed to tighten the garment body 2 onto the user 1 by a method different from the method illustrated in FIG. 36.

A series of operations performed to tighten the garment body 2 onto the user 1 will be described with reference to each of FIGS. 36 and 37.

FIG. 36 illustrates a method of tightening the garment body 2 after the user 1 puts on the garment body 2, beginning at the lower end portion of the garment body 2 and proceeding toward the upper end portion. FIG. 37 illustrates the reverse process, that is, a method of tightening the garment body 2 after the user 1 puts on the garment body 2, beginning at the upper end portion of the garment body 2 and proceeding toward the lower end portion. In both cases, tightening is applied beginning at one axial (vertical) end portion of the garment body 2 and proceeding toward the other axial end portion.

First, FIG. 36 illustrates a method of tightening the garment body 2 after the user 1 puts on underpants as an example of the garment body 2, beginning at the lower end portion of the garment body 2 and proceeding toward the upper end portion. States (1) to (5) in the upper part of FIG. 36 each depict the outward appearance of the garment body 2, and States (11) to (15) in the lower part of FIG. 36 each depict the corresponding state of the garment-fitting actuators 5 of the garment body 2. States (1) to (5) are arranged in time series, and States (11) to (15) are arranged in time series. State (1) corresponds to State (11), State (2) corresponds to State (12), State (3) corresponds to State (13), State (4) corresponds to State (14), and State (5) corresponds to State (15). For States (11) to (15), dotted lines indicate the garment-fitting actuators 5 in an inactive and non-contracting state, and solid lines indicate the garment-fitting actuators 5 in an active and contracting state. When the garment-fitting actuators 5 are activated by the controller 8, the drive of the garment-fitting actuators 5 is controlled such that the garment-fitting actuators 5 contract gradually. Parts of the garment body 2 whose contours are represented by wavy lines indicate parts in a loose state. Parts of the garment body 2 whose contours are represented by straight lines indicate parts in a tightened state. Upward arrows indicate the direction in which the garment body 2 is changed from a loose state to a tightened state.

States (1) and (11) in FIG. 36 represent the state immediately after the user 1 puts on the garment body 2, with the garment body 2 generally worn loose. All of the garment-fitting actuators 5 are in a non-activated state at this point.

Next, in States (2) and (12) in FIG. 36, the garment-fitting actuators 5 in the lower end portion 2c of the garment body 2 are activated to contract by the controller 8 either sequentially or all at once to tighten the lower end portion 2c of the garment body 2. At this time, other portions of the garment body 2 are loose with the garment-fitting actuators 5 remaining in a non-activated state. Hereinafter, likewise for States (3) and (13), States (4) and (14), and States (5) and (15), only those portions of the garment body 2 in a tightened state will be described, and portions omitted in the following description are in a loose state.

Next, in States (3) and (13) in FIG. 36, with the garment-fitting actuators 5 in the lower end portion 2c of the garment body 2 activated and contracting, the garment-fitting actuators 5 located further above the lower end portion 2c are activated to contract by the controller 8 either sequentially or all at once, thus tightening the garment body 2 all the way up to the area further above the lower end portion 2c. Next, the garment-fitting actuators 5 in the base portion 2b of the thigh area are activated to contract by the controller 8 either sequentially or all at once, thus tightening the part of the garment body 2 from the lower end portion 2c to the base portion 2b of the thigh area.

Next, in States (4) and (14) in FIG. 36, with the garment-fitting actuators 5 in the part of the garment body 2 from the lower end portion 2c to the base portion 2b of the thigh area activated and contracting, the garment-fitting actuators 5 located above the base portion 2b of the thigh area are activated to contract by the controller 8 either sequentially or all at once, thus tightening the part of the garment body 2 from the lower end portion 2c to the area above the base portion 2b of the thigh area.

Next, in States (5) and (15) in FIG. 36, with the garment-fitting actuators 5 in the part of the garment body 2 from the lower end portion 2c to the area above the base portion 2b of the thigh area activated and contracting, the garment-fitting actuators 5 in the upper end portion 2a of the garment body 2 are activated to contract by the controller 8 either sequentially or all at once, thus tightening the part of the garment body 2 from the lower end portion 2c to the upper end portion 2a, that is, the entire garment body 2.

The series of operations above enables the garment body 2 to change gradually from a loose state to a tightened state while having its wrinkles smoothed out, beginning at the lower end portion 2c and proceeding toward the upper end portion 2a, thus allowing the garment body 2 to fit onto the user 1.

Next, FIG. 37 illustrates a method of tightening the garment body 2 in the reverse order after the user 1 puts on underpants as an example of the garment body 2, beginning at the upper end portion of the garment body 2 and proceeding toward the lower end portion. States (21) to (26) in the upper part of FIG. 37 each depict the outward appearance of the garment body 2, and States (31) to (36) in the lower part of FIG. 37 each depict the corresponding state of the garment-fitting actuators 5 of the garment body 2. States (21) to (26) are arranged in time series, and States (31) to (36) are arranged in time series. State (21) corresponds to State (31), State (22) corresponds to State (32), State (23) corresponds to State (33), State (24) corresponds to State (34), and State (25) corresponds to State (35). For States (31) to (36), dotted lines indicate the garment-fitting actuators 5 in an inactive and non-contracting state, and solid lines indicate the garment-fitting actuators 5 in an active and contracting state. When the garment-fitting actuators 5 are activated by the controller 8, the drive of the garment-fitting actuators 5 is controlled such that the garment-fitting actuators 5 contract gradually. Parts of the garment body 2 whose contours are represented by wavy lines indicate parts in a loose state. Parts of the garment body 2 whose contours are represented by straight lines indicate parts in a tightened state. Downward arrows indicate the direction in which the garment body 2 is changed from a loose state to a tightened state.

States (21) and (31) in FIG. 37 represent the state immediately after the user 1 puts on the garment body 2, with the garment body 2 generally worn loose. All of the garment-fitting actuators 5 are in a non-activated state at this point.

Next, in States (22) and (32) in FIG. 37, the garment-fitting actuators 5 in the upper end portion 2a of the garment body 2 are activated to contract by the controller 8 either sequentially or all at once to tighten the upper end portion 2a of the garment body 2. At this time, other portions of the garment body 2 are loose with the garment-fitting actuators 5 remaining in a non-activated state. Hereinafter, likewise for States (23) and (33), States (24) and (34), States (25) and (35) and States (26) and (36), only those portions of the garment body 2 in a tightened state will be described, and portions omitted in the following description are in a loose state.

Next, in States (23) and (33) in FIG. 37, with the garment-fitting actuators 5 in the upper end portion 2a of the garment body 2 activated and contracting, the garment-fitting actuators 5 located further below the upper end portion 2a are activated to contract by the controller 8 either sequentially or all at once, thus tightening the garment body 2 all the way down to the area further below the upper end portion 2a.

Next, in States (24) and (34) in FIG. 37, the garment-fitting actuators 5 located above the base portion 2b of the thigh area are activated to contract by the controller 8 either sequentially or all at once, thus tightening the part of the garment body 2 from the upper end portion 2a to the area above the base portion 2b of the thigh area.

Next, in States (25) and (35) in FIG. 37, with the garment-fitting actuators 5 in the part of the garment body 2 from the upper end portion 2a to the area above the base portion 2b of the thigh area activated and contracting, the garment-fitting actuators 5 in the base portion 2b of the thigh area are activated to contract by the controller 8 either sequentially or all at once, thus tightening the part of the garment body 2 from the upper end portion 2a to the base portion 2b of the thigh area.

Next, in States (26) and (36) in FIG. 37, with the garment-fitting actuators 5 in the part of the garment body 2 from the upper end portion 2a to the base portion 2b of the thigh area activated and contracting, the garment-fitting actuators 5 in the lower end portion 2c of the garment body 2 are activated to contract by the controller 8 either sequentially or all at once, thus tightening the part of the garment body 2 from the upper end portion 2a to the lower end portion 2c, that is, the entire garment body 2.

The series of operations above enables the garment body 2 to change gradually from a loose state to a tightened state while having its wrinkles smoothed out, beginning at the upper end portion 2a and proceeding toward the lower end portion 2c, thus allowing the garment body 2 to fit onto the user 1.

Figure 38:
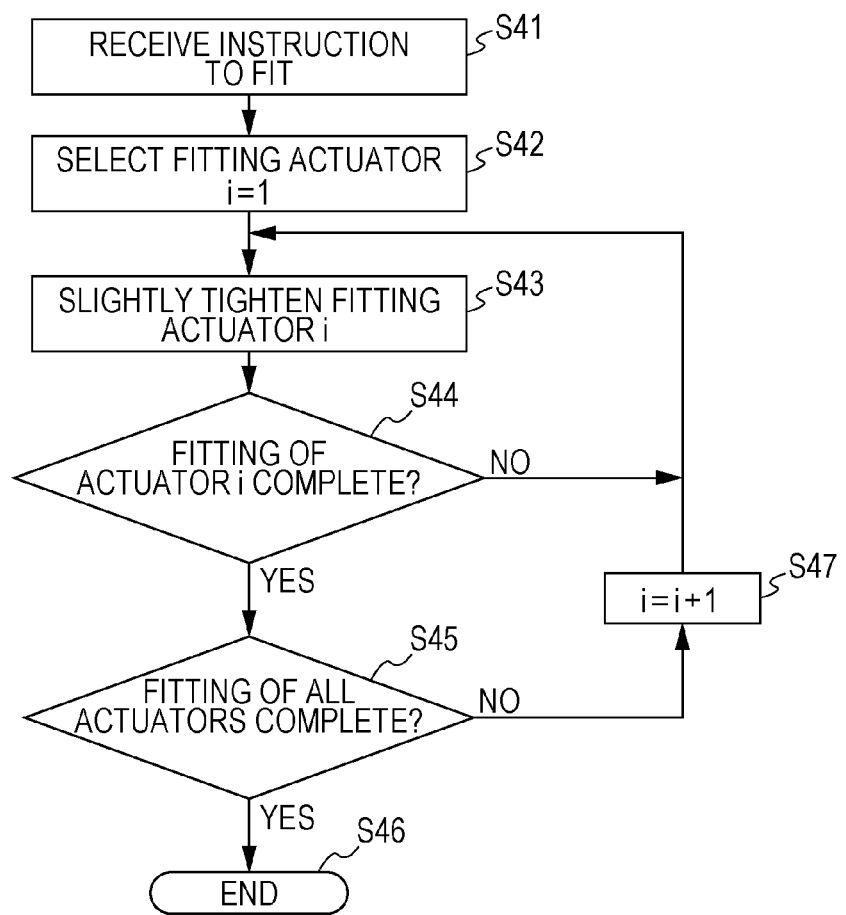
FIG. 38 is a flowchart illustrating an operating procedure for garment-fitting actuators during the donning of a garment body.

Operating Procedure for Garment-Fitting Actuators During Donning of Garment Body FIG. 38 is a flowchart illustrating an operating procedure for the garment-fitting actuators 5 during the donning of the garment body 2.

Next, an operating procedure for the garment-fitting actuators 5 during the donning of the garment body 2 will be described with reference to FIG. 38.

First, in step S41, the processing waits until a start signal for the garment-fitting actuators 5 is input to the controller 8 upon closing and engagement of the engagement sections 3a of the controller belt 3. Upon input of a start signal to the controller 8, the processing proceeds to step S42.

Next, in step S42, the controller 8 selects the (i=1)-th garment-fitting actuator 5 as the garment-fitting actuator 5 of interest.

Next, in step S43, under the control of the controller 8, the drive of the (i=1)-th garment-fitting actuator 5 selected by the controller 8 is started, and the (i=1)-th garment-fitting actuator 5 is contracted slightly to start tightening operation. At the start of tightening, the garment-fitting actuator 5 may be contracted in length by some fraction of the total contraction, such as not more than (L1−L2)×0.10 or less, where L1 denotes the length of the garment-fitting actuator 5 at no contraction, and L2 denotes the length of the garment-fitting actuator 5 at its maximum contraction.

Next, in step S44, the controller 8 determines whether contraction of the (i=1)-th garment-fitting actuator 5 is completed based on information from the sensor 7 such as the axial-force sensor 7A or the perpendicular-force sensor 7B. If the controller 8 determines that contraction of the (i=1)-th garment-fitting actuator 5 is not completed, the processing returns to step S43. If the controller 8 determines that contraction of the (i=1)-th garment-fitting actuator 5 is completed, the processing proceeds to step S45.

Next, in step S45, the controller 8 determines whether the activation, that is, contraction of all of the garment-fitting actuators 5 is completed. If the controller 8 determines that contraction of all of the garment-fitting actuators 5 is not completed, the processing proceeds to step S47. If the controller 8 determines that contraction of all of the garment-fitting actuators 5 is completed, the processing proceeds to step S46 where the processing ends.

In step S47, after the (i=i+1)-th garment-fitting actuator 5 is selected by the controller 8 as the target garment-fitting actuator 5, the processing proceeds to step S43. The (i=i+1)-th garment-fitting actuator 5 may be the garment-fitting actuator 5 adjacent to the (i=1)-th garment-fitting actuator 5. The (i=1)-th garment-fitting actuator 5 may be the garment-fitting actuator 5 in the uppermost end portion of the garment body 2 or the garment-fitting actuator 5 in the lowermost end portion.

With this manner of processing, the garment-fitting actuators 5 arranged in order from the upper end portion 2a of the garment body 2 toward the lower end portion 2c or from the lower end portion 2c toward the upper end portion 2a can be controlled to be driven sequentially one by one. This configuration involves fitting the garment-fitting actuators 5 one by one when the garment-fitting actuators 5 are activated to tighten and fit the garment body 2 onto the user 1, thus allowing the user himself or herself to readily recognize locations of improper fit on the user. This makes it possible to prompt the user to correct such error locations by himself or herself (for example, by smoothing out wrinkles on the garment body 2), without presenting the error locations to the user.

Doffing of Garment Body

Figure 39:
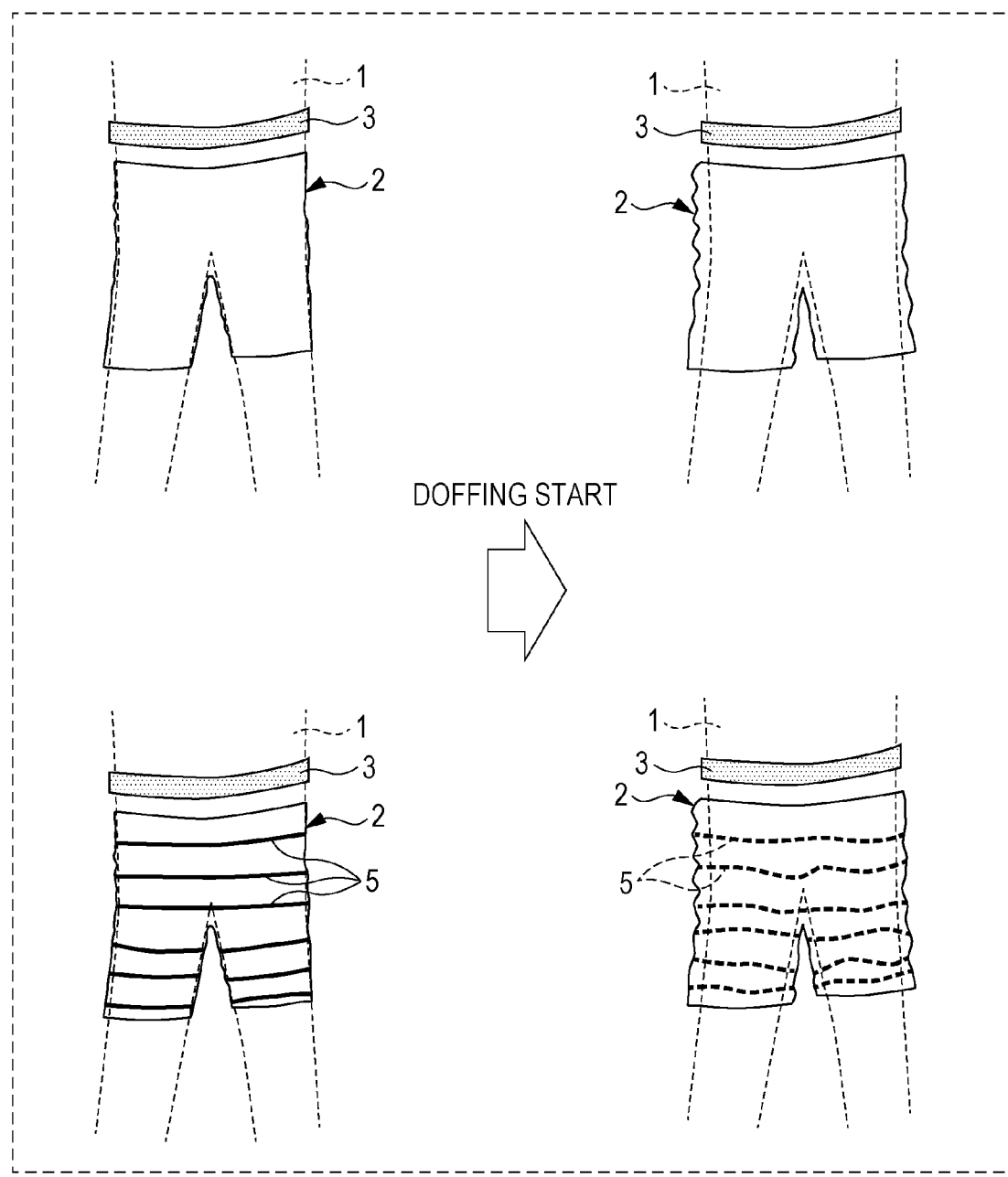
FIG. 39 illustrates doffing of a garment body.
Figure 40:
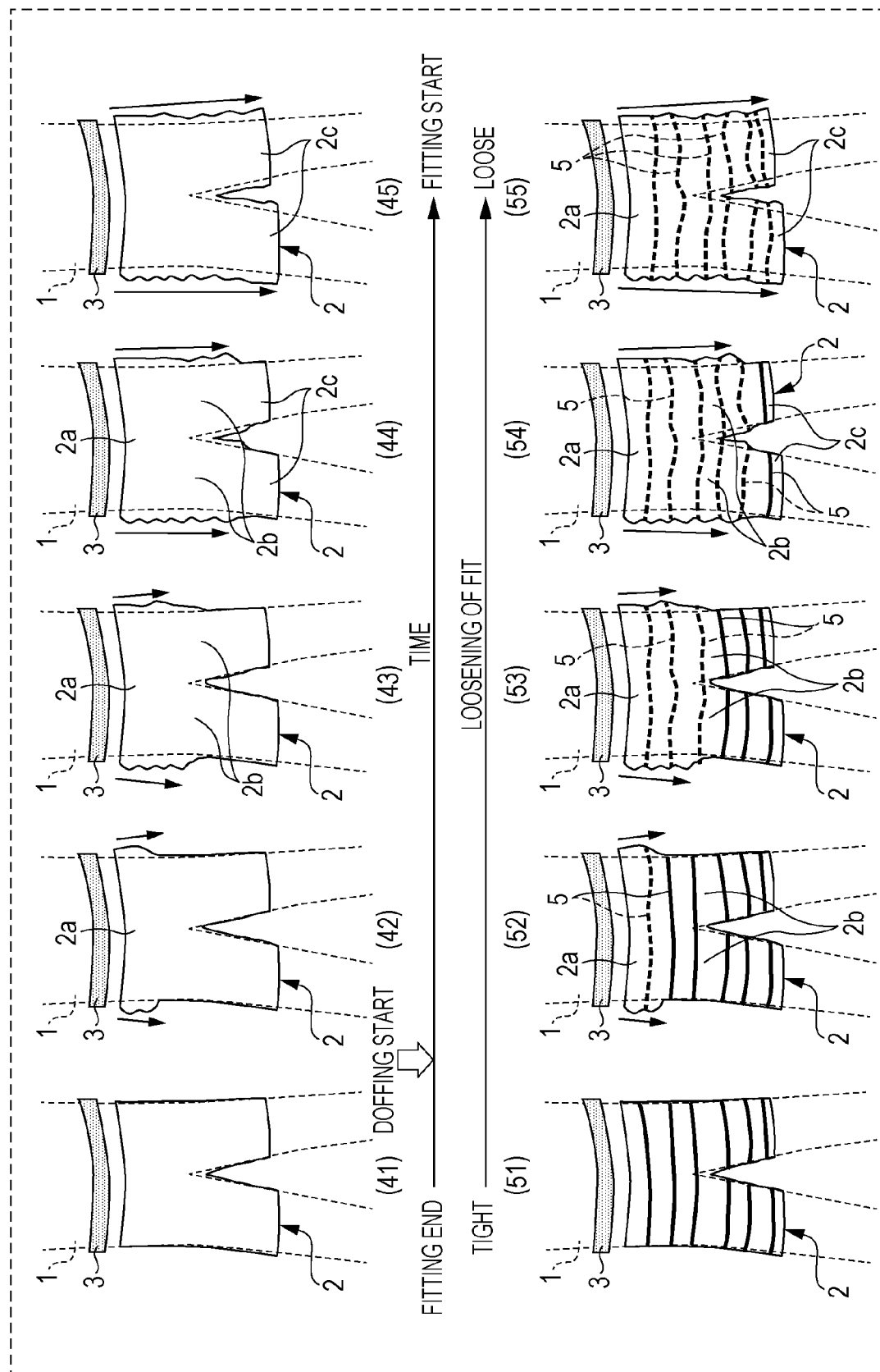
FIG. 40 illustrates a series of operations performed to loosen a garment body for a user.

FIG. 39 illustrates doffing of the garment body 2. FIG. 40 illustrates a series of operations performed to loosen the garment body 2 for the user 1.

One way of doffing the garment body 2 is to deactivate all of the garment-fitting actuators 5 of the garment body 2 to allow the entire garment body 2 to loosen at once as illustrated in FIG. 39. In this case, tightening is loosened in all areas of the garment body 2 to allow for quick doffing of the garment body 2 from the user 1.

Other than the above, another way for the user 1 to doff the garment body 2 is illustrated in FIG. 40. This method involves sequentially deactivating the garment-fitting actuators 5 of the garment body 2 to gradually loosen the garment body 2 beginning at the upper end portion 2a and proceeding toward the lower end portion 2c. That is, FIG. 40 illustrates a process reverse to the tightening process, in which after underpants as an example of the garment body 2 are put and tightened onto the user 1, the garment body 2 is loosened beginning at its upper end portion and proceeding toward the lower end portion. States (41) to (45) in the upper part of FIG. 40 each depict the outward appearance of the garment body 2, and States (51) to (55) in the lower part of FIG. 40 each depict the corresponding state of the garment-fitting actuators 5 of the garment body 2. States (41) to (45) are arranged in time series, and States (51) to (55) are arranged in time series. State (41) corresponds to State (51), State (42) corresponds to State (52), State (43) corresponds to State (53), State (44) corresponds to State (54), and State (45) corresponds to State (55). For States (51) to (55), dotted lines indicate the garment-fitting actuators 5 in an inactive and non-contracting state, and solid lines indicate the garment-fitting actuators 5 in an active and contracting state. When the garment-fitting actuators 5 are activated by the controller 8, the drive of the garment-fitting actuators 5 is controlled such that the garment-fitting actuators 5 contract gradually. Parts of the garment body 2 whose contours are represented by wavy lines indicate parts in a loose state. Parts of the garment body 2 whose contours are represented by straight lines indicate parts in a tightened state. Downward arrows indicate the direction in which the garment body 2 is changed from a tightened state to a loosened state.

States (41) and (51) in FIG. 40 represent the garment body 2 when put and then tightened onto the user 1, with the garment body 2 generally tightly fitting around the user 1. All of the garment-fitting actuators 5 are in an activated state at this point.

Next, in States (42) and (52) in FIG. 40, the garment-fitting actuators 5 in the upper end portion 2a of the garment body 2 are deactivated to extend by the controller 8 either sequentially or all at once to loosen the upper end portion 2a of the garment body 2. At this time, other portions of the garment body 2 are in a tightened state with the garment-fitting actuators 5 remaining in an activated state. Hereinafter, likewise for States (43) and (53), States (44) and (54), and States (45) and (55), only those portions of the garment body 2 in a loosened state will be described, and portions omitted in the following description are in a tightened state.

Next, in States (43) and (53) in FIG. 40, with the garment-fitting actuators 5 in the upper end portion 2a of the garment body 2 deactivated and loosened, the garment-fitting actuators 5 above the base portion 2b of the thigh area which is located further below the upper end portion 2a are deactivated to extend by the controller 8 either sequentially or all at once, thus loosening the garment body 2 down to the area further below the upper end portion 2a.

Next, in States (44) and (54) in FIG. 40, with the garment-fitting actuators 5 in the part of the garment body 2 from the upper end portion 2a to the area above the base portion 2b of the thigh area deactivated and loosened, the garment-fitting actuators 5 in the base portion 2b of the thigh area are deactivated to extend by the controller 8 either sequentially or all at once, thus loosening the part of the garment body 2 from the upper end portion 2a to the base portion 2b of the thigh area.

Next, in States (45) and (55) in FIG. 40, with the garment-fitting actuators 5 in the part of the garment body 2 from the upper end portion 2a to the area above the base portion 2b of the thigh area deactivated and loosened, the garment-fitting actuators 5 in the lower end portion 2c of the garment body 2 are deactivated to extend by the controller 8 either sequentially or all at once, thus loosening the part of the garment body 2 from the upper end portion 2a to the lower end portion 2c, that is, the entire garment body 2.

The series of operations above enables the garment body 2 to change gradually from a tight state to a loosened state while having its wrinkles smoothed out, beginning at the upper end portion 2a and proceeding toward the lower end portion 2c. This allows the user 1 to readily perceive that the garment body 2 is being loosened sequentially, allowing for easy doffing. This also helps eliminate slip-off of the garment body unintended by the user 1.

The garment body 2 may not necessarily be doffed in the manner mentioned above. Conversely, the garment-fitting actuators 5 of the garment body 2 may be deactivated sequentially for gradual loosening from the lower end portion 2c toward the upper end portion 2a to achieve the same operational effect as above.

Figure 41:
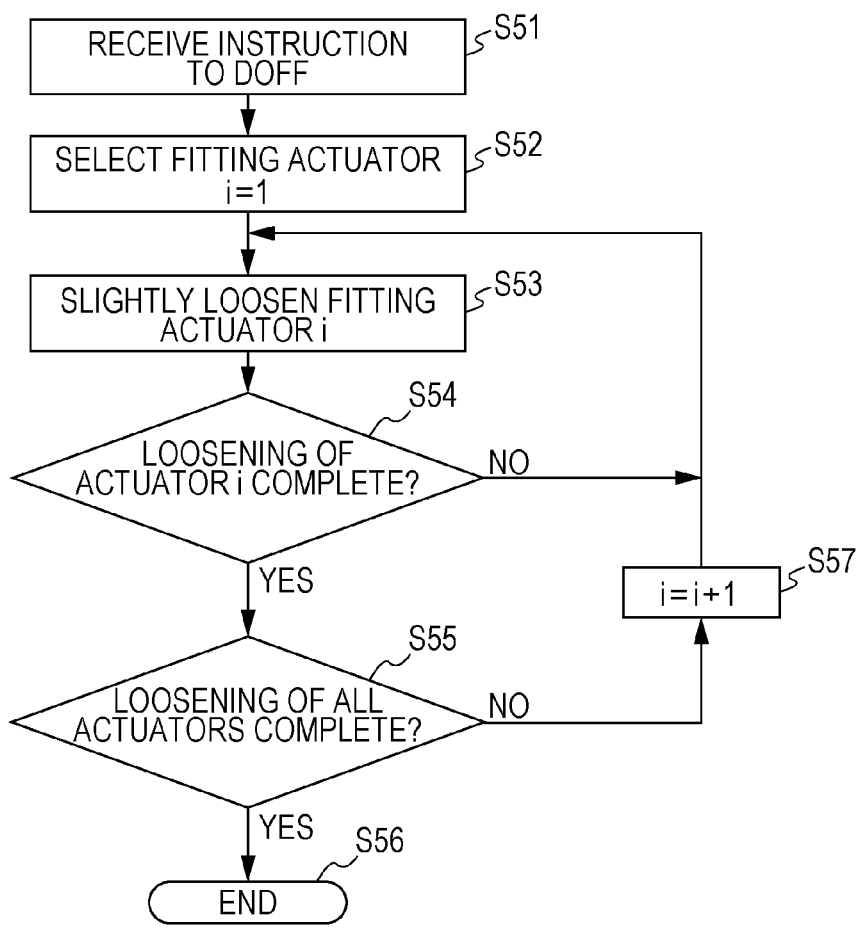
FIG. 41 is a flowchart illustrating doffing of a garment body.

Operating Procedure for Garment-Fitting Actuators During Doffing of Garment Body FIG. 41 is a flowchart illustrating doffing of the garment body 2.

Next, an operating procedure for the garment-fitting actuators during the doffing of the garment body will be described with reference to FIG. 41.

First, in step S51, the processing waits until a doffing start signal for the garment body 2 is input to the input/output device 16. Upon input of a doffing start signal to the controller 8, the processing proceeds to step S52.

Next, in step S52, the (i=1)-th garment-fitting actuator 5 is selected by the controller 8 as the target garment-fitting actuator 5.

Next, in step S53, under the control of the controller 8, deactivation of the (i=1)-th garment-fitting actuator 5 selected by the controller 8 is started, and the (i=1)-th garment-fitting actuator 5 is extended slightly to start untightening.

Next, in step S54, the controller 8 determines whether extension of the (i=1)-th garment-fitting actuator 5 is completed based on information from the sensor 7 such as the axial-force sensor 7A or the perpendicular-force sensor 7B. If the controller 8 determines that extension of the (i=1)-th garment-fitting actuator 5 is not completed, the processing returns to step S53. If the controller 8 determines that extension of the (i=1)-th garment-fitting actuator 5 is completed, the processing proceeds to step S55.

Next, in step S55, the controller 8 determines whether deactivation, that is, extension of all of the garment-fitting actuators 5 is completed. If the controller 8 determines that extension of all of the garment-fitting actuators 5 is not completed, the processing proceeds to step S57. If the controller 8 determines that extension of all of the garment-fitting actuators 5 is completed, the processing proceeds to step S56 where the processing ends.

In step S57, after the (i=i+1)-th garment-fitting actuator 5 is selected by the controller 8 as the target garment-fitting actuator 5, the processing proceeds to step S53. The (i=i+1)-th garment-fitting actuator 5 may be the garment-fitting actuator 5 adjacent to the (i=1)-th garment-fitting actuator 5. The (i=1)-th garment-fitting actuator 5 may be the garment-fitting actuator 5 in the uppermost end portion of the garment body 2 or the garment-fitting actuator 5 in the lowermost end portion.

With this manner of processing, the garment-fitting actuators 5 arranged in order from the upper end portion 2_a_ of the garment body 2 toward the lower end portion 2_c_ or from the lower end portion 2_c_ toward the upper end portion 2_a_ can be deactivated sequentially one by one.

Measures to Address Wrinkling

Figure 42:
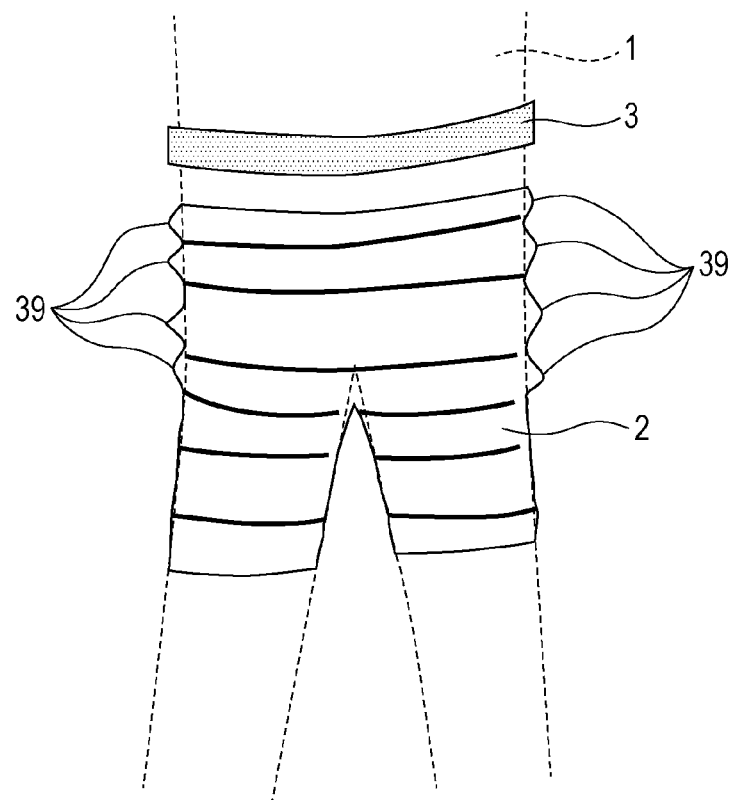
FIG. 42 illustrates a garment body on which wrinkles have formed.
Figure 43:
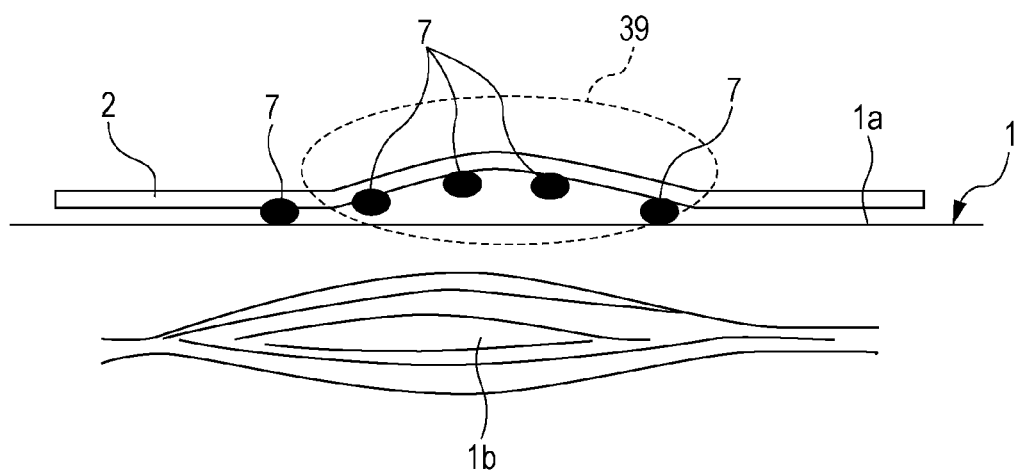
FIG. 43 is a cross-sectional view of a garment body on which wrinkles have formed.
Figure 44A:
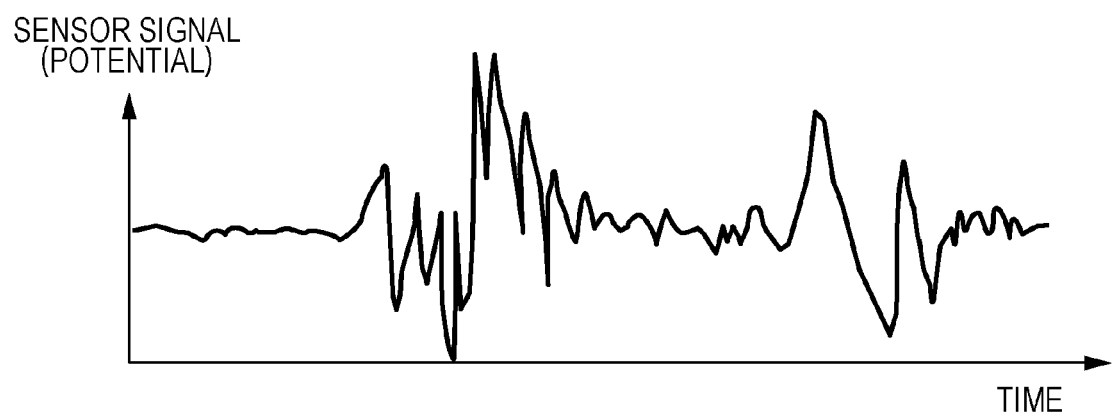
FIG. 44A illustrates sensor output in normal conditions.
Figure 44B:
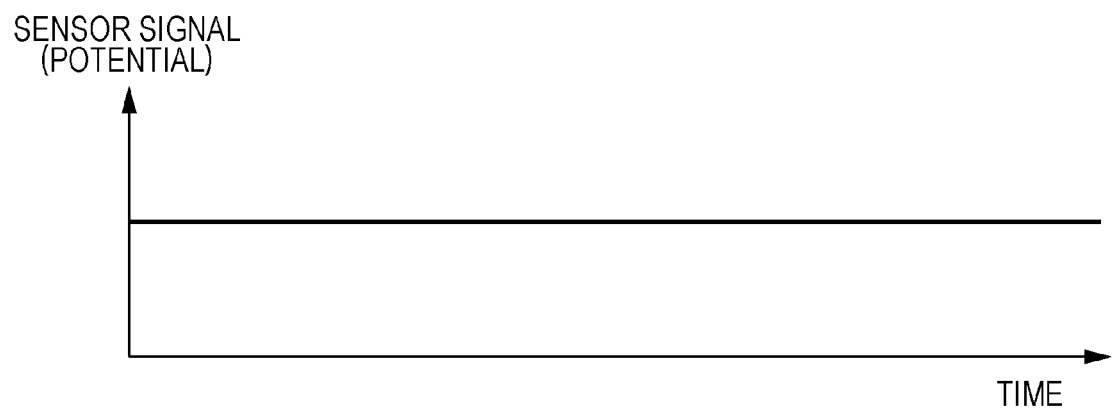
FIG. 44B illustrates sensor output when wrinkles have formed on a garment body.

FIGS. 42 and 43 are respectively an explanatory view and a cross-sectional view of the garment body 2 on which wrinkles 39 have formed. FIGS. 44A and 44B respectively illustrate sensor output in normal conditions and sensor output when the wrinkles 39 have formed on the garment body 2.

The following describes a process performed if the wrinkles 39 form on the garment body 2 when the garment body 2 is donned on the user 1.

Suppose that, upon donning the garment body 2 on the user 1, the wrinkles 39 form on an area of the garment body 2 from the upper end portion to the vicinity of the base portion 2_b_ of the thigh area as illustrated in FIG. 42. In this case, the sensors 7 are not in contact with skin 1_a_ of the user 1 in the area of the wrinkles 39 as illustrated in FIG. 43. The sensors 7 in such a wrinkled area may not be able to detect a biosignal such as an EMG. FIG. 44A illustrates an output signal of the sensor 7 when the sensor 7 is in contact with the skin 1_a_ of the user 1. FIG. 44B illustrates an output signal of the sensor 7 when the sensor 7 is not in contact with the skin 1_a_ of the user 1, indicating that no signal is output in this case.

A process of automatically detecting such formation of the wrinkles 39 will be described with reference to FIG. 45.

Figure 45:
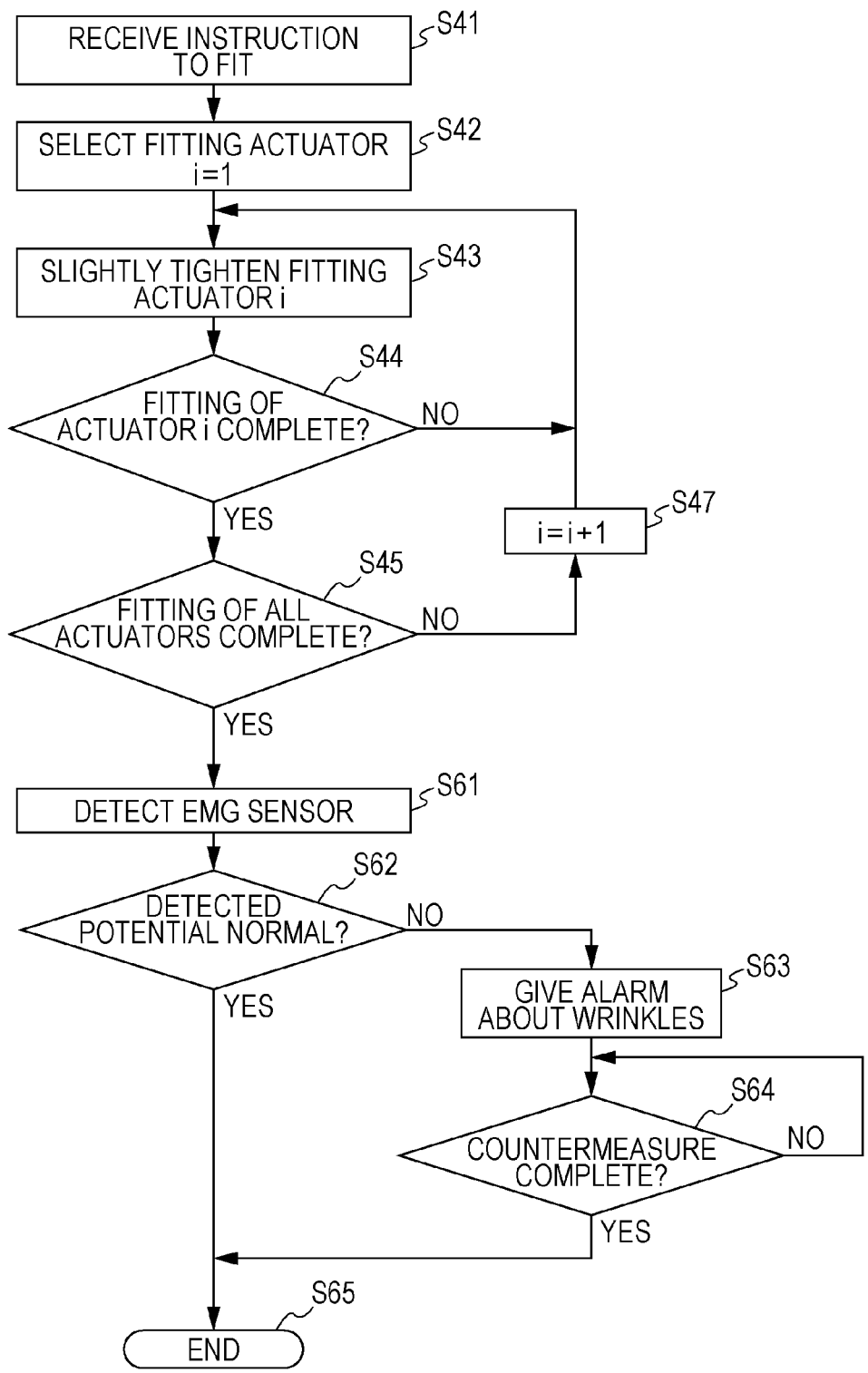
FIG. 45 is a flowchart illustrating a process of automatically detecting formation of wrinkles.
Figure 46A:
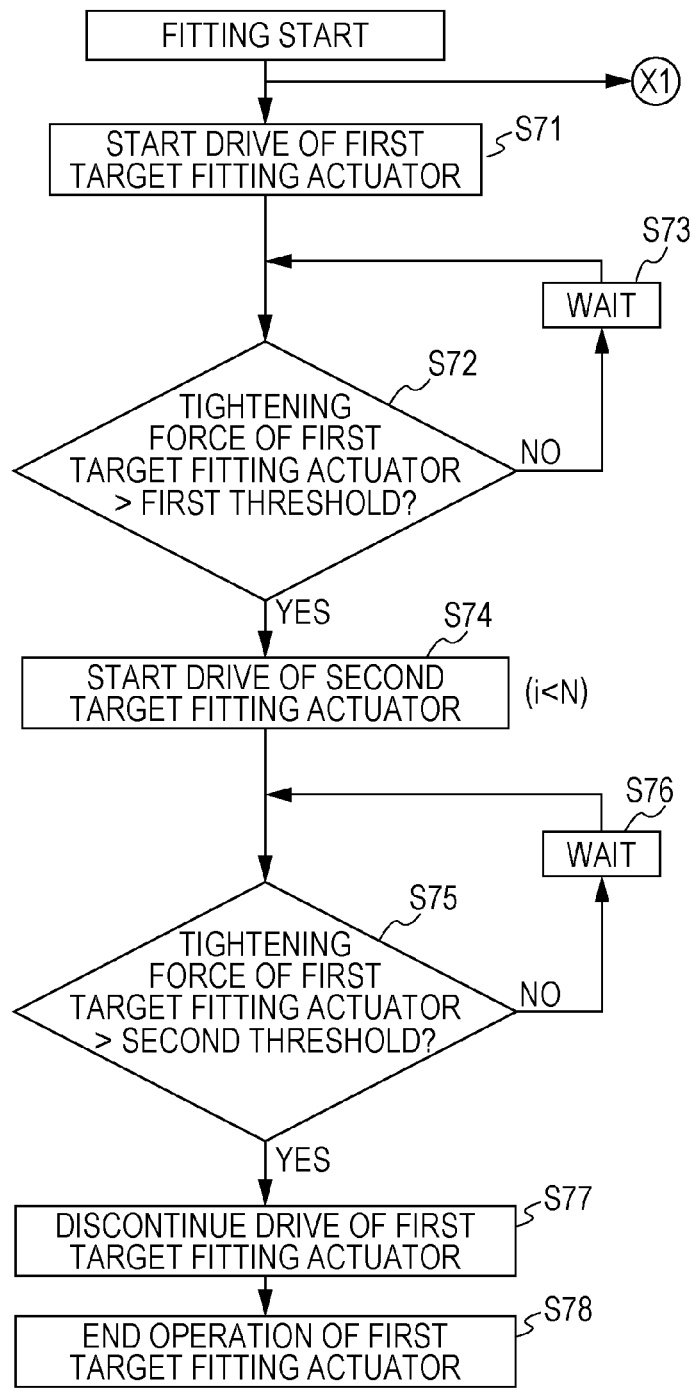
FIG. 46A is a flowchart of a process of sequentially driving garment-fitting actuators with a time lag.
Figure 46B:
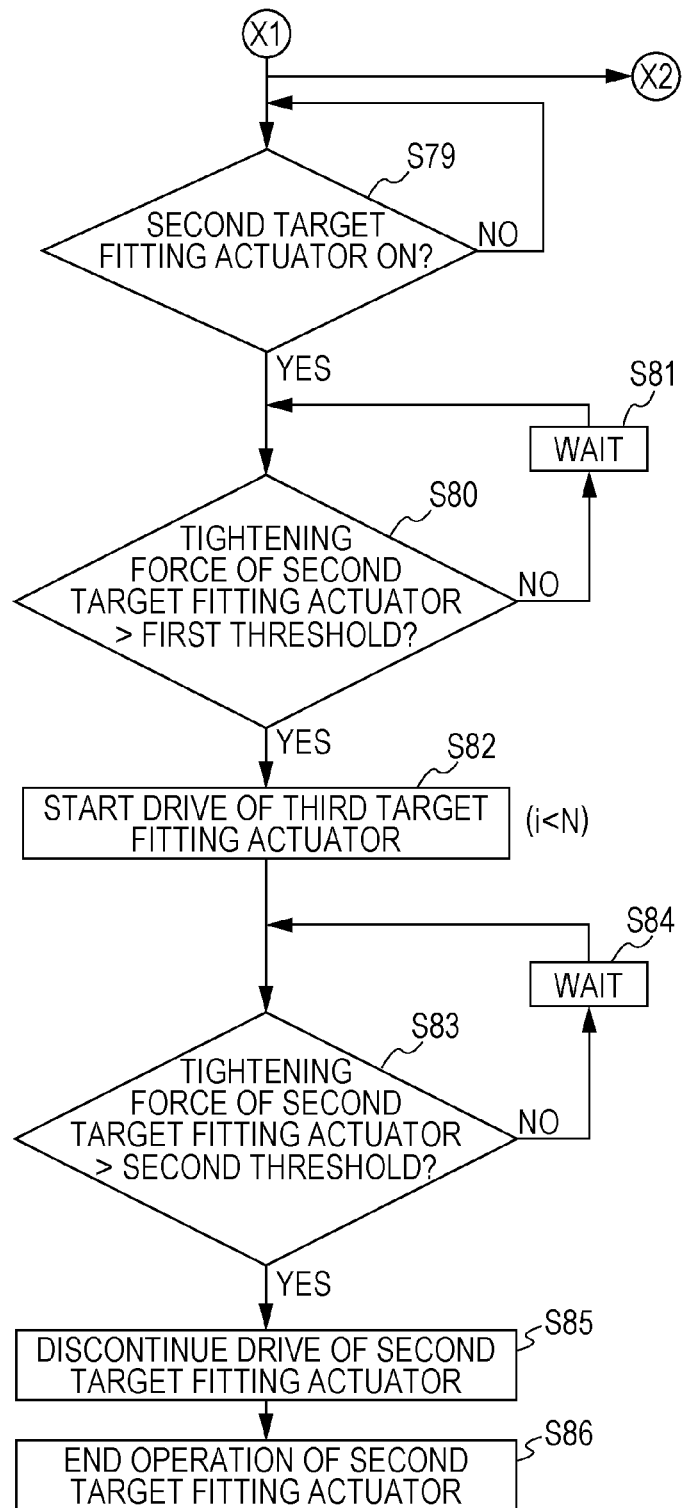
FIG. 46B is a flowchart, continuing from FIG. 46A, of a process of sequentially driving garment-fitting actuators with a time lag.
Figure 46C:
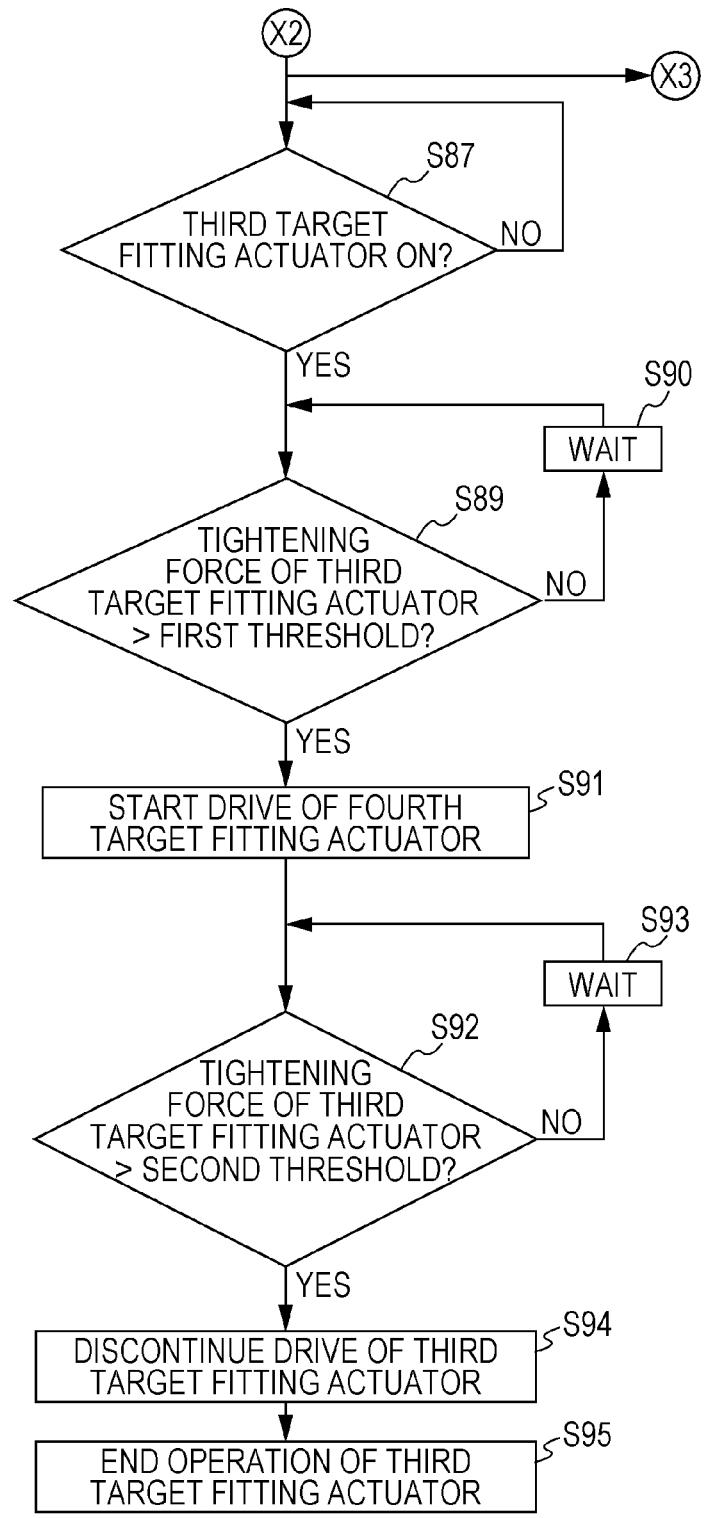
FIG. 46C is a flowchart, continuing from FIG. 46B, of a process of sequentially driving garment-fitting actuators with a time lag.
Figure 46D:
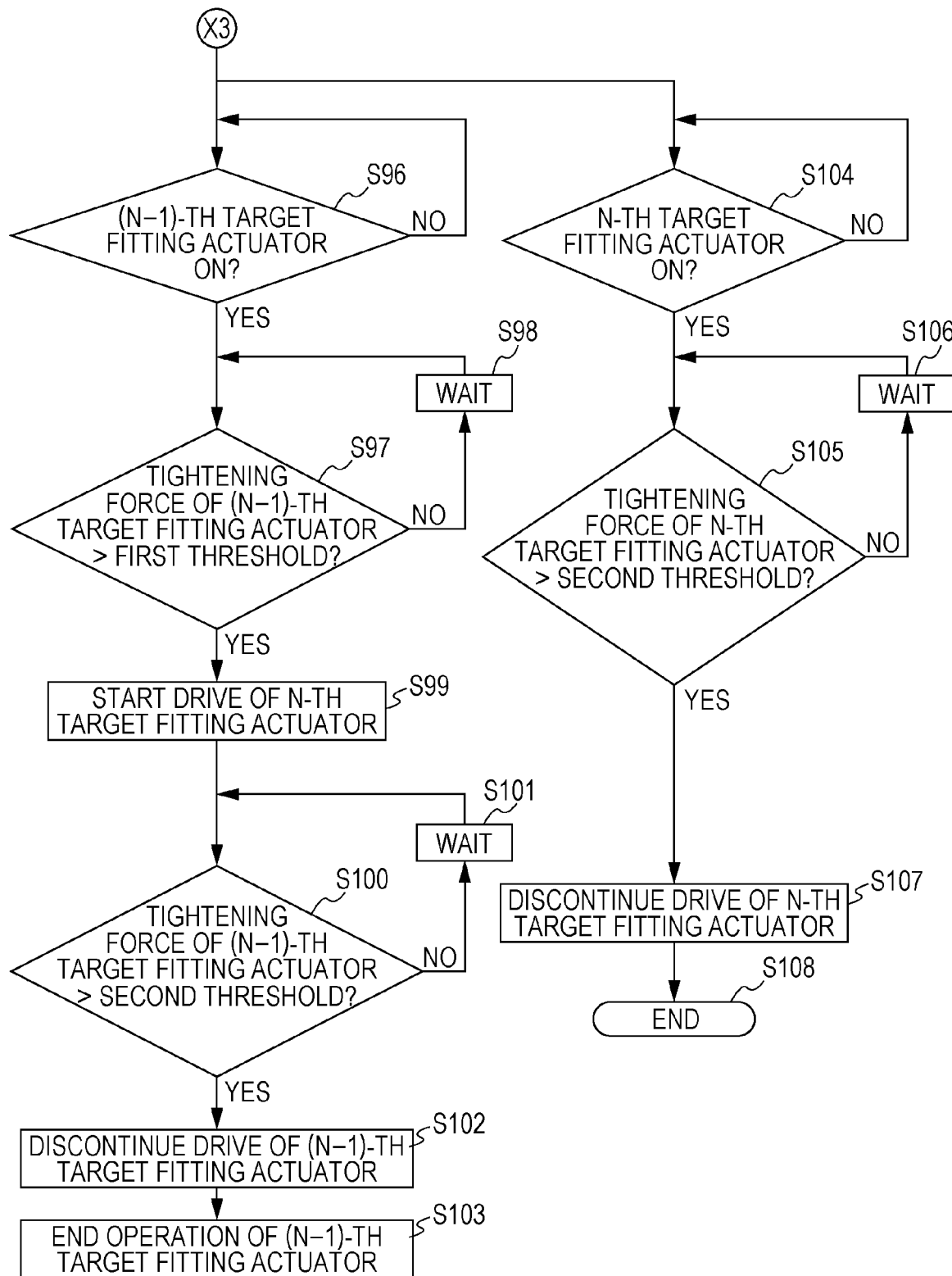
FIG. 46D is a flowchart, continuing from FIG. 46C, of a process of sequentially driving garment-fitting actuators with a time lag.

In FIG. 45, steps S41 to S45 and step S47 are performed in the same manner as steps S41 to S45 and step S47 in FIG. 38. That is, after finishing the operating procedure for the garment-fitting actuators 5 during the donning of the garment body 2 illustrated in FIG. 38, the outputs of all of the sensors 7 are detected by the controller 8 in step S61.

Next, in step S62, the controller 8 determines whether a detected potential is normal based on the output from each of the sensors 7. For example, if the sensor 7 is an EMG sensor, the controller 8 determines whether an EMG signal is generated in response to the motion of the user 1 (i.e., whether the detected potential is normal). The determination of whether the detected potential is normal may be made as follows. For example, the controller 8 determines the detected potential to be not normal if the output from the sensor 7 is below or equal to an error detection threshold. If the controller 8 determines that the detected potential is normal, the processing ends in step S65. If the controller 8 determines that the detected potential is not normal, the processing proceeds to step S63.

In step S63, an alarm indicating the presence of the wrinkles 39 is given through, for example, the speaker, display, or vibrator of the input/output device 16 under the control of the controller 8. An example of the vibrator may be a known vibrator specifically provided for this purpose. Alternatively, the garment-fitting actuators may be extended and contracted in small increments under the control of the controller 8 to generate vibrations.

Next, in step S64, the controller 8 determines whether a countermeasure is completed. If a countermeasure is completed, the processing ends in step S65. If a countermeasure is not completed, the alarm is continued to be generated. One example of such a countermeasure is straightening of the areas of the wrinkles 39 by the user 1 with the hand to remove the wrinkles 39, thus bringing all of the sensors 7 into contact with the skin 1_a_. Another example of such a countermeasure is to operate the input/output device 16 to temporarily deactivate the garment-fitting actuators 5 in regions of the garment body 2 with the wrinkles 39 via the controller 8, and then activate the garment-fitting actuators 5 again to remove the wrinkles 39. Either of these two methods may be performed to remove the wrinkles 39 so that the controller 8 determines that the detected potential has become normal. Alternatively, the user 1 may operate the input/output device 16 to input a countermeasure completion signal to the controller 8.

Advantages

In related art, wrinkles or the like that may form on a garment upon donning the garment on the human body cause the garment to lift off the body, creating a gap between the garment and the body which leads to an improper fit. Such an improper fit impedes proper transmission of force from the actuators on the garment to the body, leading to improper assist.

In the first embodiment, the assisting actuators 6 are activated after the garment body 2 is fit onto the user 1 using the garment-fitting actuators 5. This ensures reliable transmission of assist force from the assisting actuators 6 to the user 1, allowing for proper assist. That is, the garment-fitting actuators 5 are used to change the fit of the garment body 2 from loose to tight, allowing the garment body 2 to properly fit onto the user 1. This proper fit allows the assist force from the assisting actuators 6 to be properly exerted on, for example, the muscle 1_b_ of the user 1.

Modification 1 of Garment Donning Operation

Figure 47:
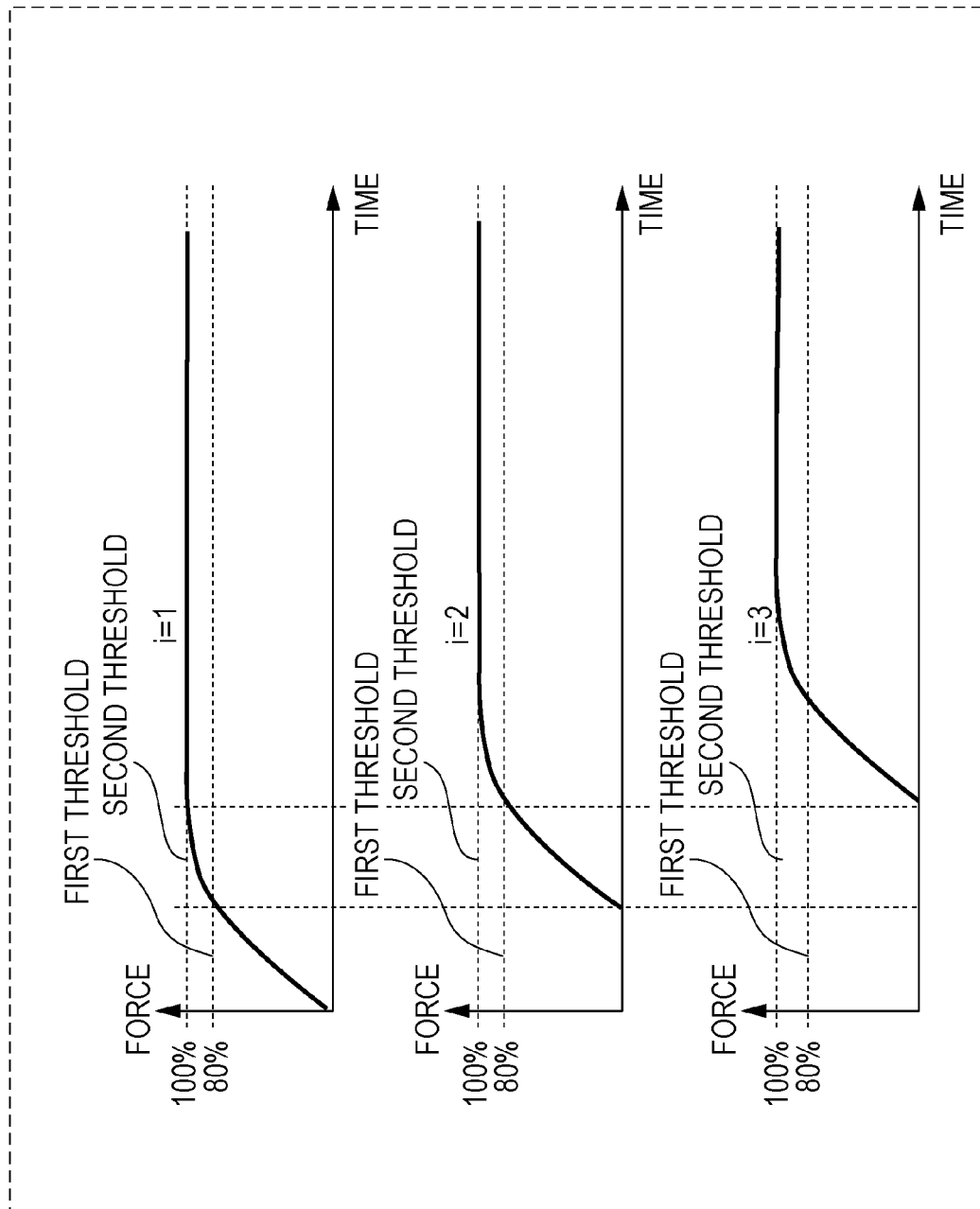
FIG. 47 illustrates the relationship between the tightening force exerted by each garment-fitting actuator and associated thresholds, in a process of sequentially driving the garment-fitting actuators with a time lag.

As examples of the operating procedure for the garment-fitting actuators 5 during the donning of the garment body 2, two methods have been described above, one that drives the garment-fitting actuators 5 one by one and the other that drives the garment-fitting actuators 5 simultaneously. In a still another example of such a procedure, the garment-fitting actuators 5 may be driven sequentially with a time lag. FIGS. 46A to 46D are flowcharts of a process of sequentially driving the garment-fitting actuators 5 with a time lag. FIG. 47 illustrates the relationship between the tightening force exerted by each of the garment-fitting actuators 5 and associated thresholds at that time.

Hereinafter, Modification 1 will be described with reference to FIGS. 46A to 46D. First, in step S71, for example, the drive of the first target garment-fitting actuator 5 is started under the control of the controller 8. At this time, for example, voltage is applied to the first target garment-fitting actuator 5 under the control of the controller 8.

Next, in step S72, the tightening force generated by a contraction caused by the drive of the first target garment-fitting actuator 5 is detected by the sensor 7 such as the axial-force sensor 7A or the perpendicular-force sensor 7B, and the controller 8 determines whether the magnitude of the detected force exceeds the first threshold. If the controller 8 determines that the tightening force does not exceed the first threshold, the drive is continued for a predetermined period of time in step S73. Subsequently, again in step S72, the controller 8 determines whether the tightening force exceeds the first threshold. If the controller 8 determines that the tightening force exceeds the first threshold, the processing proceeds to step S74.

Next, in step S74, the drive of, for example, the second target garment-fitting actuator 5 is started under the control of the controller 8. This means to start the drive of the second target garment-fitting actuator 5 after the magnitude of the tightening force exerted by the first target garment-fitting actuator 5 becomes equal to or greater than a predetermined value.

Next, in step S75, the tightening force generated by a contraction caused by the drive of the first target garment-fitting actuator 5 is detected by the sensor 7 such as the axial-force sensor 7A or the perpendicular-force sensor 7B, and the controller 8 determines whether the magnitude of the detected force exceeds the second threshold. If the controller 8 determines that the tightening force does not exceed the second threshold, the drive is continued for a predetermined period of time in step S76. Subsequently, again in step S75, the controller 8 determines whether the tightening force exceeds the second threshold. If the controller 8 determines that the tightening force exceeds the second threshold, the processing proceeds to step S77.

Next, in step S77, the drive of the first target garment-fitting actuator 5 is discontinued under the control of the controller 8. Thus, the drive operation of the first target garment-fitting actuator 5 ends in step S78. This means to discontinue, after the drive of the second target garment-fitting actuator 5 is started, the drive of the first target garment-fitting actuator 5 once the tightening force exerted by the first target garment-fitting actuator 5 reaches a predetermined value. The expression "discontinue the drive" as used herein means that "the controller 8 controls the tightening force of the first target garment-fitting actuator 5 to be maintained at a predetermined value".

Meanwhile, in step S79, the controller 8 determines whether the drive of the second target garment-fitting actuator 5 has been started while the series of steps S71 to S77 is executed. If the drive of the second target garment-fitting actuator 5 has not been started yet, the processing waits until the drive of the second target garment-fitting actuator 5 is started. Once the drive of the second target garment-fitting actuator 5 is started in response to step S74, the processing proceeds to step S80.

In step S80, the tightening force generated by a contraction due to the drive of the second target garment-fitting actuator 5 is detected by the sensor 7 such as the axial-force sensor 7A or the perpendicular-force sensor 7B, and the controller 8 determines whether the magnitude of the detected force exceeds the first threshold. If the controller 8 determines that the tightening force does not exceed the first threshold, the drive is continued for a predetermined period of time in step S81. Subsequently, again in step S80, the controller 8 determines whether the tightening force exceeds the first threshold. If the controller 8 determines that the tightening force exceeds the first threshold, the processing proceeds to step S82.

Next, in step S82, the drive of, for example, the third target garment-fitting actuator 5 is started under the control of the controller 8. This means to start the drive of the third target garment-fitting actuator 5 after the magnitude of the tightening force exerted by the second target garment-fitting actuator 5 becomes equal to or greater than a predetermined value.

Next, in step S83, the tightening force generated by a contraction due to the drive of the second target garment-fitting actuator 5 is detected by the sensor 7 such as the axial-force sensor 7A or the perpendicular-force sensor 7B, and the controller 8 determines whether the magnitude of the detected force exceeds the second threshold. If the controller 8 determines that the tightening force does not exceed the second threshold, the drive is continued for a predetermined period of time in step S84. Subsequently, again in step S83, the controller 8 determines whether the tightening force exceeds the second threshold. If the controller 8 determines that the tightening force exceeds the second threshold, the processing proceeds to step S85.

Next, in step S85, the drive of the second target garment-fitting actuator 5 is discontinued under the control of the controller 8. Thus, the drive operation of the second target garment-fitting actuator 5 ends in step S86. This means to discontinue, after the drive of the third target garment-fitting actuator 5 is started, the drive of the second target garment-fitting actuator 5 once the tightening force exerted by the second target garment-fitting actuator 5 reaches a predetermined value. The expression "discontinue the drive" as used herein means that "the controller 8 controls the tightening force of the second target garment-fitting actuator 5 to be maintained at a predetermined value".

In step S87, the controller 8 determines whether the drive of the third target garment-fitting actuator 5 has been started while the series of steps S71 to S86 is executed. If the drive of the third target garment-fitting actuator 5 has not been started yet, the processing waits until the drive of the third target garment-fitting actuator 5 is started. Once the drive of the third target garment-fitting actuator 5 is started in response to step S82, the processing proceeds to step S88.

Next, in step S89, the tightening force generated by a contraction due to the drive of the third target garment-fitting actuator 5 is detected by the sensor 7 such as the axial-force sensor 7A or the perpendicular-force sensor 7B, and the controller 8 determines whether the magnitude of the detected force exceeds the first threshold. If the controller 8 determines that the tightening force does not exceed the first threshold, the drive is continued for a predetermined period of time in step S90. Subsequently, again in step S89, the controller 8 determines whether the magnitude of the detected force exceeds the first threshold. If the controller 8 determines that the tightening force exceeds the first threshold, the processing proceeds to step S91.

Next, in step S91, the drive of, for example, the fourth target garment-fitting actuator 5 is started under the control of the controller 8. This means to start the drive of the fourth target garment-fitting actuator 5 after the magnitude of the tightening force exerted by the third target garment-fitting actuator 5 becomes equal to or greater than a predetermined value.

Next, in step S92, the tightening force generated by a contraction due to the drive of the third target garment-fitting actuator 5 and detected by the sensors 7 exceeds the second threshold. If the controller 8 determines that the tightening force does not exceed the second threshold, the drive is continued for a predetermined period of time in step S93. Subsequently, again in step S92, the controller 8 determines whether the tightening force exceeds the second threshold. If the controller 8 determines that the tightening force exceeds the second threshold, the processing proceeds to step S94.

Next, in step S94, the drive of the third target garment-fitting actuator 5 is discontinued under the control of the controller 8. Thus, the drive operation of the third target garment-fitting actuator 5 ends in step S95. This means to discontinue, after the drive of the fourth target garment-fitting actuator 5 is started, the drive of the third target garment-fitting actuator 5 once the tightening force exerted by the third target garment-fitting actuator 5 reaches a predetermined value. The expression "discontinue the drive" as used herein means that "the controller 8 controls the tightening force of the third target garment-fitting actuator 5 to be maintained at a predetermined value".

Thereafter, likewise for a total of N garment-fitting actuators 5, in step S96, the controller 8 determines whether the drive of the (N−1)-th target garment-fitting actuator 5 has been started while the series of steps preceding step S96 is executed. If the drive of the (N−1)-th target garment-fitting actuator 5 has not been started yet, the processing waits until the drive of the (N−1)-th target garment-fitting actuator 5 is started. Once the drive of the (N−1)-th target garment-fitting actuator 5 is started, the processing proceeds to step S97.

In step S97, the tightening force generated by a contraction due to the drive of the (N−1)-th target garment-fitting actuator 5 is detected by the sensor 7 such as the axial-force sensor 7A or the perpendicular-force sensor 7B, and the controller 8 determines whether the magnitude of the detected force exceeds the first threshold. If the controller 8 determines that the tightening force does not exceed the first threshold, the drive is continued for a predetermined period of time in step S98. Subsequently, again in step S97, the controller 8 determines whether the magnitude of the detected force exceeds the first threshold. If the controller 8 determines that the tightening force exceeds the first threshold, the processing proceeds to step S99.

Next, in step S99, the drive of the N-th target garment-fitting actuator 5 is started under the control of the controller 8. This means to start the drive of the N-th target garment-fitting actuator 5 after the magnitude of the tightening force exerted by the (N−1)-th target garment-fitting actuator 5 becomes equal to or greater than a predetermined value.

Next, in step S100, the tightening force generated by a contraction due to the drive of the (N−1)-th target garment-fitting actuator 5 is detected by the sensor 7 such as the axial-force sensor 7A or the perpendicular-force sensor 7B, and the controller 8 determines whether the magnitude of the detected force exceeds the second threshold. If the controller 8 determines that the tightening force does not exceed the second threshold, the drive is continued for a predetermined period of time in step S101. Subsequently, again in step S100, the controller 8 determines whether the magnitude of the detected force exceeds the second threshold. If the controller 8 determines that the tightening force exceeds the second threshold, the processing proceeds to step S102.

Next, in step S102, the drive of the (N−1)-th target garment-fitting actuator 5 is discontinued under the control of the controller 8. Thus, the drive operation of the (N−1)-th target garment-fitting actuator 5 ends in step S103. This means to discontinue, after the drive of the N-th target garment-fitting actuator 5 is started, the drive of the (N−1)-th target garment-fitting actuator 5 once the tightening force exerted by the (N−1)-th target garment-fitting actuator 5 reaches a predetermined value. The expression "discontinue the drive" as used herein means that "the controller 8 controls the tightening force of the (N−1)-th target garment-fitting actuator 5 to be maintained at a predetermined value".

In step S104, the controller 8 determines whether the drive of the N-th target garment-fitting actuator 5 has been started while the series of steps preceding step S104 is executed. If the drive of the second target garment-fitting actuator 5 has not been started yet, the processing waits until the drive of the N-th target garment-fitting actuator 5 is started. Once the drive of the N-th target garment-fitting actuator 5 is started, the processing proceeds to step S105.

In step S105, the tightening force generated by a contraction due to the drive of the N-th target garment-fitting actuator 5 is detected by the sensor 7 such as the axial-force sensor 7A or the perpendicular-force sensor 7B, and the controller 8 determines whether the magnitude of the detected force exceeds the second threshold. If the controller 8 determines that the tightening force does not exceed the second threshold, the drive is continued for a predetermined period of time in step S106. Subsequently, again in step S105, the controller 8 determines whether the tightening force exceeds the second threshold. If the controller 8 determines that the tightening force exceeds the second threshold, the processing proceeds to step S107.

Next, in step S107, the drive of the N-th target garment-fitting actuator 5 is discontinued under the control of the controller 8. Thus, the drive operation of the N-th garment-fitting actuator 5 ends in step S108. This means to discontinue the drive of the N-th, that is, the last target garment-fitting actuator 5 once the tightening force exerted by the N-th target garment-fitting actuator 5 reaches a predetermined value. The expression "discontinue the drive" as used herein means that "the controller 8 controls the tightening force of the N-th target garment-fitting actuator 5 to be maintained at a predetermined value".

An example of the first threshold is 80% of a predetermined value, and an example of the second threshold is 100% of the predetermined value. FIG. 47 is a graph illustrating the drive state at this time. The graph illustrates that the first to third target garment-fitting actuators 5 are driven sequentially with a time lag.

This configuration allows the target garment-fitting actuators 5 to be driven sequentially with a time lag, from the first to N-th garment-fitting actuators 5. Compared to driving a large number of garment-fitting actuators 5 one by one, this configuration allows the fitting operation to be completed in a shorter time without causing the wrinkles 39.

In the first embodiment, the fitting of the garment body 2 is performed beginning at its one end and processing toward the other end. Alternatively, the fitting may be performed initially in the middle, and then proceeds toward both ends simultaneously. This further reduces the time required for the fitting operation.

Modification 2 of Garment Donning Operation

Next, a modification of how to handle errors during the donning of the garment body will be described. In the donning procedure illustrated in FIGS. 37 and 38, wrinkle detection is performed after the fitting of the garment-fitting actuators 5 is completed. Alternatively, during the donning of the garment, errors such as wrinkles may be detected during the course of fitting the garment body 2 sequentially from its one end, thus prompting the user 1 to take an appropriate measure such as smoothing out the wrinkles.

Figure 48:
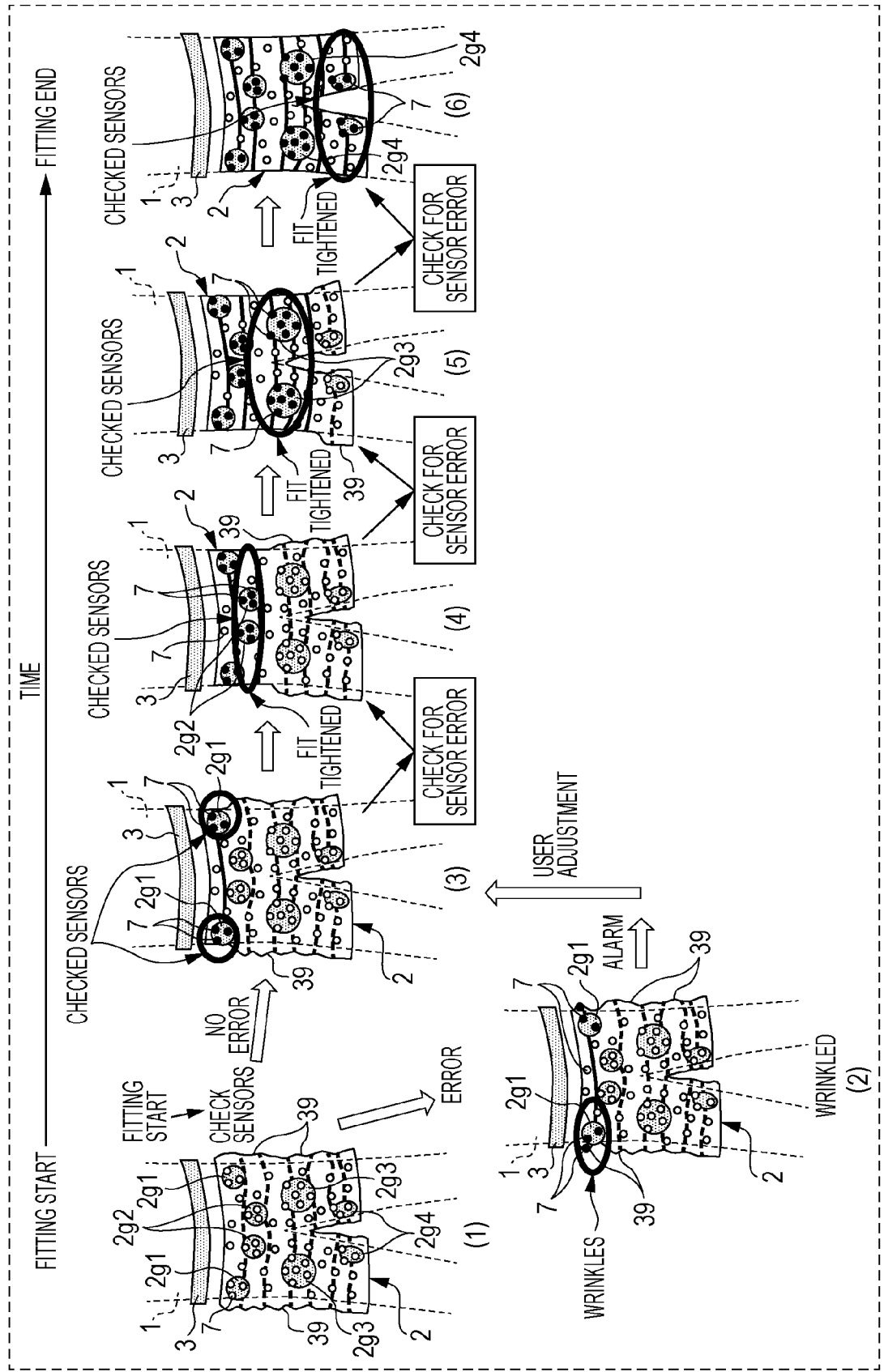
FIG. 48 illustrates a series of operations performed to retighten areas determined to have wrinkles by a controller during tightening operation.

This configuration is described below in detail with reference to FIG. 48. FIG. 48 illustrates a series of operations performed to retighten areas determined to have the wrinkles 39 by the controller 8 during tightening (fitting) operation. State (1) in FIG. 48 represents a state in which the user 1 is wearing the garment body 2, with the garment body 2 generally in a loose state. After this state, the garment-fitting actuators 5 in a location corresponding to a region 2g1 of the upper end portion of the garment body 2 are activated to tighten the garment body 2, and then the output of the sensor 7 in this region is detected by the controller 8 to determine the presence of the wrinkles 39.

If the wrinkles 39 are determined to exist by the controller 8, as illustrated as State (2) in FIG. 48, the garment-fitting actuators 5 in the region 2g1 of the upper end portion are deactivated and then activated again to perform retightening operation. Alternatively, an alarm indicating the presence of the wrinkles 39 is given through, for example, the speaker, display, or vibrator of the input/output device 16 under the control of the controller 8. Then, after the user 1 takes an appropriate measure such as removing the wrinkles 39 by, for example, pulling the garment body 2 with the hand, the output of the sensor 7 in this region may be detected by the controller 8 to determine the presence of the wrinkles 39. This wrinkle removal may be performed until the wrinkles are eliminated. Alternatively, if the wrinkles 39 remain after this operation is performed several times, an error indication may be displayed to prevent transition to the assist operation.

In FIG. 48, the sensors 7 in areas determined to be free of the wrinkles 39 by the controller 8 are indicated by black circles, and the sensors 7 in areas for which the presence of the wrinkles 39 has not been determined yet are indicated by white circles.

Once a measure such as removing the wrinkles 39 is taken, and the controller 8 detects the output of the sensor 7 in the corresponding region and determines that the region is now free of the wrinkles 39 (see State (3) in FIG. 48), tightening and determination of the presence of the wrinkles 39 are then performed sequentially for the next region $2g2$ of interest (see State (4) in FIG. 48). When this tightening and checking for the wrinkles 39 are performed sequentially for regions $2g3$ and $2g4$ and so on all the way down to the lower end portion $2c$ at the left and right of the garment body 2 (see States (5) and (6) in FIG. 48), the entire garment body 2 becomes free of the wrinkles 39 (see State (6) in FIG. 48).

Figure 49:
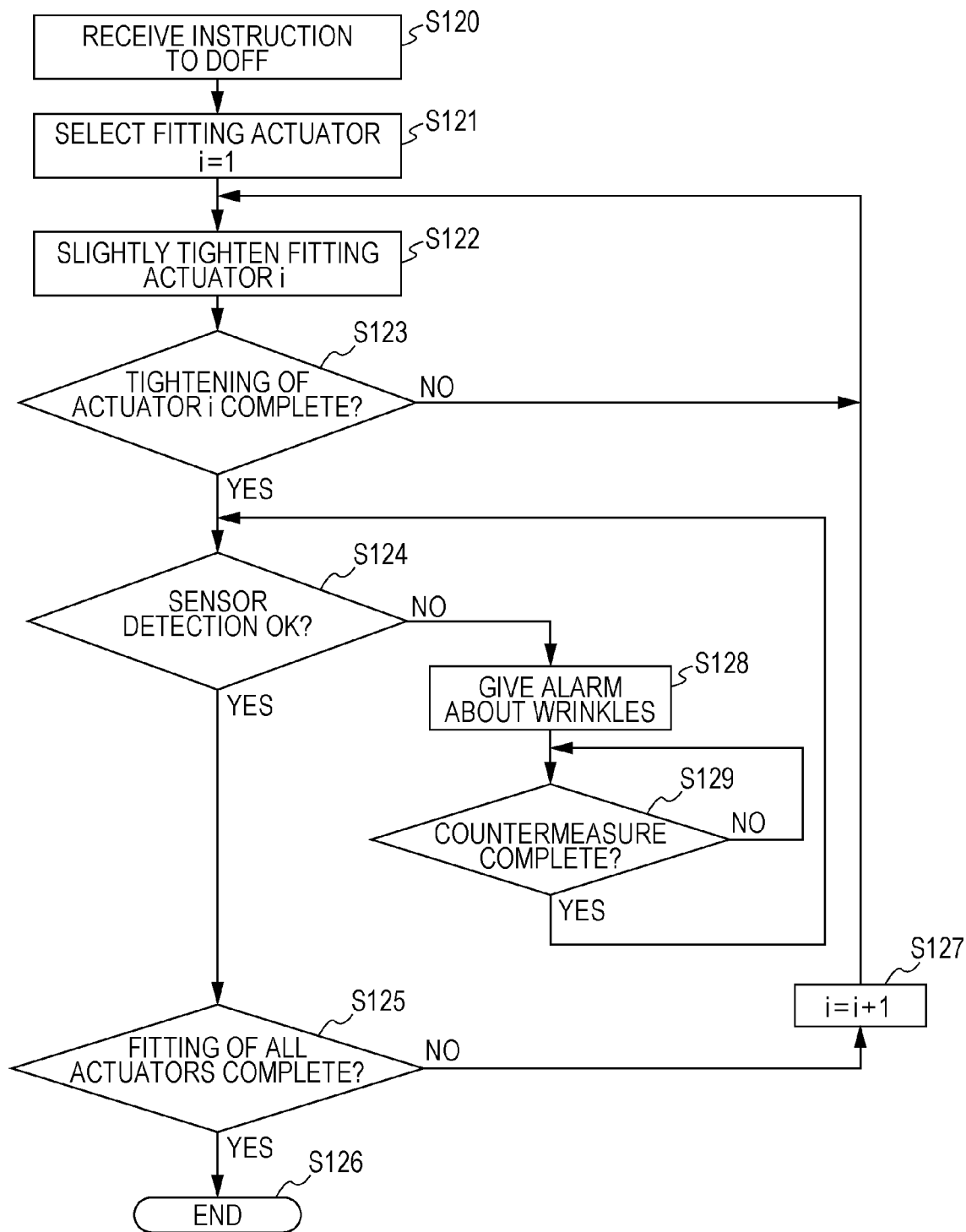
FIG. 49 is a flowchart illustrating a series of operations performed to retighten areas determined to have wrinkles by a controller during tightening operation.

Next, this series of operations will be described in detail with reference to FIG. 49.

First, in step S120, when the controller 8 receives an instruction from the user 1 to doff the garment body 2, the series of processes described below is started.

Next, in step S121, the (i=1)-th garment-fitting actuator 5 is selected by the controller 8 as the garment-fitting actuator 5 of interest.

Next, in step S122, under the control of the controller 8, the drive of the (i=1)-th garment-fitting actuator 5 selected by the controller 8 is started, and the (i=1)-th garment-fitting actuator 5 is contracted slightly to start tightening operation.

Next, in step S123, the controller 8 determines whether contraction of the (i=1)-th garment-fitting actuator 5 is completed. If the controller 8 determines that contraction of the (i=1)-th garment-fitting actuator 5 is not completed, the processing returns to step S122. If the controller 8 determines that contraction of the (i=1)-th garment-fitting actuator 5 is completed, the processing proceeds to step S124.

Next, in step S124, the controller 8 detects the output of the sensor 7. At this time, the controller 8 extracts only the output of the sensor 7 located within a region where the (i=1)-th garment-fitting actuator 5 is placed, and determines whether the detected potential is normal. Information for identifying each of the garment-fitting actuators 5, and information for identifying the sensor 7 corresponding to the garment-fitting actuator 5 may be stored in the memory $8a$ in advance. The controller 8 may then reference the stored information, and extract the output of a sensor corresponding to the garment-fitting actuator 5 of interest (the (i=1)-th garment-fitting actuator 5 in this example). For example, if the sensor 7 is an EMG sensor, the controller 8 determines whether an EMG signal is generated in response to the motion of the user 1. If the controller 8 determines that the detected potential is normal, the processing proceeds to step S125. If the controller 8 determines that the detected potential is not normal, the processing proceeds to step S128.

In step S128, an alarm indicating the presence of the wrinkles 39 is given through, for example, the speaker, display, or vibrator of the input/output device 16 under the control of the controller 8. In one exemplary embodiment, this alarm is given by notifying the information terminal 15 of the user 1 of the presence of the wrinkles 39 by using the speaker, the LED, or the radio communication unit of the input/output device 16. This alarm may be given to not only warn the user 1 of the wrinkles 39 that have formed but also notify the user 1 the location of the wrinkles 39 based on the output of the sensor 7.

Next, in step S129, the controller 8 determines whether a countermeasure is completed. If a countermeasure is completed, the processing returns to step S124. If a countermeasure is not completed, the alarm is continued to be generated. One example of such a countermeasure is straightening of the areas of the wrinkles 39 by the user 1 with the hand to remove the wrinkles 39, thus bringing all of the sensors 7 into contact with the skin $1a$. Another example of such a countermeasure is to operate the input/output device 16 to temporarily deactivate the garment-fitting actuators 5 placed in regions of the garment body 2 with the wrinkles 39 via the controller 8, and then activate the garment-fitting actuators 5 again to remove the wrinkles 39. For example, the garment body 2 may be divided in advance into the region ($2g1$) corresponding to the upper end portion $2a$, the region ($2g2$) between the upper end portion $2a$ and the base portion $2b$ of the thigh area, the region ($2g3$) corresponding to the base portion $2b$ of the thigh area, the region ($2g4$) corresponding to the lower end portion $2c$ on the left side, and the region ($2g4$) corresponding to the lower end portion $2c$ on the right side. Then, the garment-fitting actuators 5 in regions of the garment body 2 with the wrinkles 39 are temporarily deactivated and then activated again to remove the wrinkles 39. Either one of these methods may be performed to remove the wrinkles 39 so that the controller 8 determines that the detected potential has become normal. Alternatively, the user 1 may operate the input/output device 16 to input a countermeasure completion signal to the controller 8.

Next, in step S125, the controller 8 determines whether activation, that is, contraction of all of the garment-fitting actuators 5 is completed. If the controller 8 determines that contraction of all of the garment-fitting actuators 5 is not completed, the processing proceeds to step S127. If the controller 8 determines that contraction of all of the garment-fitting actuators 5 is completed, the processing proceeds to step S126 where the processing ends.

In step S127, after the (i=i+1)-th garment-fitting actuator 5 is selected by the controller 8 as the garment-fitting actuator 5 of interest, the processing returns to step S122. The (i=i+1)-th garment-fitting actuator 5 may be the garment-fitting actuator 5 adjacent to the (i=1)-th garment-fitting actuator 5. The (i=1)-th garment-fitting actuator 5 may be the garment-fitting actuator 5 in the uppermost end portion of the garment body 2 or the garment-fitting actuator 5 in the lowermost end portion.

The above configuration allows the user 1 to become aware of the wrinkles 39 immediately as soon as the wrinkles 39 form during garment donning. This allows the user 1 to immediately address the wrinkles 39 that have formed, without waiting for the completion of operation of all of the garment-fitting actuators 5, and also easily recognize where the problem has occurred.

Modifications

Although all of the garment-fitting actuators 5 are of the same structure and apply the same force in the first embodiment, this is not to be construed restrictively.

Figure 50:
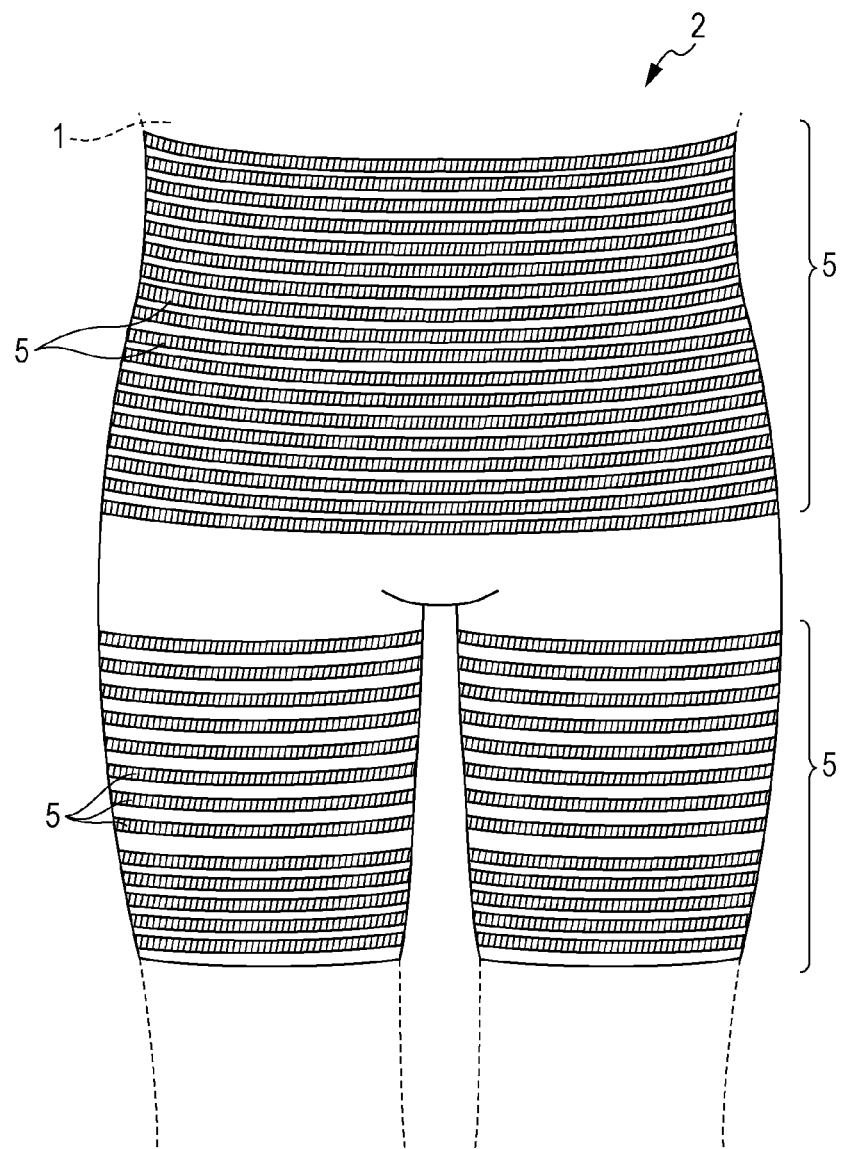
FIG. 50 illustrates placement of identical garment-fitting actuators across the entire garment body.

For example, FIG. 50 illustrates an exemplary arrangement in which the identical garment-fitting actuators 5 are placed across the entire garment body 2, with the garment-fitting actuators 5 placed at different densities for different locations on the garment body 2. This arrangement allows the garment body 2 to be tightened onto a part of the user 1 with a generally uniform force, making this arrangement suited for providing a uniform fit.

This configuration ensures uniform contact of all of the sensors 7, allowing stable measurement. This configuration proves particularly effective for, for example, the first structural example 45 of the garment body 2 illustrated in FIG. 23.

Figure 51:
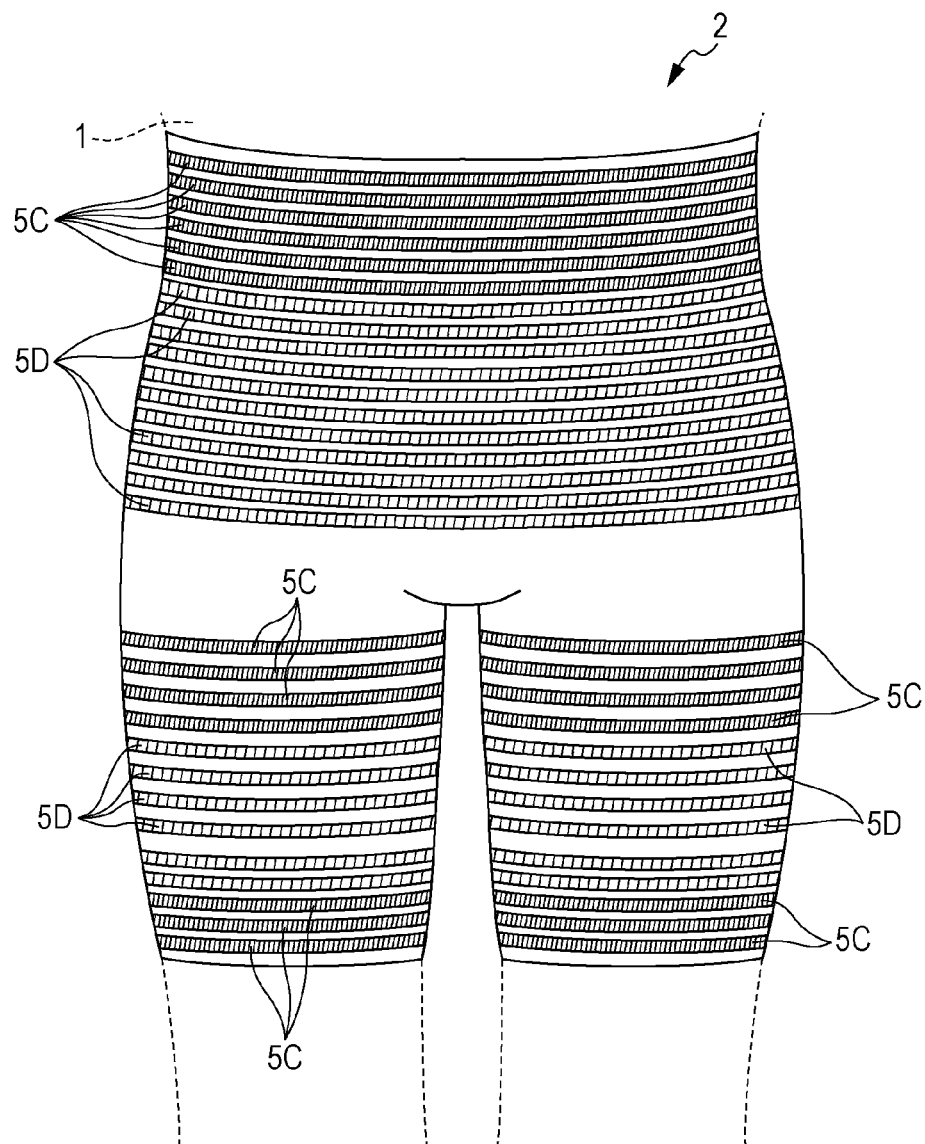
FIG. 51 illustrates placement of two kinds of garment-fitting actuators on a garment body.

FIG. 51 illustrates use of the garment-fitting actuators 5 capable of applying a relatively large tightening force and the garment-fitting actuators 5 capable of applying a relatively small tightening force. In one example, two kinds of garment-fitting actuators 5C and 5D are placed. The garment-fitting actuators 5C are capable of exerting 100% tension upon contraction. The garment-fitting actuators 5D are capable of exerting 60% tension upon contraction. Specifically, the garment-fitting actuators 5C capable of exerting 100% tension upon contraction are placed in the upper end portion 2a of the garment body 2, the base portion 2b of the thigh area, and the lower end portion 2c of the garment body 2 to provide a tight fit. In contrast, the garment-fitting actuators 5D capable of exerting 60% tension upon contraction tension are placed in the part between the upper end portion 2a of the garment body 2 and the base portion 2b of the thigh area, and the part between the base portion 2b of the thigh area and the lower end portion 2c of the garment body 2 to provide a somewhat loose fit.

With this configuration, the garment-fitting actuators 5C are used to secure the garment body 2 in place focusing on those areas necessary for restraining the movement of the assisting actuators 6 to prevent displacement, and for other areas, the garment-fitting actuators 5D are used to provide a loose fit to facilitate extension and contraction of the assisting actuators 6. This configuration proves particularly effective for, for example, the third structural example 65 of the garment body 2 illustrated in FIG. 25.

Modifications

Figure 52:
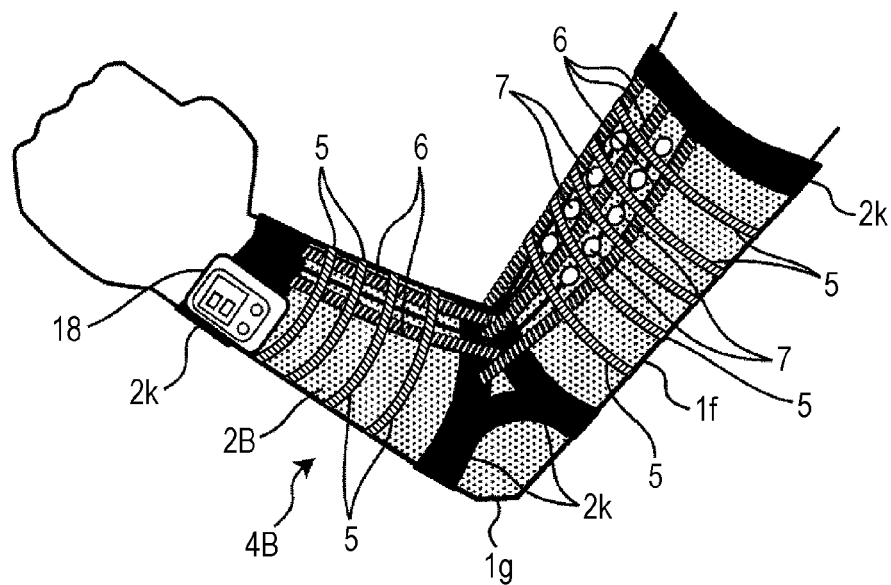
FIG. 52 illustrates an elbow assist garment.
Figure 53:
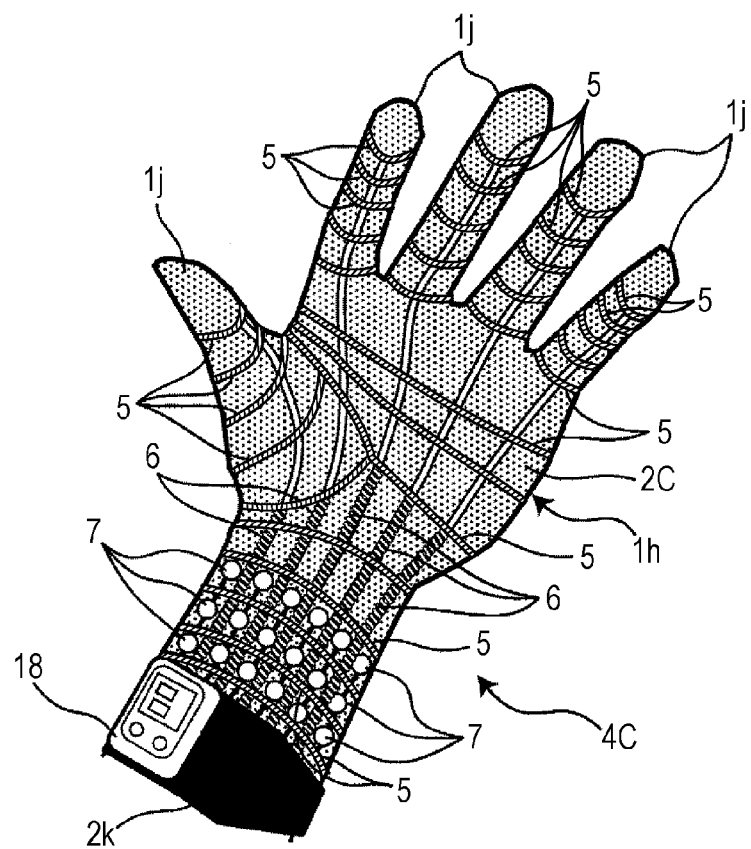
FIG. 53 illustrates a hand and finger assist garment.

Although the foregoing embodiment is directed to an example of implementation of the garment body 2 as underpants, this is not to be construed restrictively. Other implementations of the garment body 2 may include an elbow assist garment 4B worn on an arm 1f to assist the bending and stretching motion of an elbow 1g, and a finger assist garment 4C worn on a hand 1h to assist the bending and stretching motion of fingers 1j as illustrated in FIGS. 52 and 53, respectively. Further, the operating device 18 may not necessarily be provided in the controller belt 3 as a separate component from the garment body 2 as illustrated in FIG. 1. Alternatively, the operating device 18 may be provided in the distal end portion of the garment body 2B worn on the elbow assist garment 4B as illustrated in FIG. 52.

As illustrated in FIG. 52, the elbow assist garment 4B includes the assisting actuators 6 placed in the axial direction of the arm 1f, and the garment-fitting actuators 5 placed in a direction crossing this axial direction.

As illustrated in FIG. 53, the finger assist garment 4C includes the assisting actuators 6 placed in the axial direction of the arm 1f and the fingers 1j, and the garment-fitting actuators 5 placed in a direction crossing this axial direction.

The black band part in FIGS. 52 and 53 is a restraint 2k such as a rubber belt.

The assist garment may be similarly applied to body parts other than those mentioned above, for example, the knee, ankle, or toe.

Although the present disclosure has been described above by way of the first embodiment and the modifications, it is needless to mention that the present disclosure is not limited to the first embodiment and the modifications mentioned above. The following configurations are also within the scope of the present disclosure.

As an example of its specific implementation, the controller 8 may be partially or wholly implemented by a computer system including components such as a microprocessor, a ROM, a RAM, a hard disk unit, a display unit, a keyboard, and a mouse. The RAM or the hard disk unit stores a computer program. Various components achieve their respective functions as the microprocessor operates in accordance with the computer program. As contemplated herein, a computer program is a combination of a plurality of instruction codes to issue commands to a computer in order to achieve predetermined functions.

For example, a software program recorded on a recording medium such as a hard disk or a semiconductor memory may be read and executed by a program execution unit such as a CPU to implement various components.

The software for implementing some or all of the components constituting the controller in the embodiment or the modifications mentioned above is a program as described below.

That is, in one implementation, the program is a program for controlling a controller of an assist garment,
the assist garment being worn on a part of a living body,
the assist garment including
a plurality of assisting actuators that, when worn on the living body, are placed linearly in a direction of extension and contraction of a muscle of the living body, the assisting actuators being driven to extend and contract,
a plurality of fitting actuators placed linearly to cross the assisting actuators, the fitting actuators being driven to extend and contract,
a plurality of sensors placed around the assisting actuators and the fitting actuators, and
a controller that individually controls driving of the assisting actuators and driving of the fitting actuators, based on a detection result from the sensors,
the program being executed in a computer of the controller of the assist garment,
the program including causing the computer of the controller to execute functions including:
contracting one or more first actuators of the fitting actuators;
detecting whether the assist garment is in contact with the living body, by using one or more of the sensors which are placed in areas around the first actuators;
determining, based on a detection result from the sensors, whether all of the areas around the first actuators are in contact with the living body; and
contracting one or more second actuators of the fitting actuators when the controller determines that all of the areas around the first actuators are in contact with the living body.

Further, in another implementation, the program is a program for controlling a controller of an assist garment,
the assist garment being worn on a part of a living body
the assist garment including:
a plurality of assisting actuators that, when worn on the part, are placed linearly in a direction of extension and contraction of a muscle of the part, the assisting actuators being driven to extend and contract,
a plurality of fitting actuators placed linearly to cross the assisting actuators, the fitting actuators being driven to extend and contract, and
a controller that individually controls driving of the assisting actuators and driving of the fitting actuators, the program being executed in the controller of the assist garment, the program including causing a computer of the controller to execute functions including:

driving the fitting actuators to contract; and driving the assisting actuators to extend and contract, after the fitting actuators are driven to contract.

This program may be downloaded from, for example, a server and executed. Alternatively, a program recorded on a predetermined recording medium (for example, an optical disc such as a CD-ROM, a magnetic disk, or a semiconductor memory) may be read and executed.

This program may be executed by a single or a plurality of computers. That is, either centralized processing or decentralized processing may be performed.

The above-mentioned aspect of the present disclosure may be expressed in another form as follows. That is, according to another aspect of the present disclosure, there is provided an assist garment worn on a part of a living body, including:

an assist garment having an end portion;

a plurality of fitting actuators placed linearly in a circumferential direction of at least the one end portion of the assist garment body, the fitting actuators being driven to extend and contract;

a plurality of assisting actuators placed linearly to cross the fitting actuators, the assisting actuators being driven to extend and contract; and a controller that individually controls driving of the assisting actuators and driving of the fitting actuators.

In the above aspect of the present disclosure, the assisting actuators may be placed in the direction of extension and contraction of the muscle in the part when worn on the part.

Any one or more of the various embodiments or modifications described above may be combined with any other one or more embodiments or modifications to obtain their respective effects. Further, in addition to combinations of one or more embodiments with any other one or more embodiments, combinations of one or more modifications with any other one or more modifications, or combinations of one or more embodiments with one or more modifications, combinations of one or more features from different embodiments or different modifications are also possible.

With the assist garment, the control method for controlling a controller of an assist garment, and the recording medium according to the present disclosure, the garment-fitting actuators are used to change the fit of the garment body from loose to tight to provide for a more proper fit of the garment body on the human body, thus allowing the assist force from the assisting actuators to be more properly exerted on, for example, a muscle in the human body. Consequently, the assist garment, the control method, and the recording medium can be used to assist in various activities including: assisting a muscle such as a biceps brachii muscle, a back muscle, a gluteus maximus muscle, or a thigh muscle to assist in tasks such as lifting or carrying heavy objects for the purpose of alleviating heavy physical labor; grip strength assistance that assists in bending and stretching of fingers, or walking assistance that assists a muscle such as a gluteus maximus muscle or a thigh muscle, for purposes such as rehabilitation and supplementing loss of muscle strength; assisting muscles in the vicinity of, for example, the neck, shoulders, or waist for the purpose of massaging; muscle assistance for golf swing lesson that assists muscles in the whole body for the purpose of skill assist; and muscle assistance that places a load in a direction opposite to muscular motion to develop a muscle for the purpose of training.

What is claimed is:

1. An assist garment worn on a part of a living body, the assist garment comprising:

an assist garment body having an inner layer adapted to be located closest to the part of the living body;

a plurality of assisting actuators that, when worn on the part, are placed linearly in a direction of extension and contraction of a muscle of the part, the assisting actuators being driven to extend and contract;

a plurality of fitting actuators placed linearly to cross the assisting actuators, the fitting actuators being driven to extend and contract;

a controller that individually controls driving of the assisting actuators and driving of the fitting actuators, wherein the plurality of assisting actuators includes a first assisting actuator including a first end and a second end, wherein the first assisting actuator includes a first continuous part including the first end, a second continuous part including the second end, and a third continuous part provided between the first continuous part and the second continuous part, wherein the plurality of fitting actuators includes a first fitting actuator, a second fitting actuator, and a third fitting actuator provided between the first fitting actuator and the second fitting actuator, wherein the first continuous part is provided between the first fitting actuator and the inner layer, wherein the second continuous part is provided between the second fitting actuator and the inner layer, and wherein the third fitting actuator is provided between the third continuous part and the inner layer; and a plurality of sensors placed at or around placement positions of the assisting actuators and at or around placement positions of the fitting actuators to detect whether the assist garment is in contact with the living body, wherein the controller controls driving of the fitting actuators based on a detection result obtained from the sensors, wherein the sensors each comprise an electromyogram sensor that detects a voltage generated when the muscle is about to be activated, and wherein the controller controls driving of the assisting actuators based on a detection result obtained from the electromyogram sensor.

2. An assist garment worn on a part of a living body, the assist garment comprising:

an assist garment body having an inner layer adapted to be located closest to the part of the living body;

a plurality of assisting actuators that, when worn on the part, are placed linearly in a direction of extension and contraction of a muscle of the part, the assisting actuators being driven to extend and contract;

a plurality of fitting actuators placed linearly to cross the assisting actuators, the fitting actuators being driven to extend and contract;

a controller that individually controls driving of the assisting actuators and driving of the fitting actuators, wherein the plurality of assisting actuators includes a first assisting actuator including a first end and a second end, wherein the first assisting actuator includes a first continuous part including the first end, a second continuous part including the second end, and a third continuous part provided between the first continuous part and the second continuous part, wherein the plurality of fitting actuators includes a first fitting actuator, a second fitting actuator, and a third fitting actuator provided between the first fitting actuator and the second fitting actuator, wherein the first continuous part is provided between the first fitting actuator and the inner layer, wherein the second continuous part is provided between the second fitting actuator and the inner layer, and wherein the third fitting actuator is provided between the third continuous part and the inner layer;

a plurality of sensors placed at or around placement positions of the assisting actuators and at or around placement positions of the fitting actuators to detect whether the assist garment is in contact with the living body, wherein the controller controls driving of the fitting actuators based on a detection result obtained from the sensors, and wherein the controller controls driving of one or more of the assisting actuators which are placed in proximity to one or more of the sensors which are placed in a region corresponding to the muscle, based on a detection result from the sensors.

3. An assist garment worn on a part of a living body, the assist garment comprising:

an assist garment body having an inner layer adapted to be located closest to the part of the living body;

a plurality of assisting actuators that, when worn on the part, are placed linearly in a direction of extension and contraction of a muscle of the part, the assisting actuators being driven to extend and contract;

a plurality of fitting actuators placed linearly to cross the assisting actuators, the fitting actuators being driven to extend and contract;

a controller that individually controls driving of the assisting actuators and driving of the fitting actuators, wherein the plurality of assisting actuators includes a first assisting actuator including a first end and a second end, wherein the first assisting actuator includes a first continuous part including the first end, a second continuous part including the second end, and a third continuous part provided between the first continuous part and the second continuous part, wherein the plurality of fitting actuators includes a first fitting actuator, a second fitting actuator, and a third fitting actuator provided between the first fitting actuator and the second fitting actuator, wherein the first continuous part is provided between the first fitting actuator and the inner layer, wherein the second continuous part is provided between the second fitting actuator and the inner layer, and wherein the third fitting actuator is provided between the third continuous part and the inner layer;

a plurality of sensors placed at or around placement positions of the assisting actuators and at or around placement positions of the fitting actuators to detect whether the assist garment is in contact with the living body, wherein the controller controls driving of the fitting actuators based on a detection result obtained from the sensors; and a notifier, wherein the fitting actuators include one or more first actuators and one or more second actuators, wherein when the controller determines, based on a detection result from one or more of the sensors which are located at placement positions of the one or more first actuators or in areas around the placement positions of the one or more first actuators, that not all of the placement positions of the one or more first actuators or not all of the areas around the placement positions of the one or more first actuators are in contact with the living body, the controller uses the notifier to provide notification indicating that the assist garment is not in contact with the living body, and wherein the controller drives the one or more first actuators to extend and contract to generate a vibration, together with the notification provided using the notifier.

4. An assist garment worn on a part of a living body, the assist garment comprising:

an assist garment body having an inner layer adapted to be located closest to the part of the living body;

a plurality of assisting actuators that, when worn on the part, are placed linearly in a direction of extension and contraction of a muscle of the part, the assisting actuators being driven to extend and contract;

a plurality of fitting actuators placed linearly to cross the assisting actuators, the fitting actuators being driven to extend and contract; and a controller that individually controls driving of the assisting actuators and driving of the fitting actuators, wherein the plurality of assisting actuators includes a first assisting actuator including a first end and a second end, wherein the first assisting actuator includes a first continuous part including the first end, a second continuous part including the second end, and a third continuous part provided between the first continuous part and the second continuous part, wherein the plurality of fitting actuators includes a first fitting actuator, a second fitting actuator, and a third fitting actuator provided between the first fitting actuator and the second fitting actuator, wherein the first continuous part is provided between the first fitting actuator and the inner layer, wherein the second continuous part is provided between the second fitting actuator and the inner layer, and wherein the third fitting actuator is provided between the third continuous part and the inner layer, and wherein the controller is configured to first drive the fitting actuators to contract, and after contraction of the fitting actuators is completed, to drive the assisting actuators to extend and contract.

5. A method for controlling a controller of an assist garment, the assist garment including:

a plurality of assisting actuators that, when worn on a living body, are placed linearly in a direction of extension and contraction of a muscle of the living body, the assisting actuators being driven to extend and contract;

a plurality of fitting actuators placed linearly to cross the assisting actuators, the fitting actuators being driven to extend and contract;

an inner layer including a plurality of sensors placed around the assisting actuators and the fitting actuators; and a controller that individually controls driving of the assisting actuators and driving of the fitting actuators, based on a detection result from the sensors, wherein the plurality of assisting actuators includes a first assisting actuator including a first end and a second end, wherein the first assisting actuator includes a first continuous part including the first end, a second continuous part including the second end, and a third continuous part provided between the first continuous part and the second continuous part, wherein the plurality of fitting actuators includes a first fitting actuator, a second fitting actuator, and a third fitting actuator provided between the first fitting actuator and the second fitting actuator, wherein the first continuous part is provided between the first fitting actuator and the inner layer, wherein the second continuous part is provided between the second fitting actuator and the inner layer, and wherein the third fitting actuator is provided between the third continuous part and the inner layer, the method comprising:

contracting one or more first actuators of the fitting actuators;

detecting whether the assist garment is in contact with the living body, by using one or more of the sensors which are placed in areas around the one or more first actuators;

determining, based on a detection result from the sensors, whether all of the areas around the one or more first actuators are in contact with the living body; and contracting one or more second actuators of the fitting actuators when the controller determines that all of the areas around the one or more first actuator are in contact with the living body.

6. A recording medium storing a control program for causing an apparatus including a processor to execute an assist process in an assist garment, the recording medium being non-transitory and computer readable, the assist garment including:

a plurality of assisting actuators that, when worn on a living body, are placed linearly in a direction of extension and contraction of a muscle of the living body, the assisting actuators being driven to extend and contract;

a plurality of fitting actuators placed linearly to cross the assisting actuators, the fitting actuators being driven to extend and contract;

an inner layer including a plurality of sensors placed around the assisting actuators and the fitting actuators; and a controller that individually controls driving of the assisting actuators and driving of the fitting actuators, based on a detection result from the sensors, wherein the plurality of assisting actuators includes a first assisting actuator including a first end and a second end, wherein the first assisting actuator includes a first continuous part including the first end, a second continuous part including the second end, and a third continuous part provided between the first continuous part and the second continuous part, wherein the plurality of fitting actuators includes a first fitting actuator, a second fitting actuator, and a third fitting actuator provided between the first fitting actuator and the second fitting actuator, wherein the first continuous part is provided between the first fitting actuator and the inner layer, wherein the second continuous part is provided between the second fitting actuator and the inner layer, and wherein the third fitting actuator is provided between the third continuous part and the inner layer, the assist process comprising causing a computer of the controller to execute functions including:

contracting one or more first actuators of the fitting actuators;

detecting whether the assist garment is in contact with the living body, by using one or more of the sensors which are placed in areas around the one or more first actuators;

determining, based on a detection result from the sensors, whether all of the areas around the one or more first actuators are in contact with the living body; and contracting one or more second actuators of the fitting actuators when the controller determines that all of the areas around the one or more first actuators are in contact with the living body.

\* \* \* \* \*